(12) United States Patent
Box et al.

(10) Patent No.: US 8,198,483 B2
(45) Date of Patent: *Jun. 12, 2012

(54) PHENETHANOLAMINE DERIVATIVES FOR TREATMENT OF RESPIRATORY DISEASES

(75) Inventors: Philip Charles Box, Stevenage (GB); Diane Mary Coe, Stevenage (GB); Brian Edgar Looker, Stevenage (GB); Inderjit Singh Mann, Stevenage (GB); Panayiotis Alexandrou Procopiou, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,037

(22) Filed: Jun. 21, 2011

(65) Prior Publication Data

US 2011/0269970 A1   Nov. 3, 2011

Related U.S. Application Data

(63) Continuation of application No. 12/836,025, filed on Jul. 14, 2010, now Pat. No. 7,982,067, which is a continuation of application No. 12/211,322, filed on Sep. 16, 2008, now Pat. No. 7,776,895, which is a continuation of application No. 11/566,346, filed on Dec. 4, 2006, now Pat. No. 7,439,393, which is a continuation of application No. 10/489,569, filed as application No. PCT/GB02/04140 on Sep. 11, 2002, now Pat. No. 7,361,787.

(30) Foreign Application Priority Data

Sep. 14, 2001 (GB) .................................. 0122201.7
Nov. 9, 2001 (GB) .................................. 0126997.6

(51) Int. Cl.
*C07C 273/00* (2006.01)
*C07C 233/00* (2006.01)
*C07D 413/04* (2006.01)
*C07D 319/08* (2006.01)

(52) U.S. Cl. ............ 564/38; 564/86; 564/194; 548/229; 548/321

(58) Field of Classification Search .................... 564/38, 564/86, 194; 548/321
See application file for complete search history.

(56) References Cited

U.S. PATENT DOCUMENTS

| | | | |
|---|---|---|---|
| 2,140,800 A | 12/1938 | Leemans | |
| 3,994,974 A | 11/1976 | Murakami et al. | |
| 4,730,008 A | 3/1988 | Skidmore et al. | |
| 4,853,381 A | 8/1989 | Finch et al. | |
| 4,853,382 A | 8/1989 | Skidmore et al. | |
| 4,908,386 A | 3/1990 | Finch et al. | |
| 4,937,268 A | 6/1990 | Skidmore et al. | |
| 4,963,564 A | 10/1990 | Skidmore et al. | |
| 4,990,505 A | 2/1991 | Skidmore et al. | |
| 4,992,474 A | 2/1991 | Skidmore et al. | |
| 4,997,986 A | 3/1991 | Mitchell et al. | |
| 5,066,678 A | 11/1991 | Skidmore et al. | |
| 5,091,422 A | 2/1992 | Skidmore et al. | |
| 5,099,068 A | 3/1992 | Mitchell et al. | |
| 5,109,023 A | 4/1992 | Mitchell et al. | |
| 5,126,375 A | 6/1992 | Skidmore et al. | |
| 5,225,445 A | 7/1993 | Skidmore et al. | |
| 5,243,076 A | 9/1993 | Skidmore et al. | |
| 5,283,262 A | 2/1994 | Mitchell et al. | |
| 5,290,815 A | 3/1994 | Johnson et al. | |
| 5,393,774 A | 2/1995 | Pieper et al. | |
| 5,552,438 A | 9/1996 | Christensen, IV | |
| 5,998,428 A | 12/1999 | Barnette et al. | |
| 7,135,600 B2 | 11/2006 | Biggadike et al. | |
| 7,982,067 B2 * | 7/2011 | Box et al. .................. 564/38 |

FOREIGN PATENT DOCUMENTS

| | | |
|---|---|---|
| DE | 3513885 | 10/1985 |
| DE | 3524990 | 1/1986 |
| DE | 4028398 | 3/1992 |
| EP | 0069715 | 1/1983 |
| EP | 162576 | 11/1985 |
| EP | 220054 | 4/1987 |
| EP | 220878 | 5/1987 |
| EP | 223410 | 5/1987 |
| EP | 0286242 | 10/1988 |
| EP | 286242 | 10/1988 |
| EP | 303465 | 2/1989 |
| EP | 0317206 | 5/1989 |
| EP | 0416951 | 3/1991 |
| EP | 223671 | 11/1991 |
| EP | 0401966 | 1/1994 |
| EP | 0947498 | 10/1999 |
| GB | 2064336 | 6/1981 |
| GB | 2129691 | 5/1984 |
| GB | 2140800 | 12/1984 |
| GB | 2159151 | 11/1985 |
| GB | 2162842 | 2/1986 |
| GB | 2169265 | 7/1986 |

(Continued)

OTHER PUBLICATIONS

Dr. Meyer Magarici; Riesgossobre broncodilatadors; SVMS; Nov. 29, 2005.
Drug Bank Chemical Compound Query Result Re Salmeterol; Jul. 31, 2000.
D. Iakovidis, et al."Synthesis and beta-andrenoceptor agonist properties of (+/−)-1-(3',4'-dihydroxyphenoxy)-3-(3",4"-dimethooxyphenyl)ethylamino-2-propanol hydrochloride, (+/−)-(RO363.HCI, and the (2S)-(−)-isomer"; European Journal of Medicinal Chemistry; Jun. 6, 1999; vol. 34, No. 6, pp. 539-548.
Robert Hett, et al., "Enantioselective synthesis of salmeterol via asymmetric borane reduction"Tetrahedron Letters; 1994; vol. 35, No. 50.
U.S. Appl. No. 11/207,967, filed Aug. 19, 2005.

(Continued)

Primary Examiner — Sikarl Witherspoon
(74) Attorney, Agent, or Firm — Robert J. Smith

(57) ABSTRACT

(1R)-2-[(6-{2-[(2,6-dichlorobenzyl)oxy]ethoxy}hexyl)amino]-1-(2,2-dimethyl-4H-1,3-benzodioxin-6-yl)ethanol and (5R)-3-(6-{2-[(2,6-dichlorobenzyl)oxy]ethoxy}hexyl)-5-(2,2-dimethyl-4H-1,3-benzodioxin-6-yl)-1,3-oxazolidin-2-one are claimed.

2 Claims, 2 Drawing Sheets

FOREIGN PATENT DOCUMENTS

| | | |
|---|---|---|
| GB | 2176476 | 12/1986 |
| GB | 2178965 | 2/1987 |
| GB | 2230523 | 10/1990 |
| GB | 2242134 | 9/1991 |
| WO | 95/01170 | 1/1995 |
| WO | 95/19336 | 7/1995 |
| WO | 99/16766 | 4/1999 |
| WO | 99/47505 | 9/1999 |
| WO | 01/04118 | 1/2001 |
| WO | 01/13953 | 3/2001 |
| WO | 02/066422 | 8/2002 |
| WO | 00/51599 | 9/2002 |
| WO | 02/070490 | 9/2002 |
| WO | 2004/071388 | 8/2004 |

OTHER PUBLICATIONS

U.S. Appl. No. 11/207,967, final office action dated Jun. 19, 2007.
U.S. Appl. No. 11/426,657, non-final office dated Jun. 25, 2007.
U.S. Appl. No. 11/207,967, non-final office action dated Jan. 11, 2007.
U.S. Appl. No. 11/426,661, non-final office action dated Jan. 12, 2007.
U.S. Appl. No. 11/426,661, non-final office action dated Jul. 5, 2007.
U.S. Appl. No. 11/426,657, non-final office action dated Jan. 12, 2007.
Thornber "Isosterism and molecular modification in drug design" Chemical Society Reviews; 8(4) 563-580, (1979).
U.S. Appl. No. 10/522,321, filed Jul. 6, 2005.
U.S. Appl. No. 11/207,667, filed Aug. 19, 2005.
U.S. Appl. No. 11/426,657, filed Jun. 27, 2006.
U.S. Appl. No. 11/426,661, filed Jun. 27, 2006.
Official Action, date mailed Mar. 15, 2007, U.S. Appl. No. 10/522,321.
Fuji et al., "Novel phosphodiesterase 4 Inhibitor T-440 reverses and prevents human bronchial contraction induced by allergen" J. Pharmacol Exp Ther 284(1): 162(1998).
Landells et al. "Oral administration of the phosphodiesterase (PDE)4 inhibitor. V11294A Inhibits ex-vivo agonist-induced-cell-activation" Eur Resp J (annu Cong Eur Resp Soc. Geneva) 12(Suppl 28) Abst P2393 (Sep. 1998).
McHale et al. Expressin of human recombinant cAMP phosphodiesterase isozyme IV reverses growth arrest phenotypes in phosphodiesterase-deficient yeast, Molec. Pharmacol. Sci. 39, 109-113 (1991).
Nicholson et al, "Differential modulation of tissue function and therapeutic potential of selective inhibitors of cyclic nucleotide phosphodiesterase isoenzymes." Trends Pharmacol Sci 12: 19-27(1991).
Torphy et al., "Role of cyclic nucleotide phosphodiesterase isozymes in intact canine trachealis" Mol. Pharmacol. 39:376-384 (1991).

* cited by examiner

PHENETHANOLAMINE DERIVATIVES FOR TREATMENT OF RESPIRATORY DISEASES

CROSS-REFERENCE TO RELATED APPLICATIONS

This application is a continuation application of Ser. No. 12/836,025 filed Jul. 14, 2010 now U.S. Pat. No. 7,982,067, now allowed, which is a continuation of Ser. No. 12/211,322 filed Sep. 16, 2008, now U.S. Pat. No. 7,776,895, which is a continuation of Ser. No. 11/566,346, filed Dec. 4, 2006, now U.S. Pat. No. 7,439,393 B2, which is a continuation application of Ser. No. 10/489,569, filed Nov. 29, 2004, now U.S. Pat. No. 7,361,787 B2, which was filed under 35 U.S.C. §371 as the United States National Phase Application of International Application No. PCT/GB02/04140 filed Sep. 11, 2002 claiming priority from Great Britain Application Nos. 0122201.7 and 0126997.6 filed Sep. 14, 2001 and Nov. 9, 2001 respectively.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

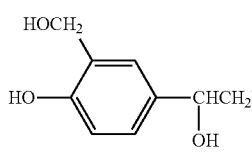 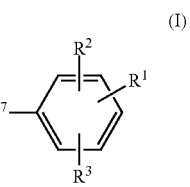

(I)

or a salt, solvate, or physiologically functional derivative thereof, wherein:
m is an integer of from 2 to 8;
n is an integer of from 2 to 5;
with the proviso that m+n is 4 to 10;
$R^1$ is selected from hydrogen, $C_{1-6}$alkyl, hydroxy, halo, $C_{1-6}$haloalkyl, —XC(O)NR$^9$R$^{10}$, —XNR$^8$C(O)R$^9$, —XNR$^8$C(O)NR$^9$R$^{10}$, —XNR$^8$SO$_2$R$^9$, —XSO$_2$NR$^{11}$R$^{12}$, XNR$^8$SO$_2$R$^9$R$^{10}$, —XNR$^9$R$^{10}$, XN$^+$R$^8$R$^9$R$^{10}$, —XNR$^8$C(O)OR$^9$, —XCO$_2$R$^9$, —XNR$^8$C(O)NR$^8$C(O)NR$^9$R$^{10}$, —XSR$^9$, XSOR$^9$, and —XSO$_2$R$^9$;
or $R^1$ is selected from —X-aryl, —X-hetaryl, and —X-(aryloxy), each optionally substituted by 1 or 2 groups independently selected from hydroxy, $C_{1-6}$alkoxy, halo, $C_{1-6}$alkyl, $C_{1-6}$haloalkyl, —NHC(O)($C_{1-6}$alkyl), —SO$_2$($C_{1-6}$alkyl), —SO$_2$(aryl), —SO$_2$NH$_2$, —SO$_2$NH($C_{1-6}$alkyl), —SO$_2$NH($C_{3-7}$cycloalkyl), —CO$_2$H, —CO$_2$($C_{1-6}$alkyl), —SO$_2$NH($C_{3-7}$cycloalkylC$_{1-6}$alkyl), —NH$_2$, —NH($C_{1-6}$alkyl), or hetaryl optionally substituted by 1 or 2 groups independently selected from hydroxy, $C_{1-6}$alkoxy, halo, $C_{1-6}$alkyl, or $C_{1-6}$haloalkyl;
X is —(CH$_2$)$_p$— or $C_{2-6}$ alkenylene;
p is an integer from 0 to 6, preferably 0 to 4;
$R^8$ and $R^9$ are independently selected from hydrogen, $C_{1-6}$alkyl, $C_{3-7}$cycloalkyl, aryl, hetaryl, hetaryl($C_{1-6}$alkyl)- and aryl($C_{1-6}$alkyl)- and $R^8$ and $R^9$ are each independently optionally substituted by 1 or 2 groups independently selected from halo, $C_{1-6}$alkyl, $C_{1-6}$haloalkyl, —NHC(O)($C_{1-6}$alkyl), —SO$_2$($C_{1-6}$alkyl), —SO$_2$(aryl), —CO$_2$H, —CO$_2$($C_{1-6}$alkyl), —NH$_2$, —NH($C_{1-6}$alkyl), aryl($C_{1-6}$alkyl)-, aryl($C_{2-6}$alkenyl)-, aryl($C_{2-6}$alkynyl)-, hetaryl($C_{1-6}$alkyl)-, —NHSO$_2$aryl, —NH(hetarylC$_{1-6}$alkyl), —NHSO$_2$hetaryl, —NHSO$_2$($C_{1-6}$alkyl), —NHC(O)aryl, or —NHC(O)hetaryl:
$R^{10}$ is selected from hydrogen, $C_{1-6}$alkyl and $C_{3-7}$ cycloalkyl;
$R^{11}$ and $R^{12}$ are independently selected from hydrogen, $C_{1-6}$alkyl, $C_{3-7}$cycloalkyl, aryl, hetaryl, hetaryl($C_{1-6}$alkyl)- and aryl($C_{1-6}$alkyl)-, or $R^{11}$ and $R^{12}$, together with the nitrogen to which they are bonded, form a 5-, 6-, or 7-membered nitrogen containing ring; and $R^{11}$ and $R^{12}$ are each optionally substituted by one or two groups independently selected from halo, $C_{1-6}$alkyl, and $C_{1-6}$haloalkyl;
where $R^1$ is —XNR$^8$C(O)NR$^9$R$^{10}$, $R^8$ and $R^9$ may, together with the —NC(O)N— portion of the group $R^1$ to which they are bonded, form a saturated or unsaturated ring, preferably a 5-, 6-, or 7-membered ring, for example an imidazolidine or pyrimidine ring, such as imidazolidine-2,4-dione or pyrimidine-2,4-dione;
where $R^1$ is —XNR$^8$C(O)OR$^9$, $R^8$ and $R^9$ may, together with the —NC(O)O— portion of the group $R^1$ to which they are bonded, form a saturated or unsaturated ring, preferably a 5-, 6-, or 7-membered ring, for example an oxazolidine ring, such as oxazolidine-2,4-dione;
where $R^1$ is —XC(O)NR$^9$R$^{10}$ or —XNR$^8$C(O)NR$^9$R$^{10}$, $R^9$ and $R^{10}$ may, together with the nitrogen to which they are bonded, form a 5-, 6-, or 7-membered nitrogen containing ring;

$R^2$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;
$R^3$ is selected from hydrogen, hydroxy, $C_{1-6}$alkyl, $C_{1-6}$alkoxy, halo, aryl, aryl($C_{1-6}$alkyl)-, $C_{1-6}$haloalkoxy, and $C_{1-6}$haloalkyl;
$R^4$ and $R^5$ are independently selected from hydrogen and $C_{1-4}$ alkyl with the proviso that the total number of carbon atoms in $R^4$ and $R^5$ is not more than 4; and,
$R^6$ and $R^7$ are independently selected from hydrogen and $C_{1-4}$alkyl with the proviso that the total number of carbon atoms in $R^4$ and $R^5$ is not more than 4.

In the compounds of formula (I) and (Ia), $R^6$ and $R^7$ are preferably independently selected from hydrogen and methyl, more preferably $R^6$ and $R^7$ are both hydrogen.

In the compounds of formula (I), m is suitably 4, 5 or 6, more suitably 4 or 5 and preferably, 5 and n is suitably 2 or 3 and preferably n is 2.

Figure 1:
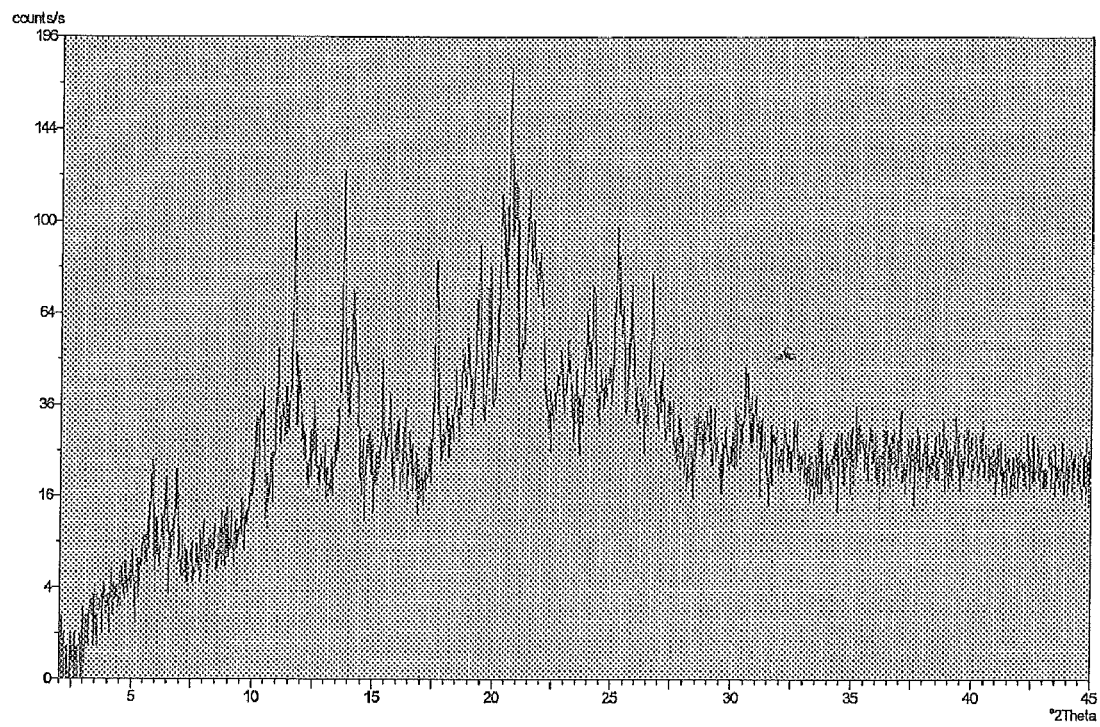
FIG. 1 illustrates an XRPD pattern of a triphenyacetate salt referred to in Example 78.

According to a preferred aspect of the invention, there is provided a compound of formula (Ia)

(Ia)

$$HOCH_2\text{-}HO\text{-}C_6H_3\text{-}CH(OH)CH_2NHCH_2(CH_2)_m\text{-}O\text{-}(CH_2)_2\text{-}OCR^6R^7\text{-}C_6H_2(R^1)(R^2)(R^3)$$

or a salt, solvate, or physiologically functional derivative thereof, wherein $R^1$, $R^2$, $R^3$, $R^6$ and $R^7$ are as defined above for formula (I) and m is 4 or 5.

In the compounds of formulae (I) and (Ia), the group $R^1$ is preferably attached to the para- or meta-position, and more preferably to the meta-position relative to the —$OCR^6R^7$-link. The groups $R^2$ and $R^3$ are each independently preferably attached to the ortho- or meta-position, more preferably to the ortho position relative to the —$OCR^6R^7$-link.

In one preferred embodiment $R^1$ represents a substituent as defined above, other than hydrogen, most preferably attached to the meta-position relative to the —$OCR^6R^7$-link, and $R^2$ and $R^3$ each represent hydrogen.

In another preferred embodiment $R^1$ represents hydrogen and $R^2$ and $R^3$ each represent a substituent as defined above, at least one of which is other than hydrogen, and $R^2$ and $R^3$ are each independently attached to the ortho- or meta-positions relative to the —$OCR^6R^7$-link. In a particular embodiment, when $R^2$ and $R^3$ each represent halogen they are preferably attached at the ortho positions and when $R^2$ and $R^3$ each represent methyl they are preferably attached at the meta positions.

In the compounds of formulae (I) and (Ia) $R^1$ is suitably selected from hydrogen, $C_{1-6}$alkyl, hydroxy, halo, $C_{1-6}$haloalkyl, —$XNR^8C(O)OR^9$, —$XNR^8C(O)NR^9R^{10}$, —$XNR^8SO_2R^9$, —$XSO_2NR^{11}R^{12}$, —$XNR^9R^{10}$, —$XNR^8C(O)OR^9$, $XSR^9$, $XSOR^9$, $XSO_2R^9$, or from X-aryl, X-hetaryl or X-aryloxy, optionally substituted as defined above.

X is suitably $(CH_2)_p$ wherein p is preferably zero.

$R^8$ and $R^{10}$ suitably represent hydrogen.

$R^9$ suitably represents hydrogen, $C_{1-6}$alkyl, $C_{3-7}$cycloalkyl, aryl, hetaryl or hetaryl($C_{1-6}$alkyl)-, any of which may be optionally substituted by $C_{1-6}$alkyl, $C_{1-6}$haloalkyl, —$SO_2(C_{1-6}$alkyl,), $NH_2$, aryl ($C_{1-6}$alkyl), aryl($C_{2-6}$alkynyl), $NHSO_2$aryl, —NH(hetaryl($C_{1-6}$alkyl), NHC(O)aryl or NHC(O)hetaryl.

$R^{11}$ and $R^{12}$ are suitably each independently selected from hydrogen, $C_{1-6}$alkyl and C3-7cycloalkyl.

In the definition of $R^1$, the term "5-, 6-, or 7-membered nitrogen containing ring" means a 5-, 6-, or 7-membered saturated or unsaturated ring which includes a nitrogen atom and optionally 1 or 2 other heteroatoms independently selected from nitrogen, sulphur, and oxygen. Suitable examples of such a ring include piperidinyl, morpholinyl, pyridyl, 2,4-dihydroxypyrimidinyl, and piperazinyl.

In the definition of $R^1$, the term "hetaryl" means a 5- to 10-membered heteroaromatic ring or bicyclic ring system which includes 1, 2, or 3 heteroatoms independently selected from oxygen, nitrogen and sulphur, such as thienyl, pyridyl, 2,4-dihydroxypyrimidinyl, 2,3-dihydroimidazo[2,1-b][1,3]thiazol-6-yl, or bipyridyl, preferably a 5- or 6-membered heteroaromatic ring.

As used herein, the term "aryl" either alone or in the term "aryloxy" means a monocyclic or bicyclic aromatic ring system, such as phenyl, naphthyl, or biphenyl. Preferably the term "aryl" means phenyl.

In the compounds of formulae (I) and (Ia), the group $R^1$ is preferably selected from hydrogen, $C_{1-4}$alkyl, hydroxy, halo, —$NR^8C(O)NR^9R^{10}$, and —$NR^8SO_2R^9$ wherein $R^8$ and $R^9$ are as defined above or more suitably wherein $R^8$ is hydrogen and $R^9$ is selected from hydrogen, $C_{1-6}$alkyl, $C_{3-6}$cycloalkyl, and aryl and is optionally substituted as described above.

In the compounds of formulae (I) and (Ia) wherein the group $R^1$ is substituted by $R^8$ and/or $R^{10}$, $R^8$ and/or $R^{10}$ are suitably hydrogen.

In the compounds of formula (I) and (Ia) $R^2$ and $R^3$ are preferably independently selected from hydrogen, halogen (eg. fluorine or more preferably chlorine), halo $C_{1-6}$alkyl (eg. $CF_3$), $C_{1-6}$alkyl (eg. methyl) and phenyl or substituted phenyl (eg. p-methoxyphenyl).

In the compounds of formula (I), $R^4$ and $R^5$ are preferably independently selected from hydrogen and methyl, more preferably $R^4$ and $R^5$ are both hydrogen.

It is to be understood that the present invention covers all combinations of particular and preferred groups described hereinabove.

Preferred compounds of the invention include:

N-{3-[(2-{[6-({(2R)-2-hydroxy-2-[4-hydroxy-3-(hydroxymethyl)phenyl]ethyl}-amino)hexyl]oxy}ethoxy)methyl]phenyl}-N'-phenylurea;

4-{(1R)-2-[(6-{2-[(2,6-dichlorobenzyl)oxy]ethoxy}hexyl)amino]-1-hydroxyethyl}-2-(hydroxymethyl)phenol;

N-(1,1'-biphenyl-4-yl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea;

N-cyclohexyl-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea;

4-[(1R)-2-({6-[2-(benzyloxy)ethoxy]hexyl}amino)-1-hydroxyethyl]-2-(hydroxymethyl)phenol;

4-[(2-{[6-({(2R)-2-hydroxy-2-[4-hydroxy-3-(hydroxymethyl)phenyl]ethyl}amino)-hexyl]oxy}ethoxy)methyl]benzenesulfonamide;

4-{(1R)-1-hydroxy-2-[(6-{2-[(4-iodobenzyl)oxy]ethoxy}hexyl)amino]ethyl}-2-(hydroxymethyl)phenol;

3-[(2-{[6-({(2R)-2-hydroxy-2-[4-hydroxy-3-(hydroxymethyl)phenyl]ethyl}amino)-hexyl]oxy}ethoxy)methyl]benzenesulfonamide;

2-(hydroxymethyl)-4-((1R)-1-hydroxy-2-{[6-(2-{[(1R)-1-phenylethyl]oxy}ethoxy)-hexyl]amino}ethyl)phenol;

2-(hydroxymethyl)-4-((1R)-1-hydroxy-2-{[6-(2-{[(1S)-1-phenylethyl]oxy}ethoxy)-hexyl]amino}ethyl)phenol;

4-{(1R)-2-[(6-{2-[(4-chlorobenzyl)oxy]ethoxy}hexyl)amino]-1-hydroxyethyl}-2-(hydroxymethyl)phenol;

2-(hydroxymethyl)-4-{(1R)-1-hydroxy-2-[(6-{2-[(4-methylbenzyl)oxy]-ethoxy}hexyl)amino]ethyl}phenol;

4-{(1R)-2-[(6-{2-[(2,4-dichlorobenzyl)oxy]ethoxy}hexyl)amino]-1-hydroxyethyl}-2-(hydroxymethyl)phenol;

2-(hydroxymethyl)-4-((1R)-1-hydroxy-2-{[6-(2-{[4-(trifluoromethyl)benzyl]-oxy}ethoxy)hexyl]amino}ethyl)phenol;

4-{(1R)-1-hydroxy-2-[(6-{2-[(3-hydroxybenzyl)oxy]ethoxy}hexyl)amino]ethyl}-2-(hydroxymethyl)phenol;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}urea;

N-{3-[(2-{[6-({(2R)-2-hydroxy-2-[4-hydroxy-3-(hydroxymethyl)phenyl]ethyl}amino)hexyl]oxy}ethoxy)methyl]phenyl}-4-(methylsulfonyl)benzenesulfonamide;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}methanesulfonamide;

N-(3-{[({3-[(2-{[6-({(2R)-2-hydroxy-2-[4-hydroxy-3-(hydroxymethyl)phenyl]ethyl}-amino)hexyl]oxy}ethoxy)methyl]phenyl}amino)carbonyl]amino}phenyl)pyridine-3-carboxamide;

N-(3-ethylphenyl)-N'-{3-[(2-{[6-({(2R)-2-hydroxy-2-[4-hydroxy-3-(hydroxymethyl)-phenyl]ethyl}amino)hexyl]oxy}ethoxy)methyl]phenyl}urea;

N-{3-[(2-{[6-({(2R)-2-hydroxy-2-[4-hydroxy-3-(hydroxymethyl)phenyl]-ethyl}amino)hexyl]oxy}ethoxy)methyl]phenyl}-N'-(3-methylphenyl)urea;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}-N'-[3-(trifluoromethyl)phenyl]urea;

N-(3,5-dichlorophenyl)-N'-{2-[(2-{[6-({(2R)-2-hydroxy-2-[4-hydroxy-3-(hydroxymethyl)phenyl]ethyl}amino)hexyl]oxy}ethoxy)methyl]phenyl}urea;

N-(3-chlorophenyl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea;

N-{3-[(2-{[6-({(2R)-2-hydroxy-2-[4-hydroxy-3-(hydroxymethyl)phenyl]-ethyl}amino)hexyl]oxy}ethoxy)methyl]phenyl}-N'-(3-iodophenyl)urea;

4-{(1R)-2-[(6-{2-[(3-aminobenzyl)oxy]ethoxy}hexyl)amino]-1-hydroxyethyl}-2-(hydroxymethyl)phenol;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}pyridine-3-carboxamide;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}thiophene-2-carboxamide;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}benzamide;

3-(benzoylamino)-N-{3-[(2-{[6-({(2R)-2-hydroxy-2-[4-hydroxy-3-(hydroxymethyl)-phenyl]ethyl}amino)hexyl]oxy}ethoxy)methyl]phenyl}benzamide;

N-{3-[({3-[(2-{[6-({(2R)-2-hydroxy-2-[4-hydroxy-3-(hydroxymethyl)phenyl]ethyl}-amino)hexyl]oxy}ethoxy)methyl]phenyl}amino)carbonyl]phenyl}thiophene-2-carboxamide;

N-{3-[({3-[(2-{[6-({(2R)-2-hydroxy-2-[4-hydroxy-3-(hydroxymethyl)phenyl]ethyl}-amino)hexyl]oxy}ethoxy)methyl]phenyl}amino)carbonyl]phenyl}nicotinamide;

N-(3-{[({3-[(2-{[6-({(2R)-2-hydroxy-2-[4-hydroxy-3-(hydroxymethyl)phenyl]ethyl}-amino)hexyl]oxy}ethoxy)methyl]phenyl}amino)carbonyl]amino}phenyl)-benzenesulfonamide;

4-[(1R)-2-({6-[2-(1,1'-biphenyl-2-ylmethoxy)ethoxy]hexyl}amino)-1-hydroxyethyl]-2-(hydroxymethyl)phenol;

4-{(1R)-1-hydroxy-2-[(6-{2-[(4'-methoxy-1,1'-biphenyl-2-yl)methoxy]ethoxy}-hexyl)amino]ethyl}-2-(hydroxymethyl)phenol;

4-{(1R)-2-[(6-{2-[(3-bromobenzyl)oxy]ethoxy}hexyl)amino]-1-hydroxyethyl}-2-(hydroxymethyl)phenol;

2-(hydroxymethyl)-4-{(1R)-1-hydroxy-2-[(6-{2-[(3-phenoxybenzyl)oxy]ethoxy}-hexyl)amino]ethyl}phenol;

4-{(1R)-1-hydroxy-2-[(6-{2-[(4-hydroxybenzyl)oxy]ethoxy}hexyl)amino]ethyl}-2-(hydroxymethyl)phenol;

5-{3-[(2-{[6-({(2R)-2-hydroxy-2-[4-hydroxy-3-(hydroxymethyl)phenyl]ethyl}-amino)hexyl]oxy}ethoxy)methyl]phenyl}pyrimidine-2,4-diol;

4-{(1R)-2-[(6-{2-[(2,5-dichlorobenzyl)oxy]ethoxy}hexyl)amino]-1-hydroxyethyl}-2-(hydroxymethyl)phenol;

4-{(1R)-2-[(6-{2-[(3,5-dimethylbenzyl)oxy]ethoxy}hexyl)amino]-1-hydroxyethyl}-2-(hydroxymethyl)phenol;

4-((1R)-2-{[6-(2-{[2-fluoro-6-(trifluoromethyl)benzyl]oxy}ethoxy)hexyl]amino}-1-hydroxyethyl)-2-(hydroxymethyl)phenol;

2-(hydroxymethyl)-4-((1R)-1-hydroxy-2-{[6-(2-{[3-(trifluoromethoxy)benzyl]-oxy}ethoxy)hexyl]amino}ethyl)phenol;

2-(hydroxymethyl)-4-{(1R)-1-hydroxy-2-[(6-{2-[(2-methyl-1,1'-biphenyl-3-yl)methoxy]ethoxy}hexyl)amino]ethyl}phenol;

3-[(2,3-dihydroimidazo[2,1-b][1,3]thiazol-6-ylmethyl)amino]-N-{3-[(2-{[6-({(2R)-2-hydroxy-2-[4-hydroxy-3-(hydroxymethyl)phenyl]ethyl}amino)hexyl]oxy}ethoxy)-methyl]phenyl}benzamide;

N-(3-{[({3-[(2-{[6-({(2R)-2-hydroxy-2-[4-hydroxy-3-(hydroxymethyl)phenyl]ethyl}amino)hexyl]oxy}ethoxy)methyl]phenyl}amino)carbonyl]amino}phenyl)benzamide;

N-(3-{[({3-[(2-{[6-({(2R)-2-hydroxy-2-[4-hydroxy-3-(hydroxymethyl)phenyl]ethyl}-amino)hexyl]oxy}ethoxy)methyl]phenyl}amino)carbonyl]amino}phenyl)thiophene-2-carboxamide;

N-(1,1'-biphenyl-3-yl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea;

N-(3-aminophenyl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea;

3-[(2-{[6-({(2R)-2-hydroxy-2-[4-hydroxy-3-(hydroxymethyl)phenyl]ethyl}amino)-hexyl]oxy}ethoxy)methyl]-N-methylbenzenesulfonamide;

N-{3-[(2-{[6-({(2R)-2-hydroxy-2-[4-hydroxy-3-(hydroxymethyl)phenyl]ethyl}-amino)hexyl]oxy}ethoxy)methyl]phenyl}-3-[(thien-2-ylsulfonyl)amino]benzamide;

N-{3-[(2-{[6-({(2R)-2-hydroxy-2-[4-hydroxy-3-(hydroxymethyl)-phenyl]ethyl}amino)hexyl]oxy}ethoxy)methyl]phenyl}-N'-[3-(2-phenylethyl)-phenyl]urea;

cyclopentyl 3-[(2-{[6-({(2R)-2-hydroxy-2-[4-hydroxy-3-(hydroxymethyl)phenyl]-ethyl}amino)hexyl]oxy}ethoxy)methyl]phenylcarbamate;

5-{3'-[(2-{[6-({(2R)-2-hydroxy-2-[4-hydroxy-3-(hydroxymethyl)-phenyl]ethyl}amino)hexyl]oxy}ethoxy)methyl]-1,1'-biphenyl-3-yl}pyrimidine-2,4(1H,3H)-dione;
4-{(1R)-1-hydroxy-2-[(6-{2-[(3-iodobenzyl)oxy]ethoxy}hexyl)amino]-ethyl}-2-(hydroxymethyl)phenol;
3'-[(2-{[6-({(2R)-2-hydroxy-2-[4-hydroxy-3-(hydroxymethyl)phenyl]-ethyl}amino)hexyl]oxy}ethoxy)methyl]-1,1'-biphenyl-3-ol;
N-cyclohexyl-3-[(2-{[6-({(2R)-2-hydroxy-2-[4-hydroxy-3-(hydroxymethyl)phenyl]-ethyl}amino)hexyl]oxy}ethoxy)methyl]benzenesulfonamide;
N-{3-[(2-{[6-({(2R)-2-hydroxy-2-[4-hydroxy-3-(hydroxymethyl)-phenyl]ethyl}-amino)hexyl]oxy}ethoxy)methyl]phenyl}-3-[(phenylsulfonyl)amino]benzamide;
4-[(1R)-2-({6-[2-({3-[(2,3-dihydroimidazo[2,1-b][1,3]thiazol-6-ylmethyl)amino]-benzyl}oxy)ethoxy]hexyl}amino)-1-hydroxyethyl]-2-(hydroxymethyl)phenol;
N-cyclopropyl-3'-[(2-{[6-({(2R)-2-hydroxy-2-[4-hydroxy-3-(hydroxy-methyl)-phenyl]ethyl}amino)hexyl]oxy}ethoxy)methyl]-1,1'-biphenyl-2-sulfonamide;
N-{3-[(2-{[6-({(2R)-2-hydroxy-2-[4-hydroxy-3-(hydroxymethyl)-phenyl]ethyl}-amino)hexyl]oxy}ethoxy)methyl]phenyl}-N'-[3-(phenylethynyl)phenyl]urea;
N-{3-[(2-{[5-({(2R)-2-Hydroxy-2-[4-hydroxy-3-(hydroxymethyl)phenyl]ethyl}amino)pentyl]oxy}ethoxy)methyl]phenyl}-N'-phenylurea;
N-{3-[(3-{[5-({(2R)-2-Hydroxy-2-[4-hydroxy-3-(hydroxymethyl)phenyl]ethyl}amino)pentyl]oxy}propoxy)methyl]phenyl}-N'-phenylurea;
N-{3-[(2-{[7-({(2R)-2-Hydroxy-2-[4-hydroxy-3-(hydroxymethyl)phenyl]ethyl}amino)heptyl]oxy}ethoxy)methyl]phenyl}-N'-phenylurea;
N-(3-{[({3-[(2-{[5-({(2R)-2-Hydroxy-2-[4-hydroxy-3-(hydroxymethyl)phenyl]ethyl}amino)pentyl]oxy}ethoxy)methyl]phenyl}amino)carbonyl]amino}phenyl)nicotinamide;
N-(3-{[({3-[(3-{[5-({(2R)-2-Hydroxy-2-[4-hydroxy-3-(hydroxymethyl)phenyl]ethyl}amino)pentyl]oxy}propoxy)methyl]phenyl}amino)carbonyl]amino}phenyl)nicotinamide;
N-(3-{[({3-[(3-{[7-({(2R)-2-Hydroxy-2-[4-hydroxy-3-(hydroxymethyl)phenyl]ethyl}amino)heptyl]oxy}propoxy)methyl]phenyl}amino)carbonyl]amino}phenyl)nicotinamide;
N-{3-[(2-{[5-({(2R)-2-Hydroxy-2-[4-hydroxy-3-(hydroxymethyl)phenyl]ethyl}amino)pentyl]oxy}ethoxy)methyl]phenyl}methanesulfonamide;
N-{3-[(3-{[5-({(2R)-2-Hydroxy-2-[4-hydroxy-3-(hydroxymethyl)phenyl]ethyl}amino)pentyl]oxy}prop)methyl]phenyl}methanesulfonamide;
N-{3-[(2-{[7-({(2R)-2-Hydroxy-2-[4-hydroxy-3-(hydroxymethyl)phenyl]ethyl}amino)heptyl]oxy}ethoxy)methyl]phenyl}methanesulfonamide;
N-{3-[(2-{[6-({(2R)-2-Hydroxy-2-[4-hydroxy-3-(hydroxymethyl)phenyl]ethyl}amino)hexyl]oxy}ethoxy)methyl]phenyl}benzenesulfonamide;
4-((1R)-2-{[6-(2-{[3-(Dimethylamino)benzyl]oxy}ethoxy)hexyl]amino}-1-hydroxyethyl)-2-(hydroxymethyl)phenol;
3-[(2-{[6-({(2R)-2-Hydroxy-2-[4-hydroxy-3-(hydroxymethyl)phenyl]ethyl}amino)hexyl]oxy}ethoxy)methyl]-N,N,N-trimethylbenzenaminium;
N-{4-[(2-{[6-({(2R)-2-Hydroxy-2-[4-hydroxy-3-(hydroxymethyl)phenyl]ethyl}amino)hexyl]oxy}ethoxy)methyl]phenyl}-N'-phenylurea;
4-{(1R)-2-[(5-{2-[(2,6-dichlorobenzyl)oxy]ethoxy}pentyl)amino]-1-hydroxyethyl}-2-(hydroxymethyl)phenol;
and salts, solvates, and physiologically functional derivatives thereof.

Particularly preferred compounds of the invention include:
N-{3-[(2-{[6-({(2R)-2-hydroxy-2-[4-hydroxy-3-(hydroxymethyl)phenyl]ethyl}-amino)hexyl]oxy}ethoxy)methyl]phenyl}-N'-phenylurea;
4-{(1R)-2-[(6-{2-[(2,6-dichlorobenzyl)oxy]ethoxy}hexyl)amino]-1-hydroxyethyl}-2-(hydroxymethyl)phenol;
N-(3-{[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]amino}phenyl)pyridine-3-carboxamide;
4-{(1R)-1-Hydroxy-2-[(6-{2-[(3-hydroxybenzyl)oxy]ethoxy}hexyl)amino]ethyl}-2-(hydroxymethyl)phenol;
4-{(1R)-2-[(6-{2-[(3,5-Dimethylbenzyl)oxy]ethoxy}hexyl)amino]-1-hydroxyethyl}-2-(hydroxymethyl)phenol;
N-{3-[(2-{[5-({(2R)-2-Hydroxy-2-[4-hydroxy-3-(hydroxymethyl)phenyl]ethyl}amino)pentyl]oxy}ethoxy)methyl]phenyl}-N'-phenylurea;
and salts, solvates, and physiologically functional derivatives thereof.

Particularly preferred compounds of the invention further include:
4-{(1R)-2-[(6-{2-[(2,6-dichlorobenzyl)oxy]ethoxy}hexyl)amino]-1-hydroxyethyl}-2-(hydroxymethyl)phenol;
and salts and solvates thereof.

The compounds of formulae (I) and (Ia) include an asymmetric centre, namely the carbon atom of the

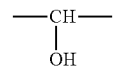

group. The present invention includes both (S) and (R) enantiomers either in substantially pure form or admixed in any proportions.

Similarly, where $R^4$ and $R^5$ are different groups or where $R^6$ and $R^7$ are different groups, the carbon atom to which they are attached is an asymmetric centre and the present invention includes both (S) and (R) isomers at these centres either in substantially pure form or admixed in any proportions.

Thus the compounds of formulae (I) and (Ia) include all enantiomers and diastereoisomers as well as mixtures thereof in any proportions.

Salts and solvates of compounds of formulae (I) and (Ia) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (I) and (Ia) and their pharmaceutically acceptable salts, solvates, and physiologically functional derivatives.

By the term "physiologically functional derivative" is meant a chemical derivative of a compound of formula (I) or (Ia) having the same physiological function as the free compound of formula (I) or (Ia), for example, by being convertible in the body thereto. According to the present invention, examples of physiologically functional derivatives include esters.

Pharmaceutically acceptable esters of the compounds of formula (I) and (Ia) may have a hydroxyl group converted to a $C_{1-6}$ alkyl, aryl, aryl $C_{1-6}$ alkyl, or amino acid ester.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, phenylacetic, substituted phenyl acetic eg. methoxyphenyl acetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, mandelic, cinnamic, substituted cinnamic (for example, methyl, methoxy, halo or phenyl substituted cinnamic, including 4-methyl and 4-methoxycinnamic acid and α-phenyl cinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, bezeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Advantageously, preferred compounds of the invention such as 4-{(1R)-2-[(6-{2-[(2,6-dichlorobenzyl)oxy]ethoxy}hexyl)amino]-1-hydroxyethyl}-2-(hydroxymethyl)phenol are provided in the form of a crystalline salt, for example selected from those exemplified in the experimental section below. Said crystalline salts have favourable physical properties such as low hygroscopicity and/or improved stability.

As mentioned above, the compounds of formulae (I) and (Ia) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. In addition, compounds of the invention demonstrate pharmacokinetic properties that will reduce systemic exposure relative to existing long-acting beta2 agonist bronchodilators. As such, compounds of the invention may be suitable for once-daily administration.

Therefore, compounds of formulae (I) and (Ia) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (eg. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I) or (Ia), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I) or (Ia) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I) or (Ia) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I) or (Ia) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I) or (Ia), or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I) or (Ia), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I) or (Ia), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

While it is possible for the compound of formula (I) or (Ia), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or (Ia) or a pharmaceutically acceptable salt, solvate, or physiologically functional derivative thereof, and a pharmaceutically acceptable carrier or excipient, and optionally one or more other therapeutic ingredients.

The compounds and pharmaceutical formulations according to the invention may be used in combination with or include one or more other therapeutic agents, for example anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example, an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, and 6α,9α-difluoro-17α-[(2-furanylcarbonyl)oxy]-11β-hydroxy-16α-methyl-3-oxo-androsta-1,4-diene-17β-carbothioic acid S-fluoromethyl ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4. Initial experiments were conducted to establish and validate a [$^3$H]-rolipram binding assay. Details of this work are given in the Binding Assays described in detail below.

The preferred PDE4 inhibitors for use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl[4-(3-cyclopentyloxy-4-methoxyphenyl)pyrrolidine-2-ylidene]acetate; and
(S)-(−)-ethyl [4-(3-cyclopentyloxy-4-methoxyphenyl)pyrrolidine-2-ylidene]acetate.

Most preferred are those PDE4 inhibitors which have an IC$_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an IC$_{50}$ ratio of 0.1 or greater.

Other compounds of interest include:

Compounds set out in U.S. Pat. No. 5,552,438 issued 3 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from Asta Medica (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (IN-SERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vemalis; or T-440 (Tanabe Seiyaku; Fuji, K. et al. J Pharmacol Exp Ther,1998, 284(1): 162), and T2585.

Other possible PDE-4 and mixed PDE3/PDE4 inhibitors include those listed in WO01/13953, the disclosure of which is hereby incorporated by reference.

Phosphodiesterase and Rolipram Binding Assays
Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 µM [³H]cAMP as a substrate (Torphy et al., J. of Biol. Chem., Vol. 267, No. 3 pp 1798-1804, 1992).

Rat brain high speed supernatants were used as a source of protein and both enantiomers of [³H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM MgCl$_2$, 50 µM 5'-AMP and 1 nM of [³H]-rolipram (Torphy et al., J. of Biol. Chem., Vol. 267, No. 3 pp 1798-1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [³H]-cAMP was not present.

Assay Method 1B
Measurement of Phosphodiesterase Activity

PDE activity was assayed using a [³H]cAMP SPA or [³H] cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM MgCl$_2$, 1.7 mM EGTA, [³H]cAMP or [³H] cGMP (approximately 2000 dpm/pmol), enzyme and various concentrations of the inhibitors. The assay was allowed to proceed for 1 hr and was terminated by adding 50 µl of SPA yttrium silicate beads in the presence of zinc sulfate. The plates were shaken and allowed to stand at room temperature for 20 min. Radiolabeled product formation was assessed by scintillation spectrometry.

[³H]R-Rolipram Binding Assay

The [³H]R-rolipram binding assay was performed by modification of the method of Schneider and co-workers, see Nicholson, et al., Trends Pharmacol. Sci., Vol. 12, pp. 19-27 (1991) and McHale et al., Mol. Pharmacol., Vol. 39, 109-113 (1991). R-Rolipram binds to the catalytic site of PDE4 see Torphy et al., Mol. Pharmacol., Vol. 39, pp. 376-384 (1991). Consequently, competition for [³H]R-rolipram binding provides an independent confirmation of the PDE4 inhibitor potencies of unlabeled competitors. The assay was performed at 30° C. for 1 hr in 0.5 µl buffer containing (final concentrations): 50 mM Tris-HCl, pH 7.5, 5 mM MgCl$_2$, 0.05% bovine serum albumin, 2 nM [³H]R-rolipram (5.7×104 dpm/pmol) and various concentrations of non-radiolabeled inhibitors. The reaction was stopped by the addition of 2.5 ml of ice-cold reaction buffer (without [³H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

Suitable anticholinergic agents are those compounds that act as antagonists at the muscarinic receptor, in particular those compounds which are antagonists of the M$_1$ and M$_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as H,-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

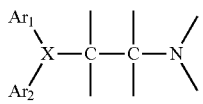

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

Hereinafter, the term "active ingredient" means a compound of formula (I) or (Ia), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration, although the most suitable route may depend upon, for example, the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 μg-10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulisation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

According to a further aspect of the invention, there is provided a process for preparing a compound of formula (I) or (Ia) or a salt, solvate, or physiologically functional derivative thereof which comprises a process as described below followed where necessary or desired by one or more of the following steps in any order:

(i) optional removal of any protecting groups;
(ii) optional separation of an enantiomer or diastereoisomer from a mixture of enantiomers or diastereoisomers;
(iii) optional conversion of the product to a corresponding salt, solvate, or physiologically functional derivative thereof.
(iv) optional conversion of a group $R^{1a}$, $R^{2a}$ and/or $R^{3a}$ to a group $R^1$, $R^2$ and/or $R^3$ respectively.

In one general process (A), a compound of formula (I) or (Ia) may be obtained by deprotection of a protected intermediate, for example of formula (II):

$$R^{13}OCH_2\text{-}[\text{Ar}]\text{-}CH(OR^{19})CH_2NR^{15}CR^4R^5(CH_2)_m\text{-}O\text{-}(CH_2)_n\text{-}OCR^6R^7\text{-}[\text{Ar}'] \quad (II)$$

where the first aryl bears $R^{14}O$ and the second aryl bears $R^{1a}$, $R^{2a}$, $R^{3a}$.

or a salt or solvate thereof, wherein $R^4$, $R^5$, $R^6$, $R^7$, m, and n are as defined for the compound of formula (I) or (Ia), and $R^{1a}$, $R^{2a}$, and $R^{3a}$ are each independently either the same as $R^1$, $R^2$, and $R^3$ respectively as defined for the compound of formulae (I) or (Ia) or a precursor for said group $R^1$, $R^2$, or $R^3$, and $R^{13}$, $R^{14}$, and $R^{15}$ are each independently either hydrogen or a protecting group provided that at least one of $R^{13}$, $R^{14}$, and $R^{15}$ is a protecting group, and $R^{19}$ is hydrogen or a protecting group.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^{13}$ and $R^{14}$ are esters such as acetate ester, aralkyl groups such as benzyl, diphenylmethyl, or triphenylmethyl, and tetrahydropyranyl. Examples of suitable amino protecting groups represented by $R^{15}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as $CHOR^{19}$ using, for example, a trialkylsilyl group such as triethylsilyl. A person skilled in the art will also appreciate other orthogonal protection strategies, available by conventional means as described in Theodora W Greene (see above).

The deprotection to yield a compound of formula (I) or (Ia) may be effected using conventional techniques. It will be apparent to persons skilled in the art that the deprotection method employed should not effect cleavage of the —OCR$^6$R$^7$ moiety.

When $R^{13}$ and/or $R^{14}$ is tetrahydropyranyl this may be cleaved by hydrolysis under acidic conditions, for example using aqueous acetic acid. Acyl groups represented by $R^{15}$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above). In a particular embodiment of the above process, $R^{13}$ and $R^{14}$ may together represent a protecting group as in the compound of formula (III):

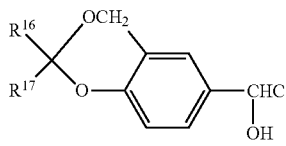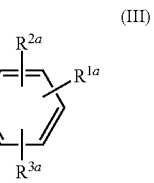

(III)

or a salt or solvate thereof, wherein $R^4$, $R^5$, $R^6$, $R^7$, m, and n are as defined for the compound of formula (I) or (Ia), and $R^{1a}$, $R^{2a}$, and $R^{3a}$ are each independently either the same as $R^1$, $R^2$, and $R^3$ respectively as defined for the compound of formulae (I) or (Ia) or a precursor for said group $R^1$, $R^2$, or $R^3$, $R^{16}$ and $R^{17}$ are independently selected from hydrogen, $C_{1-6}$alkyl, or aryl. In a preferred aspect, both $R^{16}$ and $R^{17}$ are methyl.

A suitable precursor group $R^{1a}$, $R^{2a}$, and/or $R^{3a}$ in the compounds of formulae (II) and (III) would be a group which is convertible to the desired group $R^1$, $R^2$, and/or $R^3$, before, after or simultaneously with the removal of the protecting groups $R^{13}$, $R^{14}$, and/or $R^{15}$. For example, $R^{1a}$, $R^{2a}$, and/or $R^{3a}$ may suitably be a protected version of a group $R^1$, $R^2$, and $R^3$ respectively, such that removal of the protecting group gives the desired group $R^1$, $R^2$, or $R^3$. Preferred protecting groups in $R^{1a}$, $R^{2a}$, and/or $R^{3a}$ are those which may be removed under the conditions used for the removal of the protecting groups $R^{13}$, $R^{14}$, and/or $R^{15}$.

The compound of formula (III) may be converted to a compound of formula (I) or (Ia) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

Compounds of formulae (II) and (III) wherein $R^{15}$ is hydrogen may be prepared from the corresponding compound of formula (IV):

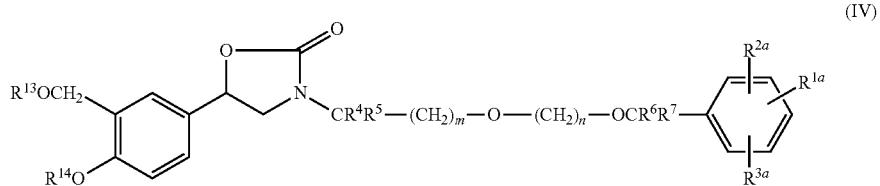

(IV)

or a salt or solvate thereof, wherein $R^4$, $R^5$, $R^6$, $R^7$, $R^{13}$, $R^{14}$, m, and n are as defined for the compound of formula (II) or (III) and $R^{1a}$, $R^{2a}$, and $R^{3a}$ are each independently either the same as $R^1$, $R^2$, and $R^3$ respectively as defined for the compound of formula (II) or (III) or a precursor for said group $R^1$, $R^2$, or $R^3$.

A suitable precursor group $R^{1a}$, $R^{2a}$, and/or $R^{3a}$ in the compound of formula (IV) would be a group which is convertible to the desired group $R^1$, $R^2$, and/or $R^3$. Suitably, such conversions are carried out using conventional methods which are known in the art. For example, where $R^1$ is to be —NR$^8$SO$_2$R$^9$, a suitable precursor group $R^{1a}$ in the compound of formula (IV) would have the amine —NHR$^8$ in place of the substituent R$^1$, such that the desired substituent R$^1$ may be formed by reaction with the appropriate sulphonyl chloride (i.e. R$^9$SO$_2$Cl) before deprotection to form the compound of formula (I).

As a second example, where R$^1$ is to be —NR$^8$C(O)NHR$^9$, a suitable precursor group R$^{1a}$ in the compound of formula (IV) would have the amine —NHR$^8$ in place of the substituent R$^1$, such that the desired substituent R$^1$ may be formed by reaction with the appropriate isocyanate (i.e. R$^9$NCO) before deprotection to form the compound of formula (I). Alternatively, where R$^1$ is to be —NHC(O)NHR$^9$, a suitable precursor group R$^{1a}$ in the compound of formula (IV) has —NO$_2$ in place of the substituent R$^1$ which may be reduced to form the corresponding primary amine before reaction with the isocyanate R$^9$NCO as described above to form the desired urea substituent R$^1$. The reduction of the —NO$_2$ group may be effected by any suitable method such as hydrogenation in the presence of a catalyst, for example, palladium/charcoal or platinum oxide, or by reaction with aluminium amalgam in tetrahydrofuran, or with zinc in ammonium chloride solution.

As a further example, where R$^1$ is to be —NR$^8$C(O)R$^9$, a suitable precursor group R$^{1a}$ in the compound of formula (IV) would have the amine —NHR$^8$ in place of the substituent R$^1$, such that the desired substituent R$^1$ may be formed by reaction with the appropriate acyl chloride (i.e. R$^9$C(O)Cl) before deprotection to form the compound of formula (I).

As a further example, where R$^1$ is to be —NR$^8$C(O)OR$^9$, a suitable precursor group R$^{1a}$ in the compound of formula (IV) would have the amine —NHR$^8$ in place of the substituent R$^1$, such that the desired substituent R$^1$ may be formed by reaction with the appropriate chloroformate (i.e. R$^9$OC(O)Cl) before deprotection to form the compound of formula (I).

Alternatively, where R$^1$ is to be an optionally substituted aryl group, a suitable precursor group R$^{1a}$ in the compound of formula (IV) would have a halo substituent, for example iodo, in place of the substituent R$^1$, such that the desired substituent R$^1$ may be formed by reaction with bis(pinacolato)diboron followed by reaction with the appropriate optionally substituted haloaryl group, before deprotection to form the compound of formula (I). Alternatively, where R$^1$ is to be an optionally substituted aryl group, a suitable precursor group R$^{1a}$ in the compound of formula (IV) would have a halo substituent, for example iodo, in place of the substituent R$^1$, such that the desired substituent R$^1$ may be formed by reaction with the appropriate optionally substituted arylboronic acid, for example an optionally substituted phenylboronic acid, before deprotection to form the compound of formula (I).

Alternatively, R$^{1a}$, R$^{2a}$, and/or R$^{3a}$ may suitably be a protected version of a group R$^1$, R$^2$, and R$^3$ respectively, such that removal of the protecting group gives the desired group R$^1$, R$^2$, or R$^3$. Preferred protecting groups in R$^{1a}$, R$^{2a}$, and/or R$^{3a}$ are those which may be removed under the conditions used for the removal of the protecting groups R$^{13}$ and R$^{14}$, or the conditions used for the conversion of the compound of formula (IV) to the compound of formulae (II) or (III). For example, an —NH— group in the desired group R$^1$, R$^2$, or R$^3$ may be protected by a 2-(trimethylsilyl)ethoxymethyl group or a tert-butoxycarbonyl group.

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

Compounds of formula (IV) may be prepared according to a first method (a) by coupling the corresponding compound of formula (V):

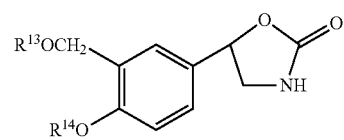

or a salt or solvate thereof, wherein R$^{13}$ and R$^{14}$ are as defined for the compound of formula (IV) with a compound of formula (VI):

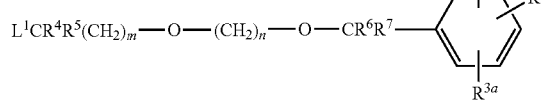

wherein R$^{1a}$, R$^{2a}$, R$^{3a}$, R$^4$, R$^5$, R$^6$, R$^7$, m, and n are as defined for the compound of formula (IV) and L$^1$ is a leaving group, for example a halo group (typically bromo or iodo) or a sulphonate such as an alkyl sulphonate (typically, methanesulphonate), an arylsulphonate (typically, toluenesulphonate), or a haloalkyl sulphonate (typically, trifluoromethanesulphonate).

The coupling of a compound of formula (V) with a compound of formula (VI) may be effected in the presence of a base, such as a metal hydride, for example sodium hydride, an athoride such as potassium t-butoxide or an inorganic base such as caesium carbonate, in an aprotic solvent, for example dimethylformamide.

Compounds of formula (V) may be prepared by ring closure of a compound of formula (VII):

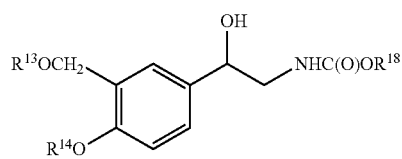

wherein R$^{13}$ and R$^{14}$ are as defined for the compound of formula (V) and R$^{18}$ is C$_{1-6}$alkyl, for example tert-butyl, or aryl, for example phenyl. The ring closure may be effected by treatment with a base, such as a metal hydride, for example sodium hydride, in the presence of an aprotic solvent, for example, dimethylformamide.

Compounds of formula (VII) may be prepared from the corresponding ketone of formula (VIII):

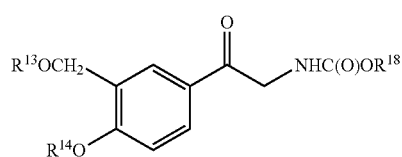

wherein $R^{13}$, $R^{14}$ and $R^{18}$ are as defined for the compound of formula (VII), by reduction by any suitable method, for example by treatment with borane, in the presence of a chiral catalyst, such as CBS-oxazaborolidine, in a suitable solvent such as tetrahydrofuran.

The compound of formula (VIII) may be prepared from the corresponding halide of formula (IX):

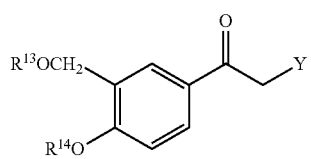

wherein $R^{13}$ and $R^{14}$ are as defined for the compound of formula (VIII) and Y is a halo group, suitably bromo.

The conversion of a compound of formula (IX) to a compound of formula (VIII) may be effected by reaction with the protected amine $HN(COOR^{18})_2$ wherein $R^{18}$ is as defined for the compound of formula (VIII) in the presence of an inorganic base such as caesium carbonate, followed by selective removal of one of the $COOR^{18}$ groups, for example by treatment with an acid such as trifluoroacetic acid.

Compounds of formula (IX) may be prepared from the corresponding compound having free hydroxymethyl and hydroxy substituents by forming the protected groups $R^{13}OCH_2$— and $R^{14}O$— wherein $R^{13}$ and $R^{14}$ are as defined for the compound of formula (IX). Such methods are described in DE 3513885 (Glaxo).

Compounds of formula (VI) may be prepared by coupling a compound of formula (X):

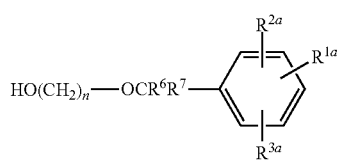

wherein $R^{1a}$, $R^{2a}$, $R^{3a}$, $R^6$, $R^7$, and n are as defined for the compound of formula (VI), with a compound of formula (XI):

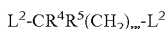

wherein $R^4$, $R^5$, and m are as defined for the compound of formula (VI), and $L^2$ is a leaving group such as halo (typically bromo).

The coupling of compounds (X) and (XI) may be effected in the presence of a base, such as a metal hydride, for example sodium hydride, or an inorganic base such as caesium carbonate, in an aprotic solvent, for example dimethylformamide. Alternatively, the coupling of compounds (X) and (XI) may be effected under phase transfer conditions, suitably in excess aqueous alkali such as 50% aqueous sodium hydroxide, optionally in the presence of a phase transfer catalyst such as a tetrabutylammonium salt, for example tetrabutylammonium bromide.

Compounds of formula (XI) are commercially available or may be prepared by methods well known to the person skilled in the art.

Compounds of formula (X) may be prepared by coupling the corresponding compound of formula (XII):

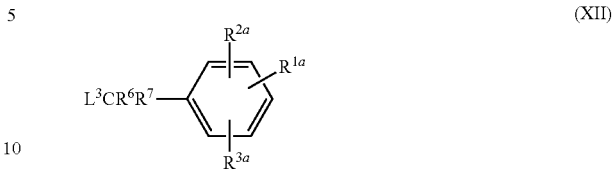

wherein $R^{1a}$, $R^{2a}$, $R^{3a}$, $R^6$, and $R^7$ are as defined for the desired compound of formula (X), and $L^3$ is a leaving group such as halo (typically bromo);

with the dihydroxy compound of formula $HO(CH_2)_nOH$ wherein n is as defined for the compound of formula (X). The coupling of a compound of formula (XII) with the dihydroxy compound may be effected by methods analogous to those described for the coupling of compounds (X) and (XI).

Compounds of formula (XII) are commercially available or may be prepared by methods well known to the person skilled in the art.

According to an alternative process (b), a compound of formula (IV) as defined above may be prepared by coupling the corresponding compound of formula (XIII):

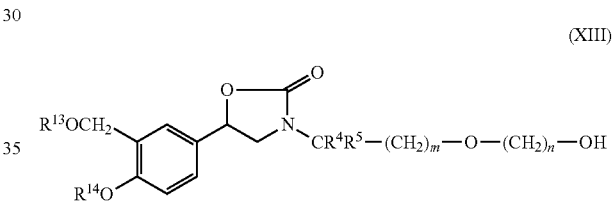

wherein $R^4$, $R^5$, $R^{13}$, $R^{14}$, m, and n are as defined for the desired compound of formula (IV), with the corresponding compound of formula (XII) as defined above in which $R^{1a}$, $R^{2a}$, $R^{3a}$, $R^6$, and $R^7$ are as defined for the desired compound of formula (IV) and $L^3$ is a leaving group such as halo (typically bromo). This coupling may be effected by methods analogous to those described for the coupling of compounds (X) and (XI).

Compounds of formula (XIII) may be prepared by coupling the corresponding compound of formula (V) as defined above wherein $R^{13}$ and $R^{14}$ are as defined for the desired compound of formula (XIII) with the corresponding compound of formula (XIV):

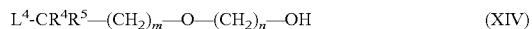

or a protected derivative thereof, wherein $R^4$, $R^5$, m and n are as defined for the desired compound of formula (XIII) and $L^4$ is a leaving group such as halo (typically bromo). The coupling of compounds of formulae (V) and (XIV) may be effected by methods analogous to those described for the coupling of compounds of formulae (X) and (XI).

Compounds of formula (XIV) may be prepared from the corresponding compounds of formula (XI) as defined above with the dihydroxy compound of formula $HO(CH_2)_nOH$ wherein n is as defined for the desired compound of formula (XIV), by methods analogous to those described for the coupling of compounds of formula (X) and (XI).

Alternatively, compounds of formula (XIII) may be prepared by coupling the corresponding compound of formula (XV):

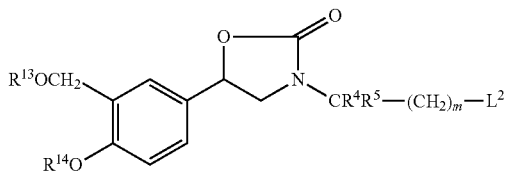

(XV)

wherein $R^{13}$, $R^{14}$, $R^4$, $R^5$, and m are as defined for the desired compound of formula (XIII) and $L^2$ is a leaving group such as halo (typically bromo), followed by coupling the compound of formula (XV) with the dihydroxy compound of formula $HO(CH_2)_nOH$, wherein n is as defined for the desired compound of formula (XIII), by methods analogous to those described for the coupling of compounds of formula (X) and (XI).

The compound of formula (XV) may be prepared by coupling the corresponding compound of formula (V) as previously defined wherein $R^{13}$ and $R^{14}$ are as defined for the desired compound of formula (XIII), with the corresponding compound of formula (XI) as previously defined wherein $R^4$, $R^5$, and m are as defined for the desired compound of formula (XIII) and $L^2$ is a leaving group such as halo (typically bromo).

The coupling of compounds of formulae (V) and (XI) may be effected by methods analogous to those described for the coupling of compounds of formulae (V) and (VI).

In a further alternative process (c) compounds of formula (IV) as defined above may be prepared by coupling the corresponding compound of formula (XVI):

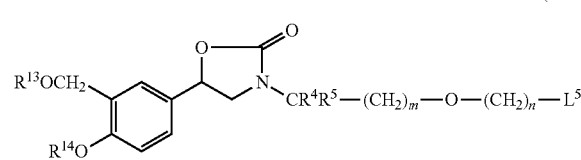

(XVI)

wherein $R^{13}$, $R^{14}$, $R^4$, $R^5$, m and n are as defined for the compound of formula (IV) and $L^5$ is a leaving group, for example a sulphonate such as an alkyl sulphonate (typically, methanesulphonate), an arylsulphonate (typically, toluenesulphonate), or a haloalkyl sulphonate (typically, trifluoromethanesulphonate), with a compound of formula (XVII):

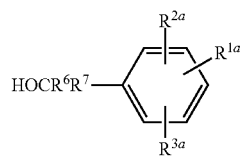

(XVII)

wherein $R^{1a}$, $R^{2a}$, $R^{3a}$, $R^6$, and $R^7$ are as defined for the compound of formula (IV).

The coupling of compounds of formulae (XVI) and (XVII) may be effected by methods analogous to those described for the coupling of compounds of formulae (V) and (VI).

The compound of formula (XVI) may be prepared by converting the hydroxyl group in a compound of formula (XIII) into a leaving group $L^4$ such as a methansulphonate group using methods known in the art, for example by reaction with methanesulphonyl chloride in the presence of a suitable base, for example $NEt(^iPr)_2$, in a suitable solvent such as dichloromethane.

The compounds of formula (XVII) are commercially available or may be prepared using methods known in the art.

During the synthesis of the compound of formula (XIII), appropriate protecting chemistry may be used, for example, the compounds of formula (XIV) and the dihydroxy compound of formula $HO(CH_2)_nOH$ may be protected so as to improve the yield of the desired intermediates. Suitable protecting strategies will be appreciated by the person skilled in the art and may also be found in Theodora W. Greene (see above). Thus, for example, a primary hydroxyl group may be protected with a trialkylsilyl group such as tert-butyldimethylsilyl or with a benzyl group.

In a further process (d) compounds of formula (IV) as defined above may be prepared by coupling a compound of formula (XVIII):

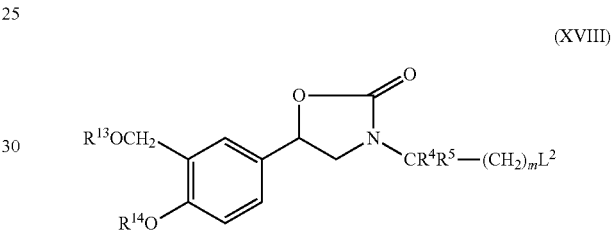

(XVIII)

wherein $R^{13}$, $R^{14}$, $R^4$, $R^5$, and m are as defined for formula (IV) and $L^2$ is defined as for formula (XI),
with a compound of formula (X) as defined above. The reaction of compounds (XVIII) and (X) may be effected in a similar manner to the coupling of compounds (XI) and (X).

Compounds of formula (XVIII) may be prepared by reacting a compound of formula (V) with a compound of formula (XI) in a similar manner to the reaction of compounds (V) and (XIV).

In a further general process (B) a compound of formula (I) and (Ia) may be obtained by alkylation of an amine of formula (XIX):

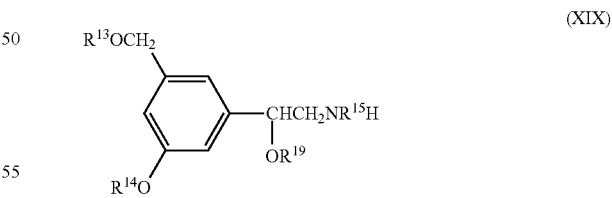

(XIX)

wherein $R^{13}$, $R^{14}$, $R^{15}$ and $R^{19}$ are as hereinbefore defined,
with a compound of formula (VI) wherein $L^1$ represents a leaving group such as halo (typically bromo), followed by removal of any protecting groups present by conventional methods as described above for the deprotection of compounds of formula (II).

The reaction of compounds of formulae (XIX) and (VI) may be optionally effected in the presence of an organic base, such as a trialkylamine, for example diisopropyl ethylamine, and in a suitable solvent, for example dimethyformamide.

Compounds of formula (XIX) are known in the art, for example EP-A-0947498, or may readily be prepared by a person skilled in the art.

In a yet further general process (C), a compound of formula (I) or (Ia) may be prepared by reacting an amine of formula (XIX) as defined hereinabove, with a compound of formula (XX):

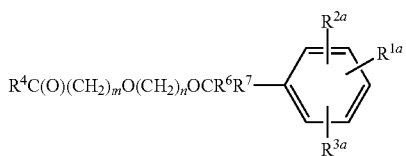

(XX)

wherein $R^4$, $R^6$, $R^7$, $R^{1a}$, $R^{2a}$, $R^{3a}$, m and n are as hereinbefore defined;

under conditions suitable to effect reductive amination, for example in the presence of a reducing agent such as borohydride, typically tetramethylammonium(triacetoxy) borohydride.

A compound of formula (XX) may be prepared by methods known in the art, for example from a compound of formula (VI) as defined hereinabove via Kornblum oxidation.

It will be appreciated that in any of the general processes (A), (B) or (C) as well as the processes for (a) to (d) for preparing compounds (IV) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. It will also be appreciated that in general processes (B) and (C) appropriate protecting groups may be employed if necessary and/or desired and removed at any suitable stage of the synthesis, eg. in the last stage, as described in general process (A).

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described herein.

Optional conversion of a compound of formula (I) or (Ia) to a corresponding salt may conveniently be effected by reaction with the appropriate acid or base. Optional conversion of a compound of formula (I) or (Ia) to a corresponding solvate or physiologically functional derivative may be effected by methods known to those skilled in the art.

According to a further aspect, the present invention provides novel intermediates for the preparation of compounds of formula (I) or (Ia), for example:
compounds of formula (II) and (III) as defined above, or an optical isomer, a salt, or a protected derivative thereof; particularly, a compound selected from:
N-[3-({2-[(6-{[(2R)-2-(2,2-dimethyl-4H-1,3-benzodioxin-6-yl)-2-hydroxyethyl]amino}hexyl)oxy]ethoxy}methyl)phenyl]-N'-phenylurea; and
(1R)-2-[(6-{2-[(2,6-dichlorobenzyl)oxy]ethoxy}hexyl)amino]-1-(2,2-dimethyl-4H-1,3-benzodioxin-6-yl)ethanol;
N-cyclohexyl-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea;
N-(1,1'-biphenyl-4-yl)-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea;
N-cyclopropyl-3'-[(2-[(6-{[(2R)-2-(2,2-dimethyl-4H-1,3-benzodioxin-6-yl)-2-hydroxyethyl]amino}hexyl)oxy]ethoxy)methyl]-1,1'-biphenyl-2-sulfonamide;
(1R)-2-{[6-(2-[{3-(2,3-dihydroimidazo[2,1-b][1,3]thiazol-6-ylmethyl)amino]-phenyl}methoxy]ethoxy)hexyl]amino}-1-(2,2-dimethyl-4H-1,3-benzodioxin-6-yl)ethanol;
N-{3-[(2-[(6-{[(2R)-2-(2,2-dimethyl-4H-1,3-benzodioxin-6-yl)-2-hydroxyethyl]-amino}hexyl)oxy]ethoxy)methyl]phenyl}-3-[(phenylsulfonyl)amino]benzamide;
N-(3-{[({3-[(2-[(6-{[(2R)-2-(2,2-dimethyl-4H-1,3-benzodioxin-6-yl)-2-hydroxy-ethyl]amino}hexyl)oxy]ethoxy)methyl]phenyl}amino)carbonyl]amino}phenyl)-pyridine-3-carboxamide;
N-cyclohexyl-3-[(2-[(6-{[(2R)-2-(2,2-dimethyl-4H-1,3-benzodioxin-6-yl)-2-hydroxyethyl]amino}hexyl)oxy]ethoxy)methyl]-N-({[2-(trimethylsilyl)ethyl]-oxy}methyl)benzenesulfonamide;
3'-[(2-[(6-{[(2R)-2-(2,2-dimethyl-4H-1,3-benzodioxin-6-yl)-2-hydroxyethyl]-amino}hexyl)oxy]ethoxy)methyl]-1,1'-biphenyl-3-ol;
(1R)-1-(2,2-dimethyl-4H-1,3-benzodioxin-6-yl)-2-[(6-{2-[(3-iodobenzyl)oxy]-ethoxy}hexyl)amino]ethanol;
N-{3-[(2-{[6-({(2R)-2-Hydroxy-2-[4-hydroxy-3-(hydroxymethyl)phenyl]ethyl}-amino)hexyl]oxy}ethoxy)methyl]phenyl}-N'-[3-(phenylethynyl)phenyl]urea;
(1R)-2-{[6-(2-{[3'-{2,4-bis[(1,1-dimethylethyl)oxy]pyrimidin-5-yl}-1,1'-biphenyl-3-yl]methoxy}ethoxy)hexyl]amino}-1-(2,2-dimethyl-4H-1,3-benzodioxin-6-yl)ethanol; and
cyclopentyl 3-[(2-[(6-{[(2R)-2-(2,2-dimethyl-4H-1,3-benzodioxin-6-yl)-2-hydroxy-ethyl]amino}hexyl)oxy]ethoxy)methyl]phenylcarbamate;
and other similar intermediates exemplified hereinafter;
compounds of formula (IV) as defined above, or an optical isomer, a salt, or a protected derivative thereof; particularly, a compound selected from:
(5R)-3-(6-{2-[(2,6-dichlorobenzyl)oxy]ethoxy}hexyl)-5-(2,2-dimethyl-4H-1,3-benzodioxin-6-yl)-1,3-oxazolidin-2-one;
(5R)-5-(2,2-dimethyl-4H-1,3-benzodioxin-6-yl)-3-(6-{2-[(3-nitrobenzyl)oxy]-ethoxy}hexyl)-1,3-oxazolidin-2-one;
N-(3-{[2-({6-[(5R)-5-(2,2-Dimethyl-4H-1,3-benzodioxin-6-yl)-2-oxo-1,3-oxazolidin-3-yl]hexyl}oxy)ethoxy]methyl}phenyl)-N'-phenylurea;
N-cyclohexyl-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea;
N-(1,1'-biphenyl-4-yl)-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea;
(5R)-3-(6-{2-[(3-aminobenzyl)oxy]ethoxy}hexyl)-5-(2,2-dimethyl-4H-1,3-benzodioxin-6-yl)-1,3-oxazolidin-2-one;
(5R)-5-(2,2-dimethyl-4H-1,3-benzodioxin-6-yl)-3-{6-[2-{[(3-nitrophenyl)-methyl]oxy}ethoxy]hexyl}-1,3-oxazolidin-2-one;
N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-3-[(phenylsulfonyl)amino]-benzamide;

3-amino-N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]benzamide;

N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-3-nitrobenzamide;

N-(3-aminophenyl)-N'-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]urea;

N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-N'-(3-nitrophenyl)urea;

N-cyclohexyl-3-({2-({6-[(5R)-5-(2,2-dimethyl-4H-1,3-benzodioxin-6-yl)-2-oxo-1,3-oxazolidin-3-yl]hexyl}oxy)ethoxy}methyl)-N-({[2-(trimethylsilyl)ethyl]oxy}-methyl)benzenesulfonamide;

N-{3-[({[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]amino}carbonyl)amino]-phenyl}pyridine-3-carboxamide;

cyclopentyl 3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenylcarbamate;

N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-N'-[3-(phenylethynyl)phenyl]urea;

1,1-dimethylethyl cyclopropyl{[3'-({2-({6-[(5R)-5-(2,2-dimethyl-4H-1,3-benzodioxin-6-yl)-2-oxo-1,3-oxazolidin-3-yl]hexyl}oxy)ethoxy}methyl)-1,1'-biphenyl-2-yl]sulfonyl}carbamate;

(5R)-5-(2,2-dimethyl-4H-1,3-benzodioxin-6-yl)-3-(6-{2-([3-(4,4,5,5-tetramethyl-1,3,2-dioxaborolan-2-yl)phenyl]methoxy)ethoxy}hexyl)-1,3-oxazolidin-2-one;

(5R)-3-[6-(2-[{3-[(2,3-dihydroimidazo[2,1-b][1,3]thiazol-6-ylmethyl)amino]-phenyl}methoxy]ethoxy)hexyl]-5-(2,2-dimethyl-4H-1,3-benzodioxin-6-yl)-1,3-oxazolidin-2-one;

(5R)-5-(2,2-dimethyl-4H-1,3-benzodioxin-6-yl)-3-{6-[2-{(3-iodophenyl)methoxy}ethoxy]hexyl}-1,3-oxazolidin-2-one;

(5R)-5-(2,2-dimethyl-4H-1,3-benzodioxin-6-yl)-3-{6-[2-{(3'-hydroxy-1,1'-biphenyl-3-yl)methoxy}ethoxy]hexyl}-1,3-oxazolidin-2-onel; and (5R)-3-{6-[2-{(3'-{2,4-bis[(1,1-dimethylethyl)oxy]pyrimidin-5-yl}-1,1'-biphenyl-3-yl)methoxy}ethoxy]hexyl}-5-(2,2-dimethyl-4H-1,3-benzodioxin-6-yl)-1,3-oxazolidin-2-one;

and other similar intermediates exemplified hereinafter;

compounds of formula (XIII) as defined above, or an optical isomer, a salt, or a protected derivative thereof; particularly, the compound:

(5R)-5-(2,2-dimethyl-4H-1,3-benzodioxin-6-yl)-3-[6-(2-hydroxyethoxy)hexyl]-1,3-oxazolidin-2-one, and other similar intermediates exemplified hereinafter.

For a better understanding of the invention, the following Examples are given by way of illustration.

SYNTHETIC EXAMPLES

Throughout the examples, the following abbreviations are used:
LCMS: Liquid Chromatography Mass Spectrometry
MS: mass spectrum
TSP+ve: thermospray mass spectrum positive mode
SPE: solid phase extraction
XRPD-x-ray powder diffraction
RT: retention time
THF: tetrahydofuran
DMF: N,N-dimethylformamide
EtOAc: ethyl acetate
EtOH: ethanol
MeOH: methanol
MIBK: methyl-isobutylketone
PE: petroleum ether 40°-60°
HPLC: high performance liquid chromatography
TLC: thin layer chromatography
Sat: saturated
bp: boiling point
ca: circa
h: hour(s)
min: minute(s)
d: doublet
dd: double doublet
s: singlet
brs: broad singlet All temperatures are given in degrees centigrade.
Ammonia refers to 0.880 (aqueous) ammonia.
Silica gel refers to Merck silica gel 60 Art number 7734.
Flash silica gel refers to Merck silica gel 60 Art number 9385.
Biotage refers to prepacked silica gel cartridges containing KP-Sil run on flash 12i chromatography module.
Bond Elut are prepacked cartridges used in parallel purifications, normally under vacuum. These are commercially available from Varian.
SCX refers to prepacked SPE cartridges containing benzenesulphonic acid ion exchange resin.
Preparative thin layer chromatography was carried out on silica gel, 20×20 cm, Whatman PK6F, 60 A, 1 mm thick.
LC was conducted on a Luna 3 μm C18(2) column (50 mm×2 mm id) eluting with 0.05% v/v trifluoroacetic acid in water (solvent A) and 0.05% v/v trifluoroacetic acid in acetonitrile (solvent B) using the elution gradient 0-8.0 min 0% B-95% B, 8.0-8.01 min 95% B-0% B, with a flow rate of 1 mL/min with a column temperature of 40° C.
LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).
HPLC was conducted using the same chromatographic system as for the LCMS.
The XRPD analysis shown in the Figures were performed on a Phillips X pert Prop powder diffractometer, Model PW3040/60, serial number DY1379. The method runs from 2 to 45 degrees 2Theta with 0.02 degree 2Theta step size and a 2 second collection time at each step.

Example 1

Synthesis of N-{3-[(2-{[6-({(2R)-2-hydroxy-2-[4-hydroxy-3-(hydroxymethyl)-phenyl]ethyl}amino)hexyl]oxy}ethoxy)methyl]phenyl}-N'-phenylurea acetate i) Di(tert-butyl)2-(2,2-dimethyl-4H-1,3-benzodioxin-6-yl)-2-oxoethylimidodicarbonate Caesium carbonate (70.4 g) was added to a stirred suspension of 2-bromo-1-(2,2-dimethyl-4H-1,3-benzodioxin-6-yl)

ethanone, (Glaxo, DE 3513885, 1985) (61.8 g) and di-t-butyl iminodicarboxylate (47.15 g) in acetonitrile (600 ml) under nitrogen. After vigorous stirring at 21° for 24 h the mixture was diluted with water (ca800 ml) and the product was extracted with diethyl ether (1 liter, then 200 ml). The combined organic layers were washed with brine, dried ($MgSO_4$) and concentrated to ca400 ml. The white crystals were collected by filtration, washed with diethyl ether and dried to give the title compound (24.4 g) δ ($CDCl_3$) 7.78(1H, dd, J 8, 2 Hz), 7.65 (1H, brs), 6.87(1H, d, J 8 Hz), 4.97(2H, s), 4.88(2H, s), 1.56(6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

ii) tert-Butyl 2-(2,2-dimethyl-4H-1,3-benzodioxin-6-yl)-2-oxoethylcarbamate

Trifluoroacetic acid (92 ml) was added to a stirred solution of di(tert-butyl)2-(2,2-dimethyl-4H-1,3-benzodioxin-6-yl)-2-oxoethylimidodicarbonate, (352.55 g) in dichloromethane (3.6 liters) at 21° and the reaction was stirred for 1.5 h. Aqueous NaOH solution (1.75 liters) was added and after 10 min the phases were separated. The organic layer was washed with water, dried ($MgSO_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% EtOAc in hexane. LCMS RT=3.37 min.

iii) tert-Butyl(2R)-2-(2,2-dimethyl-4H-1,3-benzodioxin-6-yl)-2-hydroxyethylcarbamate A 2M solution of borane-dimethyl sulphide in THF (28 ml) was added slowly to a 1M solution of (R)-tetrahydro-1-methyl-3,3-diphenyl-1H,3H-pyrrolo[1,2-c][1,3,2]oxazaborole in toluene (56 ml) at 0° under nitrogen. A solution of tert-butyl 2-(2,2-dimethyl-4H-1,3-benzodioxin-6-yl)-2-oxoethylcarbamate, (108.2 g) in THF (1.3 liters) was added slowly keeping the temperature below 5° followed by 2M solution of borane-dimethyl sulphide in THF (252 ml) over 50 min. After 1 h, 2M HCl (170 ml) was added with cooling and the mixture was partitioned between EtOAc and water. The organic layer was washed with saturated $NaHCO_3$ solution and brine and dried ($MgSO_4$). The solution was concentrated and the product purified by chromatography on flash silica gel (800 g), eluting successively with hexane:EtOAc (4:1 then 3:1) to give the title compound (93.3 g), LCMS RT=3.31 min.

iv) (5R)-5-(2,2-Dimethyl-4H-1,3-benzodioxin-6-yl)-1,3-oxazolidin-2-one tert-Butyl(2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° under nitrogen. The mixture was stirred at 21° for 2 h. The mixture was recooled to 0° and 2M HCl (134 ml) was added. The mixture was diluted with water and the product was extracted with EtOAc twice. The solution was washed with brine twice, dried ($MgSO_4$) and evaporated to give the title compound (63.55 g). LCMS RT=2.66 min.

v) 2-{[tert-Butyl(dimethyl)silyl]oxy}ethanol

Ethylene glycol (2.00 g) in anhydrous THF (60 ml) under nitrogen was treated portionwise with sodium hydride (60% dispersion in mineral oil, 1.29 g) and the mixture stirred at 20° C. for 45 min. Tert-butyl dimethylsilyl chloride (4.86 g) was added and the mixture stirred at 20° C. for 45 min. Phosphate buffer (60 ml, pH6.5) was added and the mixture stirred for 20 min before extracting with ether (60 ml). The organic layer was then washed with water (60 ml) and brine (60 ml), before drying over $Na_2SO_4$, filtering, and removing the solvent in vacuo. This was purified by flash chromatography on silica. Elution with 1:4 EtOAc/cyclohexane followed by solvent evaporation in vacuo gave the title compound (3.82 g). TSP+ve 194 $MNH_{4+}$.

vi) {2-[(6-Bromohexyl)oxy]ethoxy}(tert-butyl)dimethylsilane

2-{[tert-Butyl(dimethyl)silyl]oxy}ethanol (1.82 g), 1,6-dibromohexane (7.56 g) and tetrabutylammonium bromide (0.067 g) were stirred under nitrogen and treated with 50% w/v sodium hydroxide (2 g in 4 ml). The mixture was stirred vigorously at 20° C. for 5 days. Water (100 ml) was added, and the product extracted with dichloromethane (3×50 ml). The combined organic layer was separated and dried over $Na_2SO_4$ before filtering. The solvent was evaporated in vacuo to give a residue which was purified by flash chromatography on silica. Elution with 5% ether/cyclohexane followed by solvent evaporation in vacuo gave the title compound (2.35 g). LCMS RT=4.32 min, ES+ve 339 $(MH)^+$.

vii) (5R)-3-[6-(2-{[tert-Butyl(dimethyl)silyl]oxy}ethoxy)hexyl]-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-1,3-oxazolidin-2-one (0.83 g) in DMF (20 ml) was treated with sodium hydride (60% dispersion in mineral oil, 0.20 g) and the mixture stirred under nitrogen at 20° C. for 30 min. A solution of {2-[(6-bromohexyl)oxy]ethoxy}tert-butyl)dimethylsilane (1.47 g) in DMF (4 ml) was added and the mixture stirred at 20° C. for 90 min. Phosphate buffer (20 ml, pH6.5) was added, before partitioning between EtOAc (50 ml) and water (50 ml). The layers were separated and the aqueous layer re-extracted with EtOAc (3×30 ml). The combined organic layer was washed with water (3×50 ml) and dried over $Na_2SO_4$ before filtering. Solvent evaporation in vacuo gave a residue which was purified by flash chromatography on silica. Elution with EtOAc-cyclohexane (1:1) followed by solvent evaporation in vacuo gave the title compound (0.84 g). LCMS RT=4.11 min, ES+ve 507 $(MH)^+$.

viii) (5R)-5-(2,2-Dimethyl-4H-1,3-benzodioxin-6-yl)-3-[6-(2-hydroxyethoxy)hexyl]-1,3-oxazolidin-2-one A solution of (5R)-3-[6-(2-{[tert-butyl(dimethyl)silyl]oxy}ethoxy)hexyl]-5-(2,2-dimethyl-4H-1,3-benzodioxin-6-yl)-1,3-oxazolidin-2-one (0.79 g) in THF (30 ml) was treated with tetrabutylammonium fluoride on silica gel (3.08 g) and the mixture stirred under nitrogen at 20° C. for 2.75 h. The reaction mixture was filtered and the filtrate evaporated in vacuo to give a residue which was purified by SPE on silica.

Elution with dichloromethane, then EtOAc followed by solvent evaporation in vacuo gave the title compound (0.56 g). LCMS RT=3.05 min, ES+ve 394 (MH)+.

ix) (5R)-5-(2,2-Dimethyl-4H-1,3-benzodioxin-6-yl)-3-(6-{2-[(3-nitrobenzyl)oxy]-ethoxy}hexyl)-1,3-oxazolidin-2-one A solution of (5R)-5-(2,2-dimethyl-4H-1,3-benzodioxin-6-yl)-3-[6-(2-hydroxyethoxy)hexyl]-1,3-oxazolidin-2-one (0.20 g) in DMF (5 ml) was treated with sodium hydride (60% dispersion in mineral oil, 0.030 g) and the mixture stirred under nitrogen at 20° C. for 15 min. 3-nitrobenzylbromide (0.11 g) was added, and the mixture stirred at 20° C. for a further 3 h. Phosphate buffer (20 ml, pH6.5) was added and the mixture was stirred for 5 min before extracting with EtOAc (3×20 ml). The organic layer was washed with water (3×20 ml), dried over $Na_2SO_4$ and filtered. Solvent evaporation gave the crude product which was purified by flash chromatography on silica. Elution with EtOAc-cyclohexane (7:3) followed by solvent evaporation in vacuo gave the title compound (0.10 g). LCMS RT=3.61 min, ES+ve 529 (MH)+.

x) (5R)-3-(6-{2-[(3-Aminobenzyl)oxy]ethoxy}hexyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-(6-{2-[(3-nitrobenzyl)oxy]ethoxy}hexyl)-1,3-oxazolidin-2-one (0.10 g) in EtOH (3 ml) and EtOAc (3 ml) was hydrogenated for 19.5 h over platinum oxide (0.020 g). The mixture was filtered through celite, and the solvent evaporated in vacuo to give a residue which was purified by flash chromatography on silica. Elution with EtOAc-cyclohexane (8:2) followed by solvent evaporation in vacuo gave the title compound (0.057 g). LCMS RT=3.43 min, ES+ve 499 (MH)+.

xi) N-(3-{[2-({6-[(5R)-5-(2,2-Dimethyl-4H-1,3-benzodioxin-6-yl)-2-oxo-1,3-oxazolidin-3-yl]hexyl}oxy)ethoxy]methyl}phenyl)-N'-phenylurea A solution of (5R)-3-(6-{2-[(3-aminobenzyl)oxy]ethoxy}hexyl)-5-(2,2-dimethyl-4H-1,3-benzodioxin-6-yl)-1,3-oxazolidin-2-one (0.057 g) in dichloromethane (2 ml) was treated with phenyl isocyanate (0.020 g) and the mixture stirred under nitrogen at 20° C. for 2 h. Isopropanol (5 ml) was added to quench excess isocyanate, and the mixture stirred for 30 min before leaving to stand for 15 h. The solvents were removed in vacuo to give a residue which was purified by SPE. Elution with a stepped gradient of eluants from cyclohexane to cyclohexane-EtOAc (9:1) and onwards to EtOAc followed by solvent evaporation in vacuo gave the title compound (0.062 g). LCMS RT=3.70 min, ES+ve 618 (MH)+.

xii) N-[3-({2-[(6-{[(2R)-2-(2,2-Dimethyl-4H-1,3-benzodioxin-6-yl)-2-hydroxyethyl]amino}hexyl)oxy]ethoxy}methyl)phenyl]-N'-phenylurea Potassium trimethylsilanolate (0.056 g) was added to a solution of N-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)-N'-phenylurea (0.061 g) in degassed anhydrous THF (4 ml) whilst stirring under nitrogen. The reaction mixture was heated to 65° C. for 4 h, adding additional potassium trimethylsilanolate (0.057 g) and heating for a further 2.5 h, at which point the reaction mixture was cooled to room temperature. Phosphate buffer (20 ml, pH6.5) was added and the mixture extracted with EtOAc (3×20 ml). The combined organic layers were separated and dried over $Na_2SO_4$ before filtering. Solvent evaporation in vacuo gave the title compound (0.027 g). LCMS RT=2.80 min, ES+ve 592 (MH)+.

xiii) N-{3-[(2-{[6-({(2R)-2-Hydroxy-2-[4-hydroxy-3-(hydroxymethyl)phenyl]ethyl}-amino)hexyl]oxy}ethoxy)methyl]phenyl}-N'-phenylurea acetate A solution of N-[3-({2-[(6-{[(2R)-2-(2,2-dimethyl-4H-1,3-benzodioxin-6-yl)-2-hydroxyethyl]amino}hexyl)oxy]ethoxy}methyl)phenyl]-N'-phenylurea (0.025 g) in acetic acid (1 ml) and water (0.5 ml) were stirred under nitrogen at 70° C. for 75 min. The reaction mixture was cooled to room temperature before concentrating under vacuum and azeotroping with MeOH (2×10 ml) to give the title compound (0.028 g). LCMS RT=2.50 min, ES+ve 552 (MH)+.

Example 2

Alternative synthesis of (5R)-5-(2,2-dimethyl-4H-1,3-benzodioxin-6-4-3-{6-[2-hydroxyethoxy]hexyl}-1,3-oxazolidin-2-one i) [(2-[(6-Bromohexyl)oxy]ethoxy)methyl]benzene A solution of 2-(benzyloxy)ethanol (2.00 g) and tetrabutylammonium bromide (84 mg) in 1,6-dibromohexane (6.06 ml) was treated with 50% w/v sodium hydroxide solution (5.0 ml) and the mixture was vigorously stirred for 18 h at 20°. Water (50 ml) was added and the mixture was extracted with dichloromethane (40 ml). The organic extract was dried ($Na_2SO_4$) and the solvent evaporated in vacuo to give a residue which was purified by flash chromatography on silica gel. Elution with EtOAc-PE (1:9) gave the title compound (2.87 g). LCMS RT=3.94 min, ES+ve 337 (MNa)+, 339 (MNa)+ ii) 2-[(6-Bromohexyl)oxy]ethanol

A solution of [(2-[(6-bromohexyl)oxy]ethoxy)methyl]benzene (1.5 g) in EtOAc (20 ml) and EtOH (20 ml) was hydrogenated over 10% palladium on carbon (200 mg). After 2 h the mixture was filtered through celite and the filtrate evaporated in vacuo to give the title compound (1.05 g). TSP+ve 242 $(MNH_4)^+$, 244 $(MNH_4)^+$ iii) 5R)-5-(2,2-Dimethyl-4H-1,3-benzodioxin-6-yl)-3-{6-[2-hydroxyethoxy]-hexyl}-1,3-oxazolidin-2-one A solution of (5R)-5-(2,2-dimethyl-4H-1,3-benzodioxin-6-yl)-1,3-oxazolidin-2-one (1.067 g) in DMF (10 ml) under nitrogen was treated with sodium hydride (60% dispersion in mineral oil, 222 mg) and the mixture was stirred at 20° for 15 min. A solution of 2-[(6-bromohexyl)oxy]ethanol (1.157 g) in DMF (1 ml) was added and the mixture was stirred at 20° for 3.5 h. Phosphate buffer solution (pH 6.5, 20 ml) and water (30 ml) were added. The mixture was extracted with EtOAc (2×20 ml) and the combined extracts were washed with water (30 ml) and dried ($Na_2SO_4$). Solvent evaporation in vacuo gave a residue which was purified by flash chromatography on silica gel. Elution with MeOH-EtOAc (1:9) gave the title compound (1.42 g). LCMS RT=2.90 min, ES+ve 394 (MH)+.

Example 3

Alternative synthesis of (5R)-5-(2,2-dimethyl-4H-1,3-benzodioxin-6-4-3-{6-[2-hydroxyethoxy]hexyl}-1,3-oxazolidin-2-one i) (5R)-3-(6-Bromohexyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-1,3-oxazolidin-2-one (5.00 g) and 1,6-dibromohexane (9.26 ml) in DMF (50 ml) at 0° under nitrogen was treated in three equal portions with sodium hydride (60% dispersion in mineral oil, 963 mg). The mixture was stirred at 0° for 30 min and then at 20° for a further 2.5 h. Phosphate buffer solution (pH 6.5, 50 ml) and water (150 ml) were added and the mixture was extracted with diethyl ether (2×150 ml). The combined extracts were washed with water (2×150 ml) and were dried ($Na_2SO_4$). The solvent was evaporated in vacuo and the residue was purified by flash chromatography on silica gel. Elution with MeOH-dichloromethane (1:4) gave the title compound (7.10 g). LCMS RT=3.52 min, ES+ve 412 (MH)$^+$, 414 (MH)$^+$.

ii) (5R)-5-(2,2-Dimethyl-4H-1,3-benzodioxin-6-yl)-3-{6-[2-hydroxyethoxy]hexyl}-1,3-oxazolidin-2-one A solution of ethylene glycol (5.00 ml) in DMF (40 ml) under nitrogen at 0° was treated portionwise with sodium hydride (60% dispersion in mineral oil, 1.292 g) and the mixture was stirred at 0° for 15 min. A solution of (5R)-3-(6-bromohexyl)-5-(2,2-dimethyl-4H-1,3-benzodioxin-6-yl)-1,3-oxazolidin-2-one (7.40 g) in DMF (10 ml) was added. The mixture was stirred at 0° for 0.5 h then at 20° for 3 h. Phosphate buffer solution (pH 6.5, 40 ml) and water (160 ml) were added and the mixture was extracted with EtOAc (2×100 ml). The combined extracts were washed with water (2×150 ml), brine (50 ml) and were dried ($Na_2SO_4$). The solvent was evaporated in vacuo and the residue was purified by flash chromatography on silica gel. Elution with MeOH-EtOAc (1:9) gave the title compound (4.10 g). LCMS RT=2.90 min, ES+ve 394 (MH)$^+$.

Example 4

Synthesis of 4-{(1R)-2-[(6-{2-[(2,6-dichlorobenzyl)oxy]ethoxy}hexyl)amino]-1-hydroxyethyl}-2-(hydroxymethyl)phenol acetate i) (5R)-3-(6-{2-[(2,6-Dichlorobenzyl)oxy]ethoxy}hexyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-[6-(2-hydroxyethoxy)hexyl]-1,3-oxazolidin-2-one (200 mg) in DMF (4 ml) under nitrogen was treated with sodium hydride (26 mg, 60% in oil) and the mixture was stirred at 20° for 10 min. 2,6-Dichlorobenzyl bromide (122 mg) was added and the mixture was stirred at 20° for 3 h. Phosphate buffer solution (20 ml, pH6.5) was added and the mixture was extracted with EtOAc (30 ml). The extract was washed with water (2×20 ml), dried ($NaSO_4$) and the solvent evaporated in vacuo to give a residue. The residue was purified by chromatography on flash silica gel 20 mm diameter column. Elution with EtOAc-cyclohexane (1:1) gave the title compound (155 mg). LCMS RT=3.97 min.

ii) (1R)-2-[(6-{2-[(2,6-Dichlorobenzyl)oxy]ethoxy}hexyl)amino]-1-(2,2-dimethyl-4H-1,3-benzodioxin-6-yl)ethanol A solution of (5R)-3-(6-{2-[(2,6-dichlorobenzyl)oxy]ethoxy}hexyl)-5-(2,2-dimethyl-4H-1,3-benzodioxin-6-yl)-1,3-oxazolidin-2-one (140 mg) in THF (7 ml) under nitrogen was treated with potassium trimethylsilanolate (130 mg) and the mixture was heated (oil bath temperature 80°) with stirring for 3 h. The mixture was cooled to 20° and was partitioned between phosphate buffer solution (20 ml, pH6.5) and EtOAc (20 ml). The organic phase was separated, dried ($NaSO_4$) and the solvent evaporated in vacuo to give the title compound (130 mg). LCMS RT=3.00 min.

iii) 4-{(1R)-2-[(6-{2-[(2,6-Dichlorobenzyl)oxy]ethoxy}hexyl)amino]-1-hydroxyethyl}-2-(hydroxymethyl)phenol acetate A solution of (1R)-2-[(6-{2-[(2,6-dichlorobenzyl)oxy]ethoxy}hexyl)amino]-1-(2,2-dimethyl-4H-1,3-benzodioxin-6-yl)ethanol (130 mg) in acetic acid (2 ml) and water (1 ml) was heated (oil bath temperature 80°) with stirring for 30 min. The mixture was cooled to 20° and the solvent was evaporated in vacuo. The residue was azeotroped in vacuo with MeOH (2×1 ml) to give the title compound (135 mg). LCMS RT=2.57 min, ES+ve 486 (MH)$^+$, 488 (MH)$^+$, 490 (MH)$^+$.

Example 5

Synthesis of N-(1,1'-biphenyl-4-yl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea i) N-(1,1'-Biphenyl-4-yl)-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea A solution of (5R)-3-(6-{2-[(3-aminobenzyl)oxy]ethoxy}hexyl)-5-(2,2-dimethyl-4H-1,3-benzodioxin-6-yl)-1,3-oxazolidin-2-one (0.202 g) in dichloromethane (4 ml) was treated with 4-biphenylyl isocyanate (0.126 g) and the mixture stirred under nitrogen at 20° C. for 19 h. Isopropanol (15 ml) was added to quench excess isocyanate, and the mixture stirred for 2 h. The solvents were removed in vacuo to give a residue which was purified by Biotage. Elution with 6:4 EtOAc/cyclohexane followed by solvent evaporation in vacuo gave the title compound (0.119 g). LCMS RT=4.09 min, ES+ve 694 (MH)$^+$.

ii) N-(1,1'-Biphenyl-4-yl)-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea Potassium trimethylsilanolate (0.090 g) was added to a solution of N-(1,1'-biphenyl-4-yl)-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea (0.119 g) in deoxygenated anhydrous THF (4 ml) whilst stirring under nitrogen. The reaction mixture was heated to 65° C. for 3 h, at which point the reaction mixture was cooled to room temperature. Phosphate buffer (25 ml, pH6.5) was added and the mixture extracted with EtOAc (3×25 ml). The combined organic layers were separated and dried over $Na_2SO_4$ before filtering. Solvent evaporation in vacuo gave a residue which was purified by Biotage. Elution with 150:8:1 dichloromethane:EtOH:ammonia followed by solvent evaporation in vacuo gave the title compound (0.092 g). LCMS RT=3.16 min, ES+ve 668 (MH)$^+$.

iii) N-(1,1'-Biphenyl-4-yl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea acetate A solution of N-(1,1'-biphenyl-4-yl)-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea (0.089 g) in acetic acid (4 ml) and water (2 ml) were stirred under nitrogen at 70° C. for 30 min. The reaction mixture was cooled to room temperature before concentrating under vacuum and azeotroping with MeOH (2×10 ml) to give the title compound (0.097 g). LCMS RT=3.08 min, ES+ve 628 (MH)+.

Example 6

Synthesis of N-cyclohexyl-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea i) N-Cyclohexyl-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea A solution of (5R)-3-(6-{2-[(3-aminobenzyl)oxy]ethoxy}hexyl)-5-(2,2-dimethyl-4H-1,3-benzodioxin-6-yl)-1,3-oxazolidin-2-one (0.209 g) in dichloromethane (4 ml) was treated with cyclohexyl isocyanate (0.075 g) and the mixture stirred under nitrogen at 20° C. for 3 h. At this point further cyclohexyl isocyanate (0.150 g) was added, and the reaction mixture stirred for a further 65 h. Isopropanol (15 ml) was added to quench excess isocyanate, and the mixture stirred for 3 h. The solvents were removed in vacuo to give a residue which was purified by Biotage. Elution with 6:4 EtOAc/cyclohexane followed by solvent evaporation in vacuo gave the title compound (0.212 g). LCMS RT=3.77 min, ES+ve 624 (MH)+.

ii) N-Cyclohexyl-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea Potassium trimethylsilanolate (0.177 g) was added to a solution of N-cyclohexyl-N'-(3-{[2-({6-[(5R)-5-(2,2-dimethyl-4H-1,3-benzodioxin-6-yl)-2-oxo-1,3-oxazolidin-3-yl]hexyl}oxy)ethoxy]methyl}phenyl)urea (0.207 g) in deoxygenated anhydrous THF (6 ml) whilst stirring under nitrogen. The reaction mixture was heated to 65° C. for 4.5 h, at which point the reaction mixture was cooled to room temperature. Phosphate buffer (25 ml, pH6.5) was added and the mixture left to stir for 10 min before extracting with EtOAc (3×25 ml). The combined organic layers were separated and dried over $Na_2SO_4$ before filtering. Solvent evaporation in vacuo gave a residue which was purified by Biotage. Elution with 150:8:1 dichloromethane:EtOH:ammonia followed by solvent evaporation in vacuo gave the title compound (0.138 g). LCMS RT=2.87 min, ES+ve 598 (MH)+.

iii) N-Cyclohexyl-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea triacetate A solution of N-cyclohexyl-N'-[3-({2-[(6-{[(2R)-2-(2,2-dimethyl-4H-1,3-benzodioxin-6-yl)-2-hydroxyethyl]amino}hexyl)oxy]ethoxy}methyl)phenyl]urea (0.138 g) in acetic acid (4 ml) and water (1 ml) were stirred under nitrogen at 70° C. for 45 min. The reaction mixture was cooled to room temperature before concentrating under vacuum and azeotroping with MeOH (3×10 ml) to give a residue which was purified by Biotage. Elution with 50:8:1 dichloromethane:EtOH:ammonia followed by solvent evaporation in vacuo gave the title compound (0.126 g). LCMS RT=2.65 min, ES+ve 558 (MH)+.

The following examples 7 to 9 and 11 to 20 were prepared similarly:

Example 7

4-[(1R)-2-({6-[2-(Benzyloxy)ethoxy]hexyl}amino)-1-hydroxyethyl]-2-(hydroxymethyl)phenol acetate.

LCMS RT=2.47 min, ES+ve 418 (MH)+.

Example 8

4-[(2-{[6-({(2R)-2-Hydroxy-2-[4-hydroxy-3-(hydroxymethyl)phenyl]ethyl}amino)-hexyl]oxy}ethoxy)methyl]benzenesulfonamide.

LCMS RT=2.18 min, ES+ve 497 (MH)+.

Example 9

4-{(1R)-1-Hydroxy-2-[(6-{2-[(4-iodobenzyl)oxy]ethoxy}hexyl)amino]ethyl}-2-(hydroxymethyl)phenol acetate.

LCMS RT=2.64 min, ES+ve 544 (MH)+.

Example 10

3-[(2-{[6-({(2R)-2-Hydroxy-2-[4-hydroxy-3-(hydroxymethyl)phenyl]ethyl}amino)hexyl]oxy}ethoxy)methyl]benzenesulfonamide acetate i) 3-(Hydroxymethyl)-N,N-bis{[2-(trimethylsilyl)ethoxy]methyl}benzenesulfonamide A solution of 3-(hydroxymethyl)benzenesulfonamide (670 mg) in DMF (20 ml) under nitrogen was treated with sodium hydride (315 mg, 60% in oil) and the mixture was stirred at 20° for 15 min. The mixture was then treated with 2-(trimethylsilyl)ethoxymethyl chloride (1.27 ml) and the mixture was stirred at 20° for 1 h. Phosphate buffer solution (50 ml, pH6.5) was added and the mixture was extracted with EtOAc. The extract was washed with water, dried ($Na_2SO_4$) and the solvent evaporated in vacuo to give a residue. The residue was purified by chromatography on flash silica gel (40 mm diameter column). Elution with EtOAc-cyclohexane (3:7) gave the title compound (985 mg). LCMS RT=3.84 min.

ii) 3-{[2-({6-[(5R)-5-(2,2-Dimethyl-4H-1,3-benzodioxin-6-yl)-2-oxo-1,3-oxazolidin-3-yl]hexyl}oxy)ethoxy]methyl}-N,N-bis{[2-(trimethylsilyl)ethoxy]methyl}benzenesulfonamide A solution of 3-(hydroxymethyl)-N,N-bis{[2-(trimethylsilyl)ethoxy]methyl}benzenesulfonamide (512 mg) in DMF (4 ml) under nitrogen was treated with sodium hydride (1.295 g, 60% in oil) and the mixture was stirred at 20° for 30 min. A solution of 2-({6-[(5R)-5-(2,2-dimethyl-4H-1,3-benzodioxin-6-yl)-2-oxo-1,3-oxazolidin-3-yl]hexyl}oxy)ethyl methanesulfonate (359 mg) in DMF (1 ml) was added and the mixture was stirred at 20° for 18 h. Phosphate buffer solution (25 ml, pH6.5) was added and the mixture was extracted with EtOAc. The extract was washed with water, dried (Na$_2$SO$_4$) and the solvent evaporated in vacuo to give a residue. The residue was purified by chromatography on flash silica gel (30 mm diameter column). Elution with EtOAc-cyclohexane (2:3) then (1:1) gave the title compound (400 mg). LCMS RT=4.43 min.

iii) 3-({2-[(6-{[(2R)-2-(2,2-Dimethyl-4H-1,3-benzodioxin-6-yl)-2-hydroxyethyl]amino}hexyl)oxy]ethoxy}methyl)-N,N-bis{[2-(trimethylsilyl)ethoxy]methyl}benzenesulfonamide A solution of 3-{[2-({6-[(5R)-5-(2,2-dimethyl-4H-1,3-benzodioxin-6-yl)-2-oxo-1,3-oxazolidin-3-yl]hexyl}oxy)ethoxy]methyl}-N,N-bis{[2-(trimethylsilyl)ethoxy]methyl}benzenesulfonamide (200 mg) in THF (10 ml) under nitrogen was treated with potassium trimethylsilanolate (125 mg) and the mixture heated to 70° for 5 h. The mixture was cooled to 20° and phosphate buffer solution (25 ml, pH6.5) was added. The mixture was extracted with EtOAc, the extract dried (Na$_2$SO$_4$) and the solvent evaporated in vacuo to give the title compound (400 mg). LCMS RT=3.6 min.

iv) 3-[(2-{[6-({(2R)-2-Hydroxy-2-[4-hydroxy-3-(hydroxymethyl)phenyl]ethyl}amino)hexyl]oxy}ethoxy)methyl]benzenesulfonamide acetate A solution of 3-({2-[(6-{[(2R)-2-(2,2-dimethyl-4H-1,3-benzodioxin-6-yl)-2-hydroxyethyl]amino}hexyl)oxy]ethoxy}methyl)-N,N-bis{[2-(trimethylsilyl)ethoxy]methyl}benzenesulfonamide (170 mg) in acetic acid (8 ml) and water (4 ml) was heated to 70° for 6 h. The mixture was cooled to 20° and the solvent evaporated in vacuo. The residue was purified by preparative TLC. Elution with dichloromethane-EtOH-0.880 ammonia (25:8:1) gave the free base (35 mg). This was dissolved in acetic acid (2 ml) and the solvent evaporated in vacuo to give the title compound (40 mg). LCMS RT=2.13 min, ES+ve 497 (MH)$^+$ Example 11

2-(Hydroxymethyl)-4-((1R)-1-hydroxy-2-{[6-(2-{[(1R)-1-phenylethyl]oxy}ethoxy)-hexyl]amino}ethyl)phenol acetate.

LCMS RT=2.55 min, ES+ve 432 (MH)$^+$.

Example 12

2-(Hydroxymethyl)-4-((1R)-1-hydroxy-2-{[6-(2-{[(1S)-1-phenylethyl]oxy}ethoxy)-hexyl]amino}ethyl)phenol acetate.

LCMS RT=2.45 min, ES+ve 432 (MH)$^+$.

Example 13

4-{(1R)-2-[(6-{2-[(4-Chlorobenzyl)oxy]ethoxy}hexyl)amino]-1-hydroxyethyl}-2-(hydroxymethyl)phenol acetate.

LCMS RT=2.61 min, ES+ve 452 (MH)$^+$, 454 (MH)$^+$.

Example 14

2-(Hydroxymethyl)-4-{(1R)-1-hydroxy-2-[(6-{2-[(4-methylbenzyl)oxy]-ethoxy}hexyl)amino]ethyl}phenol acetate.

LCMS RT=2.56 min, ES+ve 432 (MH)$^+$.

Example 15

4-{(1R)-2-[(6-{2-[(2,4-Dichlorobenzyl)oxy]ethoxy}hexyl)amino]-1-hydroxyethyl}-2-(hydroxymethyl)phenol acetate.

LCMS RT=2.77 min, ES+ve 486 (MH)$^+$, 488 (MH)$^+$, 490 (MH)$^+$.

Example 16

2-(Hydroxymethyl)-4-((1R)-1-hydroxy-2-{[6-(2-{[4-(trifluoromethyl)benzyl]-oxy}ethoxy)hexyl]amino}ethyl)phenol acetate LCMS RT=2.60 min, ES+ve 486 (MH)$^+$.

Example 17

4-{(1R)-1-Hydroxy-2-[(6-{2-[(3-hydroxybenzyl)oxy]ethoxy}hexyl)amino]ethyl}-2-(hydroxymethyl)phenol acetate.

LCMS RT=2.31 min, ES+ve 434 (MH)$^+$.

Example 18

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}urea acetate.

LCMS RT=2.30 min, ES+ve 476 (MH)$^+$.

Example 19

N-{3-[(2-{[6-({(2R)-2-Hydroxy-2-[4-hydroxy-3-(hydroxymethyl)phenyl]ethyl}amino)hexyl]oxy}ethoxy)methyl]phenyl}-4-methylsulfonyl)benzenesulfonamide acetate.

LCMS RT=2.54 min, ES+ve 451 (MH)$^+$.

Example 20

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}methanesulfonamide acetate.

LCMS RT=2.42 min, ES+ve 511 (MH)$^+$.

Example 21

Synthesis of N-(3-{[({3-[(2-{[6-({(2R)-2-hydroxy-2-[4-hydroxy-3-(hydroxymethyl)-phenyl]ethyl}amino)hexyl]oxy}ethoxy)methyl]phenyl}amino)carbonyl]amino}phenyl)pyridine-3-carboxamide i) 2-{(3-Nitrophenyl)methoxy}ethanol Ethylene glycol (7.18 g) in anhydrous DMF (50 ml) was treated at 0° under nitrogen with sodium hydride (60% dispersion in mineral oil, 1.85 g) and the mixture stirred for 30 min. 3-Nitrobenzyl bromide (5.00 g) was added and the mixture was warmed to 20° over 1 h and stirred for a further 15 h. Phosphate buffer (pH 6.5, 100 ml) and water (100 ml) were added and the product was extracted with EtOAc (2×150 ml). The combined organic layer was washed with water (2×200 ml) and dried (Na$_2$SO$_4$). Solvent evaporation in vacuo gave a residue that was purified by Biotage. Elution with EtOAc-PE (1:1 then 2:1) followed by solvent evaporation in vacuo gave the title compound (16.34 g) HPLC RT=1.554 min. TSP+ve 215 (MNH$_4$)$^+$.

ii) 1-[(2-[(6-Bromohexyl)oxy]ethoxy)methyl]-3-nitrobenzene

2-{(3-Nitrophenyl)methoxy}ethanol (6.50 g), 1,6-dibromohexane (24.2 g) and tetrabutylammonium bromide (0.21 g) were stirred under nitrogen at 20° and treated with 50% w/v sodium hydroxide (10 ml). The mixture was stirred vigorously for 19 h before water (150 ml) was added. The product was extracted with dichloromethane (3×80 ml) and the combined organic layer was dried (Na$_2$SO$_4$). Solvent evaporation in vacuo gave a residue that was purified by Biotage. Elution with PE-EtOAc (1:0 then 3:1) followed by solvent evaporation in vacuo gave the title compound (8.12 g). HPLC RT=3.238 min.

iii) 5R)-5-(2,2-Dimethyl-4H-1,3-benzodioxin-6-yl)-3-{6-[2-{(3-nitrophenyl)-methoxy}ethoxy]hexyl}-1,3-oxazolidin-2-one A solution of (5R)-5-(2,2-dimethyl-4H-1,3-benzodioxin-6-yl)-1,3-oxazolidin-2-one (4.40 g) in anhydrous DMF (75 ml) was treated under nitrogen at 0° with sodium hydride (60% dispersion in mineral oil, 1.04 g) and the mixture stirred for 40 min. A solution of 1-[(2-[(6-bromohexyl)oxy]ethoxy)methyl]-3-nitrobenzene (8.12 g) in DMF (10 ml) was added and the mixture stirred at 20° for 2 h. Phosphate buffer (pH 6.5, 100 ml) and water (100 ml) were added and the product extracted with EtOAc (4×100 ml). The combined organic layer was washed with water (3×100 ml) and dried (Na$_2$SO$_4$). The solvent was removed in vacuo to give a residue that was purified by Biotage. Elution with EtOAc-PE (1:1 then 3:2) followed by solvent evaporation in vacuo gave the title compound (9.50 g). LCMS RT=3.75 min, ES+ve 529 (MH)$^+$.

iv) (5R)-3-{6-[2-{(3-Aminophenyl)methoxy}ethoxy]hexyl}-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-{6-[2-{(3-nitrophenyl)methoxy}ethoxy]hexyl}-1,3-oxazolidin-2-one (9.50 g) in EtOAc (120 ml) and EtOH (120 ml) was hydrogenated over platinum oxide (0.20 g) for 1.75 h. The mixture was filtered through celite and washed with EtOH. Solvent evaporation in vacuo gave the title compound (9.60 g). LCMS RT=3.25 min, ES+ve 499 (MH)$^+$.

v) N-[3-({2-({6-[(5R)-5-(2,2-Dimethyl-4H-1,3-benzodioxin-6-yl)-2-oxo-1,3-oxazolidin-3-yl]hexyl}oxy)ethoxy}methyl)phenyl]-N'-(3-nitrophenyl)urea A solution of (5R)-3-{6-[2-{(3-aminophenyl)methoxy}ethoxy]hexyl}-5-(2,2-dimethyl-4H-1,3-benzodioxin-6-yl)-1,3-oxazolidin-2-one (1.00 g) in anhydrous dichloromethane (15 ml) was treated under nitrogen at 20° with 3-nitrophenyl isocyanate (0.43 g) and the mixture stirred for 4 h. Isopropanol (20 ml) was added and the mixture stirred for 17 h before the solvent was removed in vacuo to give a residue that was purified by Biotage. Elution with dichloromethane-EtOH-ammonia (325:8:1) followed by solvent evaporation in vacuo gave the title compound (1.13 g). LCMS RT=3.85 min, ES+ve 663 (MH)$^+$.

vi) N-(3-Aminophenyl)-N'-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]urea A solution of N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-N'-(3-nitrophenyl)urea (0.976 g) in EtOH (12 ml) and EtOAc (12 ml) was hydrogenated over platinum oxide (0.020 g) for 2 h. The mixture was filtered through celite and washed with EtOH. Solvent evaporation in vacuo gave the title compound (0.93 g). LCMS RT=3.48 min, ES+ve 633 (MH)$^+$.

vii) N-{3-[({[3-({2-({6-[(5R)-5-(2,2-Dimethyl-4H-1,3-benzodioxin-6-yl)-2-oxo-1,3-oxazolidin-3-yl]hexyl}oxy)ethoxy}methyl)phenyl]amino}carbonyl)amino]-phenyl}pyridine-3-carboxamide A solution of N-(3-aminophenyl)-N'-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-urea (0.20 g) in pyridine (4 ml) was treated under nitrogen at 20° with nicotinoyl chloride hydrochloride (0.118 g) and the mixture stirred for 5.5 h. Sat. sodium bicarbonate solution (25 ml) was added and the product was extracted with dichloromethane (3×20 ml). The combined organic layer was dried (Na$_2$SO$_4$) and the solvent removed in vacuo to give a residue that was purified by SPE. Elution with dichloromethane-EtOAc (1:0, 1:1, then 0:1), then MeOH-EtOAc (1:50), followed by solvent evaporation in vacuo gave the title compound (0.209 g). LCMS RT=3.54 min, ES+ve 738 (MH)$^+$.

viii) N-(3-{[({3-[(2-[(6-{[(2R)-2-(2,2-Dimethyl-4H-1,3-benzodioxin-6-yl)-2-hydroxyethyl]amino}hexyl)oxy]ethoxy)methyl]phenyl}amino)carbonyl]amino}-phenyl)pyridine-3-carboxamide A solution of N-{3-[({[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]amino}carbonyl)-amino]phenyl}pyridine-3-carboxamide (0.209 g) in anhydrous THF (10 ml) was treated under nitrogen at 20° with potassium trimethylsilanolate (0.217 g). The mixture was heated to 65° for 2.5 h before cooling to room temperature. Phosphate buffer (pH 6.5, 25 ml) was added and the product extracted with EtOAc (3×20 ml). Solvent evaporation in vacuo gave a residue that was purified by SPE. Elution with dichloromethane-EtOH-ammonia (100:8:1 then 50:8:1) followed by solvent evaporation in vacuo gave the title compound (0.109 g). LCMS RT=2.86 min, ES+ve 712 (MH)$^+$.

ix) N-(3-{[({3-[(2-{[6-({(2R)-2-Hydroxy-2-[4-hydroxy-3-(hydroxymethyl)phenyl]-ethyl}amino)hexyl]oxy}ethoxy)methyl]phenyl}amino)carbonyl]amino}phenyl)-pyridine-3-carboxamide A solution of N-(3-{[({3-[(2-[(6-{[(2R)-2-(2,2-dimethyl-4H-1,3-benzodioxin-6-yl)-2-hydroxyethyl]amino}hexyl)oxy]ethoxy)methyl]phenyl}amino)carbonyl]amino}-phenyl)pyridine-3-carboxamide (0.109 g) in acetic acid (4 ml) and water (2 ml) was heated to 68° for 30 min. The mixture was cooled to room temperature before concentrating in vacuo to leave a residue that was purified by Biotage. Elution with dichloromethane-EtOH-ammonia (25:8:1) followed by solvent evaporation in vacuo gave the title compound (0.089 g). LCMS RT=2.02 min, ES+ve 672 (MH)$^+$.

Example 22

Synthesis of N-cyclohexyl-3-[(2-{[6-({(2R)-2-hydroxy-2-[4-hydroxy-3-(hydroxymethyl)phenyl]ethyl}amino)hexyl]oxy}ethoxy)methyl]benzenesulfonamide compound with (2E)-but-2-enedioic acid (2:1)

i) 3-[(Cyclohexylamino)sulfonyl]benzoic acid

A mixture of 3-(chlorosulfonyl)benzoic acid (2.00 g) and dichloromethane (20 ml) under nitrogen at 0° was treated with cyclohexylamine (3.63 ml) and the mixture was stirred at 0° for 0.5 h. The solvent was evaporated in vacuo and the residue was treated with 1M potassium hydrogen sulfate solution (50 ml) and extracted with EtOAc (3×50 ml). The combined extracts were dried (Na$_2$SO$_4$) and the solvent evaporated in vacuo to give the title compound (2.28 g). LCMS RT=3.16 min, ES+ve 284 (MH)$^+$.

ii) N-Cyclohexyl-3-(hydroxymethyl)benzenesulfonamide

A solution of 3-[(cyclohexylamino)sulfonyl]benzoic acid (2.25 g) in THF (100 ml) under nitrogen at 0° was treated dropwise with 1M borane-THF solution (23.82 ml). The mixture was stirred at 0° for 0.5 h and then at 20° for 72 h. The mixture was cooled to 0° and MeOH (20 ml) was added dropwise. The mixture was stirred for 15 min and then 2N hydrochloric acid (50 ml) was added and the mixture was allowed to warm to 20°. The bulk of the organic solvents were removed by evaporation in vacuo and the residual aqueous phase was extracted with EtOAc (2×40 ml). The combined extracts were dried (Na$_2$SO$_4$) and the solvent evaporated in vacuo. The residue was purified by SPE on alumina (10 g, activated, neutral, Brockmann 1). Elution with MeOH-dichloromethane (1:20) gave the title compound (1.944 g). LCMS RT=2.95 min, ES+ve 270 (MH)$^+$.

iii) N-Cyclohexyl-3-(hydroxymethyl)-N-({2-(trimethylsilyl)ethoxy}methyl)-benzenesulfonamide A solution of N-cyclohexyl-3-(hydroxymethyl)benzenesulfonamide (1.744 g) in DMF (30 ml) under nitrogen was treated with sodium hydride (60% dispersion in mineral oil, 311 mg) and the mixture stirred at 20° for 0.5 h. 2-(Trimethylsilyl)ethoxymethyl chloride (1.15 ml) was added and the mixture was stirred for a further 2 h at 20°. Phosphate buffer solution (pH 6.5, 50 ml) and water (50 ml) were added and the mixture was extracted with EtOAc (2×50 ml). The combined extracts were washed with water (2×100 ml) and dried (Na$_2$SO$_4$). Solvent evaporation in vacuo gave a residue which was purified by flash chromatography on silica gel. Elution with EtOAc-PE (3:7) gave the title compound (1.917 g). LCMS RT=3.83 min, ES+ve 417 (MNH$_4$)$^+$.

iv) 2-({6-[(5R)-5-(2,2-Dimethyl-4H-1,3-benzodioxin-6-yl)-2-oxo-1,3-oxazolidin-3-yl]hexyl}oxy) ethyl methanesulfonate A solution of (5R)-5-(2,2-dimethyl-4H-1,3-benzodioxin-6-yl)-3-{6-[2-hydroxyethoxy]hexyl}-1,3-oxazolidin-2-one (200 mg) in dichloromethane (14 ml) under nitrogen at 0° was treated with diisopropylethylamine (0.10 ml) followed by methanesulfonyl chloride (0.04 ml). The mixture was stirred at 0° for 0.5 h and sat. sodium bicarbonate solution (30 ml) was then added. The mixture was extracted with dichloromethane (30 ml) and the organic extract dried (Na$_2$SO$_4$). The solvent was evaporated in vacuo to give the title compound (240 mg). LCMS RT=3.22 min, ES+ve 472 (MH)$^+$.

v) N-Cyclohexyl-3-({2-({6-[(5R)-5-(2,2-dimethyl-4H-1,3-benzodioxin-6-yl)-2-oxo-1,3-oxazolidin-3-yl]hexyl}oxy)ethoxy}methyl)-N-({2-(trimethylsilyl)ethoxy}methyl)-benzenesulfonamide A solution of N-cyclohexyl-3-(hydroxymethyl)-N-({2-(trimethylsilyl)ethoxy}-methyl)benzenesulfonamide (508 mg) in DMF (8 ml) under nitrogen at 20° was treated with sodium hydride (60% dispersion in mineral oil, 58 mg) and the mixture was stirred 15 min. A solution of 2-({6-[(5R)-5-(2,2-dimethyl-4H-1,3-benzodioxin-6-yl)-2-oxo-1,3-oxazolidin-3-yl]hexyl}oxy)ethyl methanesulfonate (400 mg) in DMF (2 ml) was added and the mixture was stirred at 20° for 72 h. Phosphate buffer solution (pH 6.5, 10 ml) and water (20 ml) were added and the mixture was extracted with EtOAc (30 ml). The extract was washed with water (2×30 ml), dried (Na$_2$SO$_4$) and the solvent evaporated in vacuo. The residue was purified by flash chromatography on silica gel. Elution with EtOAc-PE (1:1) gave the title compound (530 mg). LCMS RT=4.47 min, ES+ve 793 (MH)$^+$.

vi) N-Cyclohexyl-3-[(2-[(6-{[(2R)-2-(2,2-dimethyl-4H-1,3-benzodioxin-6-yl)-2-hydroxyethyl]amino}hexyl)oxy]ethoxy)methyl]-N-({2-trimethylsilyl)ethoxy}methyl)benzenesulfonamide The title compound was prepared by a procedure similar to that described in Example 1 xii). LCMS RT=3.58 min, ES+ve 749 (MH)$^+$.

vii) N-Cyclohexyl-3-[(2-{[6-({(2R)-2-hydroxy-2-[4-hydroxy-3-(hydroxymethyl)-phenyl]ethyl}amino) hexyl]oxy}ethoxy)methyl]benzenesulfonamide compound with (2E)-but-2-enedioic acid (2:1)

A solution of N-cyclohexyl-3-[(2-[(6-{[(2R)-2-(2,2-dimethyl-4H-1,3-benzodioxin-6-yl)-2-hydroxyethyl]amino}hexyl)oxy]ethoxy)methyl]-N-({[2-(trimethylsilyl)-ethyl]oxy}methyl)benzenesulfonamide (350 mg) in acetic acid (20 ml) and water (10 ml) was heated to 70° for 1 h. The mixture was cooled to 20° and the solvent was evaporated in vacuo. The residue was azeotroped with MeOH (2×10 ml) and the residue was purified by preparative TLC. Elution with dichloromethane-EtOH-ammonia (25:8:1) gave the free base (200 mg). This was dissolved in EtOH (5 ml) and treated with a solution of fumaric acid (20 mg) in EtOH (5 ml). The solvent was evaporated in vacuo to give the title compound (216 mg). LCMS RT=2.70 min, ES+ve 579 (MH)$^+$.

Example 23

Synthesis of N-{3-[(2-{[6-({(2R)-2-hydroxy-2-[4-hydroxy-3-(hydroxymethyl)-phenyl]ethyl}amino) hexyl]oxy}ethoxy)methyl]phenyl}-3-[(phenylsulfonyl)amino]benzamide compound with (2E)-but-2-enedioic acid (2:1)

i) N-[3-({2-({6-[(5R)-5-(2,2-Dimethyl-4H-1,3-benzodioxin-6-yl)-2-oxo-1,3-oxazolidin-3-yl] hexyl}oxy)ethoxy)methyl)phenyl]-3-nitrobenzamide A solution of (5R)-3-{6-[2-{[(3-aminophenyl)methyl]oxy}ethoxy]hexyl}-5-(2,2-dimethyl-4H-1,3-benzodioxin-6- yl)-1,3-oxazolidin-2-one (2.20 g) in pyridine (20 ml) under nitrogen was treated with 3-nitrobenzoyl chloride (819 mg) and the mixture was stirred at 20° for 2.5 h. Sat. sodium bicarbonate solution (100 ml) was added and the mixture was extracted with dichloromethane (2×50 ml). The combined extracts were dried (Na$_2$SO$_4$) and the solvent evaporated in vacuo. The residue was purified by flash chromatography on silica gel. Elution with EtOAc-PE (2:1) gave the title compound (2.11 g). LCMS RT=3.71 min, ES+ve 648 (MH)$^+$.

ii) 3-Amino-N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]benzamide A solution of N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-3-nitrobenzamide (2.11 g) in EtOAc (30 ml) and EtOH (30 ml) was hydrogenated over platinum oxide (100 mg). After 1.25 h the mixture was filtered through celite and the filtrate evaporated in vacuo to give the title compound (1.955 g). LCMS RT=3.49 min, ES+ve 618 (MH)$^+$.

iii) N-[3-({2-({6-[(5R)-5-(2,2-Dimethyl-4H-1,3-benzodioxin-6-yl)-2-oxo-1,3-oxazolidin-3-yl]hexyl}oxy)ethoxy}methyl)phenyl]-3-[(phenylsulfonyl)amino]-benzamide 3-Amino-N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]benzamide (200 mg) in pyridine (5 ml) under nitrogen was treated with benzenesulfonyl chloride (0.045 ml) and the mixture was stirred at 20° for 2 h. Sat. sodium bicarbonate solution (30 ml) was added and the mixture was extracted with dichloromethane (2×20 ml). The combined extracts were dried (Na$_2$SO$_4$) and the solvent evaporated in vacuo. The residue was purified by flash chromatography on silica gel. Elution with EtOAc-dichloromethane (1:1) gave the title compound (155 mg). LCMS RT=3.72 min, ES+ve 758 (MH)$^+$.

iv) N-{3-[(2-[(6-{[(2R)-2-(2,2-Dimethyl-4H-1,3-benzodioxin-6-yl)-2-hydroxyethyl]-amino}hexyl)oxy]ethoxy)methyl]phenyl}-3-[(phenylsulfonyl)amino]benzamide The title compound was prepared by a procedure similar to that described in Example 1 xii). LCMS RT=2.96 min, ES+ve 732 (MH)$^+$.

v) N-{3-[(2-{[6-({(2R)-2-Hydroxy-2-[4-hydroxy-3-(hydroxymethyl)phenyl]-ethyl}amino)hexyl]oxy}ethoxy)methyl]phenyl}-3-[(phenylsulfonyl)amino]-benzamide compound with (2E)-but-2-enedioic acid (2:1)

The title compound was prepared by a procedure similar to that described in Example 22 vii). LCMS RT=2.71 min, ES+ve 692 (MH)$^+$.

Example 24

Synthesis of 4-[(1R)-2-({6-[2-({3-[(2,3-dihydroimidazo[2,1-b][1,3]thiazol-6-ylmethyl)amino]benzyl}oxy)ethoxy]hexyl}amino)-1-hydroxyethyl]-2-(hydroxymethyl)phenol acetate (1:2)

i) (5R)-3-[6-(2-[({3-[(2,3-Dihydroimidazo[2,1-b][1,3]thiazol-6-ylmethyl)amino]-phenyl}methyl)oxy]ethoxy)hexyl]-5-(2,2-dimethyl-4H-1,3-benzodioxin-6-yl)-1,3-oxazolidin-2-one A solution of (5R)-3-{6-[2-{[(3-aminophenyl)methyl]oxy}ethoxy]hexyl}-5-(2,2-dimethyl-4H-1,3-benzodioxin-6-yl)-1,3-oxazolidin-2-one (200 mg) and 2,3-dihydroimidazo[2,1-b][1,3]thiazole-6-carboxaldehyde (62 mg) (WO94/10178) in dichloromethane (10 ml) was treated under nitrogen with sodium triacetoxy borohydride (340 mg) and stirred at 20° for 1.5 h. The mixture was cooled to 0°, phosphate buffer solution (pH6.5, 20 ml) was added and the mixture was extracted with EtOAc (3×30 ml). The combined organic extracts were dried (Na$_2$SO$_4$) and the solvent evaporated in vacuo to give a residue which was purified by SPE. Elution with dichloromethane, dichloromethane-EtOH-ammonia (400:8:1) then (225:8:1) gave the title compound (172 mg). LCMS RT=3.16 min, ES+ve 637 (MH)$^+$.

ii) (1R)-2-{6-(2-[{3-[(2,3-Dihydroimidazo[2,1-b][1,3]thiazol-6-ylmethyl)amino]-phenyl}methoxy]ethoxy)hexyl]amino}-1-(2,2-dimethyl-4H-1,3-benzodioxin-6-yl)ethanol The title compound was prepared by a procedure similar to that described in Example 21 viii). LCMS RT=2.46 min, ES+ve 611 (MH)$^+$.

iii) 4-[(1R)-2-({6-[2-({3-[(2,3-Dihydroimidazo[2,1-b][1,3]thiazol-6-ylmethyl)amino]-benzyl}oxy)ethoxy]hexyl}amino)-1-hydroxyethyl]-2-(hydroxymethyl)phenol acetate (1:2)

The title compound was prepared by a procedure similar to that described in Example 22 vii). LCMS RT=2.25 min, ES+ve 571 (MH)$^+$.

Example 25

Synthesis of N-cyclopropyl-3'-[(2-{[6-({(2R)-2-hydroxy-2-[4-hydroxy-3-(hydroxy-methyl)phenyl]ethyl}amino)hexyl]oxy}ethoxy)methyl]-1,1'-biphenyl-2-sulfonamide acetate i) (5R)-5-(2,2-Dimethyl-4H-1,3-benzodioxin-6-yl)-3-(6-{2-([3-(4,4,5,5-tetramethyl-1,3,2-dioxaborolan-2-yl)phenyl]methoxy)ethoxy}hexyl)-1,3-oxazolidin-2-one A stirred mixture of (5R)-5-(2,2-dimethyl-4H-1,3-benzodioxin-6-yl)-3-{6-[2-{(3-iodophenyl)methoxy}ethoxy]hexyl}-1,3-oxazolidin-2-one (1.3 g), bis(pinacolato)diboron (0.94 g), potassium acetate (0.62 g) and [1,1'-bis(diphenylphosphino)ferrocene]dichloropalladium(II) (complex with dichloromethane 1:1, 100 mg) in DMF (25 ml) under nitrogen was heated at 90° for 3.5 h. The mixture was cooled to 20°, poured into water (400 ml) and extracted with EtOAc (3×50 ml). The extracts were washed with water (200 ml), dried (MgSO$_4$) and evaporated in vacuo to give a residue which was purified by Biotage. Elution with diethyl ether-PE (4:1) gave the title compound (920 mg). LCMS RT=3.93 min, ES+ve 610 (MH)+.

ii) 1,1-Dimethylethyl(2-bromophenyl)sulfonyl(cyclopropyl)carbamate

Cyclopropylamine (1.7 g) was added to a stirred solution of 2-bromobenzenesulfonyl chloride (2.0 g) in THF (25 ml) under nitrogen. The mixture was stirred at 0° for 20 min and the solvent was then evaporated in vacuo. The residue was then triturated with cold water (20 ml), the mixture filtered and the filter cake dried in vacuo. The filter cake was then dissolved in dichloromethane (30 ml) and treated with triethylamine (1.53 ml) and 4-(dimethylamino)pyridine (90 mg) with stirring under nitrogen. The mixture was cooled to 0° and was treated with di-tert-butyl dicarbonate (2.4 g). The mixture was then stirred at 5° for 1 h and then washed with 1N hydrochloric acid (40 ml), water (50 ml) and was dried (Na$_2$SO$_4$). The solvent was evaporated in vacuo and the residue was recrystallised from cyclohexane (30 ml) to give the title compound (2.00 g). LCMS RT=3.52 min, ES+ve 393 (MNH$_4$)+, 395 (MNH$_4$)+.

iii) 1,1-Dimethylethyl cyclopropyl{[3'-({2-({6-[(5R)-5-(2,2-dimethyl-4H-1,3-benzodioxin-6-yl)-2-oxo-1,3-oxazolidin-3-yl]hexyl}oxy)ethoxy}methyl)-1,1'-biphenyl-2-yl]sulfonyl}carbamate A stirred mixture of (5R)-5-(2,2-dimethyl-4H-1,3-benzodioxin-6-yl)-3-(6-{2-({[3-(4,4,5,5-tetramethyl-1,3,2-dioxaborolan-2-yl)phenyl]methyl}oxy)ethoxy}hexyl)-1,3-oxazolidin-2-one (420 mg), 1,1-dimethylethyl(2-bromophenyl)-sulfonyl(cyclopropyl)carbamate (341 mg) and potassium carbonate (520 mg) in dimethoxyethane (10 ml) under nitrogen was treated with [1,1'-bis(diphenylphosphino)ferrocene]dichloropalladium(II) (complex with dichloromethane 1:1, 100 mg) and the mixture heated under reflux for 18 h. The mixture was cooled to 20°, diluted with EtOAc (25 ml) and filtered through celite. The filtrate was evaporated in vacuo to give a residue which was purified by Biotage. Elution with diethyl ether-PE (4:1) gave the title compound (262 mg). LCMS RT=4.15 min, ES –ve 822 (MHCO$_2$)−.

iv) N-Cyclopropyl-3'-[(2-[(6-{[(2R)-2-(2,2-dimethyl-4H-1,3-benzodioxin-6-yl)-2-hydroxyethyl]amino}hexyl)oxy]ethoxy)methyl]-1,1'-biphenyl-2-sulfonamide A stirred mixture of 1,1-dimethylethyl cyclopropyl{[3'-({2-({6-[(5R)-5-(2,2-dimethyl-4H-1,3-benzodioxin-6-yl)-2-oxo-1,3-oxazolidin-3-yl]hexyl}oxy)ethoxy}methyl)-1,1'-biphenyl-2-yl]sulfonyl}carbamate (260 mg) and potassium trimethylsilanolate (420 mg) in THF (10 ml) was heated under reflux for 2 h. The mixture was cooled to 20°, poured into phosphate buffer solution (pH6.5, 50 ml) and extracted with EtOAc (3×30 ml). The combined organic extracts were washed with water (50 ml), dried (MgSO$_4$) and the solvent evaporated in vacuo to give a residue which was purified by Biotage. Elution with dichloromethane-ethanol-ammonia (100:8:1) gave the title compound (132 mg). LCMS RT=3.06 min, ES+ve 653 (MH)+.

v) N-Cyclopropyl-3'-[(2-{[6-({(2R)-2-hydroxy-2-[4-hydroxy-3-(hydroxymethyl)-phenyl]ethyl}amino)hexyl]oxy}ethoxy)methyl]-1,1'-biphenyl-2-sulfonamide acetate The title compound was prepared by a procedure similar to that described in Example 1 xiii). LCMS RT=2.75 min, ES+ve 613 (MH)+.

Example 26

Synthesis of N-{3-[(2-{[6-({(2R)-2-hydroxy-2-[4-hydroxy-3-(hydroxymethyl)-phenyl]ethyl}amino)hexyl]oxy}ethoxy)methyl]phenyl}-N'-[3-(phenylethynyl)phenyl]urea i) N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-N'-(3-iodophenyl)urea 3-Iodophenylisocyanate (500 mg) was added to a solution of (5R)-3-{6-[2-{[(3-aminophenyl)methyl]oxy}ethoxy]hexyl}-5-(2,2-dimethyl-4H-1,3-benzodioxin-6-yl)-1,3-oxazolidin-2-one (700 mg) in dichloromethane (14 ml) and the mixture was stirred at 20° under nitrogen for 5 h. Isopropanol (14 ml) was added and the mixture was stirred for 16 h. The solvent was evaporated in vacuo to give a residue that was purified by Biotage. Elution with EtOAc-PE (2:1) gave the title compound (800 mg). LCMS RT=4.02 min, ES+ve 744 (MH)+.

ii) N-[3-({2-({6-[(5R)-5-(2,2-Dimethyl-4H-1,3-benzodioxin-6-yl)-2-oxo-1,3-oxazolidin-3-yl]hexyl}oxy)ethoxy}methyl)phenyl]-N'-[3-(phenylethynyl)phenyl]urea A solution of N-[3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenyl]-N'-(3-iodophenyl)urea (393 mg) and phenylacetylene (77 mg) in DMF (6 ml) was treated with diisopropylethylamine (5 ml) and nitrogen was passed through the solution for 5 min. Copper (I) iodide (10 mg) and dichlorobis(triphenylphosphine)palladium(II) (47 mg) were added and the mixture was stirred under nitrogen at 20° for 21.5 h. The solvent was evaporated in vacuo and EtOAc (15 ml) was added. The supernatant solution was collected and the solvent evaporated in vacuo to give a residue which was purified by Biotage. Elution with dichloromethane-ethanol-ammonia (325:8:1) gave the title compound (328 mg). LCMS RT=3.93 min, ES+ve 718 (MH)+.

iii) N-{3-[(2-[(6-{[(2R)-2-(2,2-Dimethyl-4H-1,3-benzodioxin-6-yl)-2-hydroxyethyl]-amino}hexyl)oxy]ethoxy)methyl]phenyl}-N'-[3-(phenylethynyl)phenyl]urea The title compound was prepared by a procedure similar to that described in Example 25 iv). LCMS RT=3.35 min, ES+ve 692 (MH)+.

iv) N-{3-[(2-{[6-({(2R)-2-Hydroxy-2-[4-hydroxy-3-(hydroxymethyl)phenyl]ethyl}-amino)hexyl]oxy}ethoxy)methyl]phenyl}-N'-[3-(phenylethynyl)phenyl]urea A solution of N-{3-[(2-[(6-{[(2R)-2-(2,2-dimethyl-4H-1,3-benzodioxin-6-yl)-2-hydroxyethyl]amino}hexyl)oxy]ethoxy)methyl]phenyl}-N'-[3-(phenylethynyl)-phenyl]urea (242 mg) in MeOH (8 ml) was loaded under gravity onto an SCX cartridge which had been pre-conditioned with MeOH. Elution with MeOH then ammonia-MeOH (15:100) gave a residue which was passed through an SCX cartridge as described above two more times. The resulting residue was purified by Biotage. Elution with dichloromethane-ethanol-ammonia (50:8:1) gave the title compound (145 mg). LCMS RT=3.34 min, ES+ve 652 (MH)+.

Example 27

Synthesis of N-{3-[(2-{[6-({(2R)-2-hydroxy-2-[4-hydroxy-3-(hydroxymethyl)-phenyl]ethyl}amino)hexyl]oxy}ethoxy)methyl]phenyl}-N'-[3-(2-phenyl-ethyl)-phenyl]urea compound with (2E)-but-2-enedioic acid (3:2)

A solution of N-{3-[(2-{[6-({(2R)-2-hydroxy-2-[4-hydroxy-3-(hydroxymethyl)-phenyl]ethyl}amino)hexyl]oxy}ethoxy)methyl]phenyl}-N'-[3-(phenylethynyl)-phenyl]urea (70 mg) in EtOH (15 ml) was hydrogenated over 10% palladium on activated charcoal (70 mg). After 2 h the mixture was filtered through celite and the solvent was partially evaporated in vacuo. Fumaric acid (6.2 mg) was added and the solvent was evaporated in vacuo to give a residue. The residue was treated with hot MeOH (10 ml) and was filtered. The filtrate was evaporated in vacuo to give the title compound (48 mg). LCMS RT=3.25 min, ES+ve 655 (MH)+.

Example 28

Synthesis of cyclopentyl 3-[(2-{[6-({(2R)-2-hydroxy-2-[4-hydroxy-3-(hydroxymethyl)phenyl]ethyl}amino)hexyl]oxy}ethoxy)methyl]phenylcarbamate acetate i) Cyclopentyl 3-({2-({6-[(5R)-5-(2,2-dimethyl-4H-1,3-benzodioxin-6-yl)-2-oxo-1,3-oxazolidin-3-yl]hexyl}oxy)ethoxy}methyl)phenylcarbamate A stirred solution of (5R)-3-{6-[2-{[(3-aminophenyl)methyl]oxy}ethoxy]-hexyl}-5-(2,2-dimethyl-4H-1,3-benzodioxin-6-yl)-1,3-oxazolidin-2-one (201 mg) and diisopropylethylamine (0.54 ml) in dichloromethane (10 ml) under nitrogen was treated with cyclopentychloroformate (0.348 ml) and the mixture was stirred at 20° for 51 h. Sat. sodium bicarbonate solution (20 ml) was added and the mixture was extracted with dichloromethane (3×20 ml). The combined extracts were dried (Na$_2$SO$_4$) and the solvent evaporated in vacuo to give a residue which was purified by Biotage. Elution with dichloromethane-ethanol-ammonia (275:8:1) gave the title compound (100 mg). LCMS RT=3.80 min, ES+ve 611 (MH)+.

ii) Cyclopentyl 3-[(2-[(6-{[(2R)-2-(2,2-dimethyl-4H-1,3-benzodioxin-6-yl)-2-hydroxyethyl]amino}hexyl)oxy]ethoxy)methyl]phenylcarbamate The title compound was prepared by a procedure similar to that described in Example 25 iv). LCMS RT=3.05 min, ES+ve 585 (MH)+.

iii) Cyclopentyl 3-[(2-{[6-({(2R)-2-hydroxy-2-[4-hydroxy-3-(hydroxymethyl)phenyl]-ethyl}amino)hexyl]oxy}ethoxy)methyl]phenylcarbamate acetate The title compound was prepared by a procedure similar to that described in Example 1 xiii). LCMS RT=2.71 min, ES+ve 545 (MH)+.

Example 29

Synthesis of 5-{3'-[(2-{[6-({(2R)-2-hydroxy-2-[4-hydroxy-3-(hydroxymethyl)-phenyl]ethyl}amino)hexyl]oxy}ethoxy)methyl]-1,1'-biphenyl-3-yl}pyrimidine-2,4(1H,3H)-dione acetate i) (5R)-3-{6-[2-{[(3'-{2,4-bis(1,1-Dimethylethyl)oxy]pyrimidin-5-yl}-1,1'-biphenyl-3-yl)methoxy}ethoxy]hexyl}-5-(2,2-dimethyl-4H-1,3-benzodioxin-6-yl)-1,3-oxazolidin-2-one The title compound was prepared by a procedure similar to that described in Example 25 iii). LCMS RT=4.43 min, ES+ve 782 (MH)+.

ii) (1R)-2-{[6-(2-{[3'-{2,4-bis[(1,1-Dimethylethyl)oxy]pyrimidin-5-yl}-1,1'-biphenyl-3-yl]methoxy}ethoxy)hexyl]amino}-1-(2,2-dimethyl-4H-1,3-benzodioxin-6-yl)ethanol The title compound was prepared by a procedure similar to that described in Example 21 viii). LCMS RT=3.73 min, ES+ve 756 (MH)+.

iii) 5-{3'-[(2-{[6-({(2R)-2-Hydroxy-2-[4-hydroxy-3-(hydroxymethyl)phenyl]ethyl}-amino)hexyl]oxy}ethoxy)methyl]-1,1'-biphenyl-3-yl}pyrimidine-2,4(1H,3H)-dione acetate The title compound was prepared by a procedure similar to that described in Example 1xiii)). LCMS RT=2.57 min, ES+ve 604 (MH)+.

Example 30

Synthesis of 4-{(1R)-1-hydroxy-2-[(6-{2-[(3-iodobenzyl)oxy]ethoxy}hexyl)amino]-ethyl}-2-(hydroxymethyl)phenol acetate i) 2-{(3-Iodophenyl)methoxy}ethanol The title compound was prepared by a procedure similar to that described in Example 21 i). LCMS RT=2.84 min, ES+ve 296 (MNH$_4$)+.

ii) 1-[(2-[(6-Bromohexyl)oxy]ethoxy)methyl]-3-iodobenzene

The title compound was prepared by a procedure similar to that described in Example 21 ii). LCMS RT=4.12 min.

iii) (5R)-5-(2,2-Dimethyl-4H-1,3-benzodioxin-6-yl)-3-{6-[2-{(3-iodophenyl)-methoxy}ethoxy]hexyl}-1,3-oxazolidin-2-one The title compound was prepared by a procedure similar to that described in Example 21 iii). LCMS RT=3.87 min, ES+ve 610 (MH)+.

iv) R)-1-(2,2-Dimethyl-4H-1,3-benzodioxin-6-yl)-2-[(6-{2-[(3-iodobenzyl)oxy]-ethoxy}hexyl)amino]ethanol The title compound was prepared by a procedure similar to that described in Example 21 viii). LCMS RT=3.07 min, ES+ve 584 (MH)+.

v) 4-{(1R)-1-Hydroxy-2-[(6-{2-[(3-iodobenzyl)oxy]ethoxy}hexyl)amino]ethyl}-2-(hydroxymethyl)phenol acetate The title compound was prepared by a procedure similar to that described in Example 1xiii). LCMS RT=2.73 min, ES−ve 542 (M−H)−.

Example 31

Synthesis of 3'-[(2-{[6-({(2R)-2-hydroxy-2-[4-hydroxy-3-(hydroxymethyl)phenyl]-ethyl}amino)hexyl]oxy}ethoxy)methyl]-1,1'-biphenyl-3-ol acetate i) (5R)-5-(2,2-Dimethyl-4H-1,3-benzodioxin-6-yl)-3-{6-[2-{[(3'-hydroxy-1,1'-biphenyl-3-yl)methyl]oxy}ethoxy]hexyl}-1,3-oxazolidin-2-one A stirred mixture of (5R)-5-(2,2-dimethyl-4H-1,3-benzodioxin-6-yl)-3-{6-[2-{[(3-iodophenyl)methyl]oxy}ethoxy]hexyl}-1,3-oxazolidin-2-one (300 mg), 3-hydroxyphenylboronic acid (102 mg), tripotassium phosphate (417 mg) and dichlorobis(triphenylphosphine)palladium(II) (100 mg) in dimethoxymethane (10 ml) under nitrogen was heated under reflux for 4 h. The mixture was cooled to 20° and diluted with water (50 ml). The mixture was extracted with EtOAc (2×25 ml) and the combined extracts washed with water (50 ml) and dried (Na$_2$SO$_4$). Solvent evaporation in vacuo gave a residue which was purified by Biotage. Elution with diethyl ether gave the title compound (130 mg). LCMS RT=3.74 min, ES+ve 593 (MNH$_4$)+.

ii) 3'-[(2-[(6-{[(2R)-2-(2,2-Dimethyl-4H-1,3-benzodioxin-6-yl)-2-hydroxyethyl]-amino}hexyl)oxy]ethoxy)methyl]-1,1'-biphenyl-3-ol The title compound was prepared by a procedure similar to that described in Example 21 viii). LCMS RT=2.99 min, ES+ve 550 (MH)+.

iii) 3'-[(2-{[6-({(2R)-2-Hydroxy-2-[4-hydroxy-3-(hydroxymethyl)phenyl]ethyl}-amino)hexyl]oxy}ethoxy)methyl]-1,1'-biphenyl-3-ol acetate The title compound was prepared by a procedure similar to that described in Example 1 xiii). LCMS RT=2.69 min, ES+ve 510 (MH)+.

The following examples were prepared similarly:

Example 32

N-(3-Ethylphenyl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea acetate LCMS RT=3.00 min, ES+ve 580 (MH)+.

Example 33

N-{3-[(2-{[6-({(2R)-2-Hydroxy-2-[4-hydroxy-3-(hydroxymethyl)phenyl]ethyl}amino)hexyl]oxy}ethoxy)methyl]phenyl}-N'-(3-methylphenyl)urea acetate LCMS RT=2.73 min, ES+ve 566 (MH)+.

Example 34

N-{3-[(2-{[6-({(2R)-2-Hydroxy-2-[4-hydroxy-3-(hydroxymethyl)phenyl]ethyl}amino)hexyl]oxy}ethoxy)methyl]phenyl}-N'-[3-(trifluoromethyl)phenyl]urea acetate LCMS RT=2.91 min, ES+ve 620 (MH)+.

Example 35

N-(3,5-Dichlorophenyl)-N'-{2-[(2-{[6-({(2R)-2-hydroxy-2-[4-hydroxy-3-(hydroxymethyl)phenyl]ethyl}amino)hexyl]oxy}ethoxy)methyl]phenyl}urea acetate LCMS RT=3.19 min, ES+ve 620, 622, 623 (MH)+.

Example 36

N-(3-Chlorophenyl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea acetate LCMS RT=3.01 min, ES+ve 586, 588 (MH)+.

Example 37

N-{3-[(2-{[6-({(2R)-2-Hydroxy-2-[4-hydroxy-3-(hydroxymethyl)phenyl]-ethyl}amino)hexyl]oxy}ethoxy)methyl]phenyl}-N'-(3-iodophenyl)urea acetate LCMS RT=3.12 min, ES+ve 677 (MH)+.

Example 38

4-{(1R)-2-[(6-{2-[(3-Aminobenzyl)oxy]ethoxy}hexyl)amino]-1-hydroxyethyl}-2-(hydroxymethyl)phenol acetate LCMS RT=4.32 min, ES+ve 433 (MH)+.

Example 39

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}pyridine-3-carboxamide acetate LCMS RT=2.31 min, ES+ve 538 (MH)+.

Example 40

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}thiophene-2-carboxamide acetate LCMS RT=2.69 min, ES+ve 543 (MH)+.

Example 41

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}benzamide acetate LCMS RT=2.72 min, ES+ve 537 (MH)+.

Example 42

3-(Benzoylamino)-N-{3-[(2-{[6-({(2R)-2-hydroxy-2-[4-hydroxy-3-(hydroxymethyl)-phenyl]ethyl}amino)hexyl]oxy}ethoxy)methyl]phenyl}benzamide acetate LCMS RT=2.70 min, ES+ve 656 (MH)+

Example 43

N-{3-[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]phenyl}thiophene-2-carboxamide acetate LCMS RT=2.74 min, ES+ve 662 (MH)+.

Example 44

N-{3-[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]phenyl}nicotinamide acetate (1:2)

LCMS RT=2.51 min, ES+ve 657 (MH)+.

Example 45

N-(3-{[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]amino}phenyl)-benzenesulfonamide LCMS RT=2.80 min, ES+ve 707 (MH)+.

Example 46

4-[(1R)-2-({6-[2-(1,1'-Biphenyl-2-ylmethoxy)ethoxy]hexyl}amino)-1-hydroxyethyl]-2-(hydroxymethyl)phenol acetate LCMS RT=2.77 min, ES+ve 494 (MH)+.

Example 47

4-{(1R)-1-Hydroxy-2-[(6-{2-[(4'-methoxy-1,1'-biphenyl-2-yl)methoxy]ethoxy}-hexyl)amino]ethyl}-2-(hydroxymethyl)phenol acetate LCMS RT=2.79 min, ES+ve 524 (MH)+.

Example 48

4-{(1R)-2-[(6-{2-[(3-Bromobenzyl)oxy]ethoxy}hexyl)amino]-1-hydroxyethyl}-2-(hydroxymethyl)phenol acetate LCMS RT=2.68 min, ES+ve 498 (MH)+.

Example 49

2-(Hydroxymethyl)-4-{(1R)-1-hydroxy-2-[(6-{2-[(3-phenoxybenzyl)oxy]ethoxy}-hexyl)amino]ethyl}phenol acetate LCMS RT=2.85 min, ES+ve 510 (MH)+.

Example 50

4-{(1R)-1-Hydroxy-2-[(6-{2-[(4-hydroxybenzyl)oxy]ethoxy}hexyl)amino]ethyl}-2-(hydroxymethyl)phenol LCMS RT=2.40 min, ES+ve 434 (MH)+.

Example 51

5-{3-[(2-{[6-({(2R)-2-Hydroxy-2-[4-hydroxy-3-(hydroxymethyl)phenyl]ethyl}-amino)hexyl]oxy}ethoxy)methyl]phenyl}pyrimidine-2,4-diol acetate LCMS RT=2.19 min, ES+ve 528 (MH)+.

Example 52

4-{(1R)-2-[(6-{2-[(2,5-Dichlorobenzyl)oxy]ethoxy}hexyl)amino]-1-hydroxyethyl}-2-(hydroxymethyl)phenol acetate LCMS RT=2.86 min, ES+ve 486 (MH)+, 488 (MH)+.

Example 53

4-{(1R)-2-[(6-{2-[(3,5-Dimethylbenzyl)oxy]ethoxy}hexyl)amino]-1-hydroxyethyl}-2-(hydroxymethyl)phenol acetate LCMS RT=2.76 min, ES+ve 446 (MH)+.

Example 54

4-((1R)-2-{[6-(2-{[2-Fluoro-6-(trifluoromethyl)benzyl]oxy}ethoxy)hexyl]amino}-1-hydroxyethyl)-2-(hydroxymethyl)phenol LCMS RT=2.65 min, ES+ve 504 (MH)+.

Example 55

2-(Hydroxymethyl)-4-((1R)-1-hydroxy-2-{[6-(2-{[3-(trifluoromethoxy)benzyl]-oxy}ethoxy)hexyl]amino}ethyl)phenol acetate LCMS RT=2.89 min, ES+ve 502 (MH)$^+$.

Example 56

2-(Hydroxymethyl)-4-{(1R)-1-hydroxy-2-[(6-{2-[(2-methyl-1,1'-biphenyl-3-yl)methoxy]ethoxy}hexyl)amino]ethyl}phenol LCMS RT=2.89 min, ES+ve 508 (MH)$^+$.

Example 57

3-[(2,3-Dihydroimidazo[2,1-b][1,3]thiazol-6-ylmethyl)amino]-N-{3-[(2-{[6-({(2R)-2-hydroxy-2-[4-hydroxy-3-(hydroxymethyl)phenyl]ethyl}amino)hexyl]oxy}ethoxy)-methyl]phenyl}benzamide acetate (1:3)

LCMS RT=2.43 min, ES+ve 690 (MH)$^+$.

Example 58

N-(3-{[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]amino}phenyl)benzamide LCMS RT=2.80 min, ES+ve 671 (MH)$^+$.

Example 59

N-(3-{[({3-[(2-{[6-({(2R)-2-Hydroxy-2-[4-hydroxy-3-(hydroxymethyl)phenyl]ethyl}-amino)hexyl]oxy}ethoxy)methyl]phenyl}amino)carbonyl]amino}phenyl)thiophene-2-carboxamide LCMS RT=2.80 min, ES+ve 677 (MH)$^+$.

Example 60

N-(1,1'-Biphenyl-3-yl)-N'-{3-[(2-{[6-({(2R)-2-hydroxy-2-[4-hydroxy-3-(hydroxymethyl)phenyl]ethyl}amino)hexyl]oxy}ethoxy)methyl]phenyl}urea LCMS RT=3.20 min, ES+ve 628 (MH)$^+$.

Example 61

N-(3-Aminophenyl)-N'-{3-[(2-{[6-({(2R)-2-hydroxy-2-[4-hydroxy-3-(hydroxy-methyl)phenyl]ethyl}amino)hexyl]oxy}ethoxy)methyl]phenyl}urea acetate LCMS RT=2.38 min, ES+ve 567 (MH)$^+$.

Example 62

3-[(2-{[6-({(2R)-2-Hydroxy-2-[4-hydroxy-3-(hydroxymethyl)phenyl]ethyl}amino)-hexyl]oxy}ethoxy)methyl]-N-methylbenzenesulfonamide compound with (2E)-but-2-enedioic acid (2:1)

LCMS RT=2.25 min, ES+ve 511 (MH)$^+$.

Example 63

N-{3-[(2-{[6-({(2R)-2-Hydroxy-2-[4-hydroxy-3-(hydroxymethyl)phenyl]ethyl}-amino)hexyl]oxy}ethoxy)methyl]phenyl}-3-[(thien-2-ylsulfonyl)amino]benzamide compound with (2E)-but-2-enedioic acid (2:1)

LCMS RT=min, 2.72ES+ve 698 (MH)$^+$.

Example 64

N-{3-[(2-{[5-({(2R)-2-Hydroxy-2-[4-hydroxy-3-(hydroxymethyl)phenyl]ethyl}amino)pentyl]oxy}ethoxy)methyl]phenyl}-N'-phenylurea acetate i) 1-({2-[(5-Bromopentyl)oxy]ethoxy}methyl)-3-nitrobenzene The title compound was prepared by a procedure similar to that described in example 21 ii). LCMS RT=3.42 min ii (5R)-5-(2,2-Dimethyl-4H-1,3-benzodioxin-6-yl)-3-(5-{2-[(3-nitrobenzyl)oxy]ethoxy}pentyl)-1,3-oxazolidin-2-one The title compound was prepared by a procedure similar to that described in example 21 iii). LCMS RT=3.46 min iii (5R)-3-(5-{2-[(3-Aminobenzyl)oxy]ethoxy}pentyl)-5-(2,2-dimethyl-4H-1,3-benzodioxin-6-yl)-1,3-oxazolidin-2-one The title compound was prepared by a procedure similar to that described in example 21 iv). LCMS RT=3.13 min iv) N-(3-{[2-({5-[(5R)-5-(2,2-Dimethyl-4H-1,3-benzodioxin-6-yl)-2-oxo-1,3-oxazolidin-3-yl]pentyl}oxy)ethoxy]methyl}phenyl)-N'-phenylurea The title compound was prepared by a procedure similar to that described in example 21 v). LCMS RT=3.58 min v) N-[3-({2-[(5-{[(2R)-2-(2,2-Dimethyl-4H-1,3-benzodioxin-6-yl)-2-hydroxyethyl]amino}pentyl)oxy]ethoxy}methyl)phenyl]-N'-phenylurea The title compound was prepared by a procedure similar to that described in example 1 xii). LCMS RT=2.79 min vi) N-{3-[(2-{[5-({(2R)-2-Hydroxy-2-[4-hydroxy-3-(hydroxymethyl)phenyl]ethyl}amino)pentyl]oxy}ethoxy)methyl]phenyl}-N'-phenylurea acetate The title compound was prepared by a procedure similar to that described in example 1 xiii). LCMS RT=2.42 min, ES+ve 538 (MH)$^+$

Example 65

N-{3-[(3-{[5-({(2R)-2-Hydroxy-2-[4-hydroxy-3-(hydroxymethyl)phenyl]ethyl}amino)pentyl]oxy}propoxy)methyl]phenyl}-N'-phenylurea acetate i) 3-[(3-Nitrobenzyl)oxy]propan-1-ol The title compound was prepared by a procedure similar to that described in example 21 i). TSP+ve 229 (MH)$^+$ ii 1-({3-[(5-Bromopentyl)oxy]propoxy}methyl)-3-nitrobenzene The title compound was prepared by a procedure similar to that described in example 21 ii). LCMS RT=3.80 min iii) 5R)-5-(2,2-Dimethyl-4H-1,3-benzodioxin-6-yl)-3-(5-{3-[(3-nitrobenzyl)oxy]propoxy}pentyl)-1,3-oxazolidin-2-one The title compound was prepared by a procedure similar to that described in example 21 iii) LCMS RT=3.57 min iv) (5R)-3-(5-{3-[(3-Aminobenzyl)oxy]propoxy}pentyl)-5-(2,2-dimethyl-4H-1,3-benzodioxin-6-yl)-1,3-oxazolidin-2-one The title compound was prepared by a procedure similar to that described in example 21 iv). LCMS RT=3.21 min v) N-(3-{[3-({5-[(5R)-5-(2,2-Dimethyl-4H-1,3-benzodioxin-6-yl)-2-oxo-1,3-oxazolidin-3-yl]pentyl}oxy)propoxy]methyl}phenyl)-N'-phenylurea The title compound was prepared by a procedure similar to that described in example 21 v). LCMS RT=3.62 min vi) N-[3-({3-[(5-{[(2R)-2-(2,2-Dimethyl-4H-1,3-benzodioxin-6-yl)-2-hydroxyethyl]amino}pentyl)oxy]propoxy}methyl)phenyl]-N'-phenylurea The title compound was prepared by a procedure similar to that described in example 1 xii). LCMS RT=2.94 min vii) N-{3-[(3-{[5-({(2R)-2-Hydroxy-2-[4-hydroxy-3-(hydroxymethyl)phenyl]ethyl}amino)pentyl]oxy}propoxy)methyl]phenyl}-N'-phenylurea acetate The title compound was prepared by a procedure similar to that described in example 1 xiii). LCMS RT=2.50 min, ES+ve 552 (MH)$^+$

Example 66

N-{3-[(2-{[7-({(2R)-2-Hydroxy-2-[4-hydroxy-3-(hydroxymethyl)phenyl]ethyl}amino)heptyl]oxy}ethoxy)methyl]phenyl}-N'-phenylurea acetate i) 1-({2-[(7-Bromoheptyl)oxy]ethoxy}methyl)-3-nitrobenzene The title compound was prepared by a procedure similar to that described in example 21 ii). LCMS RT=3.83 min ii) (5R)-5-(2,2-Dimethyl-4H-1,3-benzodioxin-6-yl)-3-(7-{2-[(3-nitrobenzyl)oxy]ethoxy}heptyl)-1,3-oxazolidin-2-one The title compound was prepared by a procedure similar to that described in example 21 iii). LCMS RT=3.67 min iii) (5R)-3-(7-{2-[(3-Aminobenzyl)oxy]ethoxy}heptyl)-5-(2,2-dimethyl-4H-1,3-benzodioxin-6-yl)-1,3-oxazolidin-2-one The title compound was prepared by a procedure similar to that described in example 21 iv). LCMS RT=3.40 min iv) N-(3-{[2-({7-[(5R)-5-(2,2-Dimethyl-4H-1,3-benzodioxin-6-yl)-2-oxo-1,3-oxazolidin-3-yl]heptyl}oxy)ethoxy]methyl}phenyl)-N'-phenylurea The title compound was prepared by a procedure similar to that described in example 21 v). LCMS RT=3.74 min v) N-[3-({2-[(7-{[(2R)-2-(2,2-Dimethyl-4H-1,3-benzodioxin-6-yl)-2-hydroxyethyl]amino}heptyl)oxy]ethoxy}methyl)phenyl]-N'-phenylurea The title compound was prepared by a procedure similar to that described in example 1 xii). LCMS RT=2.91 min vii) N-{3-[(2-{[7-({(2R)-2-Hydroxy-2-[4-hydroxy-3-(hydroxymethyl)phenyl]ethyl}amino)heptyl]oxy}ethoxy)methyl]phenyl}-N'-phenylurea acetate The title compound was prepared by a procedure similar to that described in example 1 xiii). LCMS RT=2.58 min, ES+ve 566 (MH)$^+$

Example 67

N-(3-{[({3-[(2-{[5-({(2R)-2-Hydroxy-2-[4-hydroxy-3-(hydroxymethyl)phenyl]ethyl}amino)pentyl]oxy}ethoxy)methyl]phenyl}amino)carbonyl]amino}phenyl)nicotinamide acetate i) N-(3-{[2-({5-[(5R)-5-(2,2-Dimethyl-4H-1,3-benzodioxin-6-yl)-2-oxo-1,3-oxazolidin-3-yl]pentyl}oxy)ethoxy]methyl}phenyl)-N'-(3-nitrophenyl)urea The title compound was prepared by a procedure similar to that described in example 21 v) using 3-nitrophenyl isocyanate and purified using Biotage eluting with DCM-MeOH (50:1). LCMS RT=3.67 min ii) N-(3-Aminophenyl)-N'-(3-{[2-({5-[(5R)-5-(2,2-dimethyl-4H-1,3-benzodioxin-6-yl)-2-oxo-1,3-oxazolidin-3-yl]pentyl}oxy)ethoxy]methyl}phenyl)urea The title compound was prepared by a procedure similar to that described in example 21 iv). LCMS RT=3.22 min iii) N-[3-({[(3-{[2-({5-[(5R)-5-(2,2-Dimethyl-4H-1,3-benzodioxin-6-yl)-2-oxo-1,3-oxazolidin-3-yl]pentyl}oxy)ethoxy]methyl}phenyl)amino]carbonyl}amino)phenyl]nicotinamide The title compound was prepared by a procedure similar to that described in example 21 vii). LCMS RT=3.38 min iv) N-{3-[({[3-({2-[(5-{[(2R)-2-(2,2-Dimethyl-4H-1, 3-benzodioxin-6-yl)-2-hydroxyethyl]amino}pentyl) oxy]ethoxy}methyl)phenyl]amino}carbonyl)amino] phenyl}nicotinamide The title compound was prepared by a procedure similar to that described in example 21 vii). It was purified using Prep. TLC (silica, 1 mm thick, 20×20 cm) eluting with DCM-EtOH: aqueous ammonia S.G. 0.880 (100:8:1) to yield the title compound (83 mg).
LCMS RT=2.73 min v) N-(3-{[({3-[(2-{[5-({(2R)-2-Hydroxy-2-[4-hydroxy-3-(hydroxymethyl)phenyl]ethyl}amino)pentyl]oxy}ethoxy)methyl]phenyl}amino)carbonyl] amino}phenyl)nicotinamide acetate The title compound was prepared by a procedure similar to that described in example 21 viii) LCMS RT=2.45 min, ES+ve 658 (MH)+

Example 68

N-(3-{[({3-[(3-{[5-({(2R)-2-Hydroxy-2-[4-hydroxy-3-(hydroxymethyl)phenyl]ethyl}amino)pentyl] oxy}propoxy)methyl]phenyl}amino)carbonyl] amino}phenyl)nicotinamide acetate i) N-(3-{[3-({5-[(5R)-5-(2,2-Dimethyl-4H-1,3-benzodioxin-6-yl)-2-oxo-1,3-oxazolidin-3-yl] pentyl}oxy)propoxy]methyl}phenyl)-N'-(3-nitrophenyl)urea The title compound was prepared by a procedure similar to that described in example 21 v). LCMS RT=3.75 min ii) N-(3-Aminophenyl)-N'-(3-{[3-({5-[(5R)-5-(2,2-dimethyl-4H-1,3-benzodioxin-6-yl)-2-oxo-1,3-oxazolidin-3-yl]pentyl}oxy)propoxy]methyl}phenyl) urea The title compound was prepared by a procedure similar to that described in example 21 iv). LCMS RT=3.31 min iii) N-[3-({[(3-{[3-({5-[(5R)-5-(2,2-Dimethyl-4H-1, 3-benzodioxin-6-yl)-2-oxo-1,3-oxazolidin-3-yl] pentyl}oxy)propoxy]methyl}phenyl)amino] carbonyl}amino)phenyl]nicotinamide The title compound was prepared by a procedure similar to that described in example 21 vii). LCMS RT=3.46 min iv) N-{3-[({[3-({3-[(5-{[(2R)-2-(2,2-Dimethyl-4H-1, 3-benzodioxin-6-yl)-2-hydroxyethyl]amino}pentyl) oxy]propoxy}methyl)phenyl]amino}carbonyl) amino]phenyl}nicotinamide The title compound was prepared by a procedure similar to that described in example 21 viii) LCMS RT=2.80 min
v) N-(3-{[({3-[(3-{[5-({(2R)-2-Hydroxy-2-[4-hydroxy-3-(hydroxymethyl)phenyl]ethyl}amino)pentyl]oxy}propoxy) methyl]phenyl}amino)carbonyl]amino}phenyl)nicotinamide acetate
The title compound was prepared by a procedure similar to that described in example 1 xiii). LCMS RT=2.51 min, ES+ve 672 (MH)+

Example 69

N-(3-{[({3-[(3-{[7-({(2R)-2-Hydroxy-2-[4-hydroxy-3-(hydroxymethyl)phenyl]ethyl}amino)heptyl] oxy}propoxy)methyl]phenyl}amino)carbonyl] amino}phenyl)nicotinamide acetate i) N-(3-{[3-({7-[(5R)-5-(2,2-Dimethyl-4H-1,3-benzodioxin-6-yl)-2-oxo-1,3-oxazolidin-3-yl] heptyl}oxy)propoxy]methyl}phenyl)-N'-(3-nitrophenyl)urea The title compound was prepared by a procedure similar to that described in example 21 v). LCMS RT=3.84 min ii) N-(3-Aminophenyl)-N'-(3-{[3-({7-[(5R)-5-(2,2-dimethyl-4H-1,3-benzodioxin-6-yl)-2-oxo-1,3-oxazolidin-3-yl]heptyl}oxy)propoxy]methyl}phenyl) urea The title compound was prepared by a procedure similar to that described in example 21 iv). LCMS RT=3.44 min iii) N-[3-({[(3-{[3-({7-[(5R)-5-(2,2-Dimethyl-4H-1, 3-benzodioxin-6-yl)-2-oxo-1,3-oxazolidin-3-yl] heptyl}oxy)propoxy]methyl}phenyl)amino] carbonyl}amino)phenyl]nicotinamide The title compound was prepared by a procedure similar to that described in example 21 vii). LCMS RT=3.57 min iv) N-{3-[({[3-({3-[(7-{[(2R)-2-(2,2-Dimethyl-4H-1, 3-benzodioxin-6-yl)-2-hydroxyethyl]amino}heptyl) oxy]propoxy}methyl)phenyl]amino}carbonyl) amino]phenyl}nicotinamide The title compound was prepared by a procedure similar to that described in example 21 viii). LCMS RT=2.83 min v) N-(3-{[({3-[(3-{[7-({(2R)-2-Hydroxy-2-[4-hydroxy-3-(hydroxymethyl)phenyl]ethyl}amino)heptyl]oxy}propoxy)methyl]phenyl}amino)carbonyl] amino}phenyl)nicotinamide acetate The title compound was prepared by a procedure similar to that described in example 1 xiii). LCMS RT=2.58 min, ES+ve 686 (MH)+

Example 70

N-{3-[(2-{[5-({(2R)-2-Hydroxy-2-[4-hydroxy-3-(hydroxymethyl)phenyl]ethyl}amino)pentyl] oxy}ethoxy)methyl]phenyl}methanesulfonamide acetate i) N-(3-{[2-({5-[(5R)-5-(2,2-Dimethyl-4H-1,3-benzodioxin-6-yl)-2-oxo-1,3-oxazolidin-3-yl] pentyl}oxy)ethoxy]methyl}phenyl)methanesulfonamide A solution of (5R)-3-(5-{2-[(3-aminobenzyl)oxy] ethoxy}pentyl)-5-(2,2-dimethyl-4H-1,3-benzodioxin-6-yl)-1,3-oxazolidin-2-one (52 mg) in pyridine (4 ml) was treated with methanesulfonyl chloride (13 mg) at 20° C. for 3 h. The mixture was quenched with sat. aqueous sodium bicarbonate (20 ml) and partitioned with DCM. The organic layer was dried (Na$_2$SO$_4$) and the solvent was removed in vacuo. The residue was purified using SPE eluting with DCM then EtOAc-PE (3:1). The selected fractions were evaporated in vacuo to yield the title compound (39 mg).
LCMS RT=3.29 min ii) N-[3-({2-[(5-{[(2R)-2-(2,2-Dimethyl-4H-1,3-benzodioxin-6-yl)-2-hydroxyethyl]amino}pentyl)oxy]ethoxy}methyl)phenyl]methanesulfonamide The title compound was prepared by a procedure similar to that described in example 1 xii). LCMS RT=2.53 min iii) N-{3-[(2-{[5-({(2R)-2-2-Hydroxy-2-[4-hydroxy-3-(hydroxymethyl)phenyl]ethyl}amino)pentyl]oxy}ethoxy)methyl]phenyl}methanesulfonamide acetate The title compound was prepared by a procedure similar to that described in example 1 xiii). LCMS RT=2.12 min, ES+ve 497 (MH)+

Example 71

N-{3-[(3-{[5-({(2R)-2-Hydroxy-2-[4-hydroxy-3-(hydroxymethyl)phenyl]ethyl}amino)pentyl]oxy}propoxy)methyl]phenyl}methanesulfonamide acetate i) 1-({3-[(5-Bromopentyl)oxy]propoxy}methyl)-3-nitrobenzene The title compound was prepared by a procedure similar to that described in example 24 ii). LCMS RT=3.80 min ii) (5R)-5-(2,2-Dimethyl-4H-1,3-benzodioxin-6-yl)-3-(5-{3-[(3-nitrobenzyl)oxy]propoxy}pentyl)-1,3-oxazolidin-2-one The title compound was prepared by a procedure similar to that described in example 21 iii). LCMS RT=3.57 min iii) (5R)-3-(5-{2-[(3-Aminobenzyl)oxy]ethoxy}pentyl)-5-(2,2-dimethyl-4H-1,3-benzodioxin-6-yl)-1,3-oxazolidin-2-one The title compound was prepared by a procedure similar to that described in example 21 iv). LCMS RT=3.21 min iv) N-(3-{[3-({5-[(5R)-5-(2,2-Dimethyl-4H-1,3-benzodioxin-6-yl)-2-oxo-1,3-oxazolidin-3-yl]pentyl}oxy)propoxy]methyl}phenyl)methanesulfonamide The title compound was prepared by a procedure similar to that described in example 70 i) purified using Biotage eluting with EtOAc-PE (3:1).
LCMS RT=3.26 min v) N-[3-({3-[(5-{[(2R)-2-(2,2-Dimethyl-4H-1,3-benzodioxin-6-yl)-2-hydroxyethyl]amino}pentyl)oxy]propoxy}methyl)phenyl]methanesulfonamide The title compound was prepared by a procedure similar to that described in example 1 xii). LCMS RT=2.57 min vi) N-{3-[(3-{[5-({(2R)-2-Hydroxy-2-[4-hydroxy-3-(hydroxymethyl)phenyl]ethyl}amino)pentyl]oxy}propoxy)methyl]phenyl}methanesulfonamide acetate The title compound was prepared by a procedure similar to that described in example 1 xiii). LCMS RT=2.20 min Example 72

N-{3-[(2-{[7-({(2R)-2-Hydroxy-2-[4-hydroxy-3-(hydroxymethyl)phenyl]ethyl}amino)heptyl]oxy}ethoxy)methyl]phenyl}methanesulfonamide acetate i) N-(3-{[2-({7-[(5R)-5-(2,2-Dimethyl-4H-1,3-benzodioxin-6-yl)-2-oxo-1,3-oxazolidin-3-yl]heptyl}oxy)ethoxy]methyl}phenyl)methanesulfonamide The title compound was prepared by a procedure similar to that described in example 70 i). LCMS RT=3.48 min ii) N-[3-({2-[(7-{[(2R)-2-(2,2-Dimethyl-4H-1,3-benzodioxin-6-yl)-2-hydroxyethyl]amino}heptyl)oxy]ethoxy}methyl)phenyl]methanesulfonamide The title compound was prepared by a procedure similar to that described in example 1 xii). LCMS RT=2.69 min iii) N-{3-[(2-{[7-({(2R)-2-Hydroxy-2-[4-hydroxy-3-(hydroxymethyl)phenyl]ethyl}amino)heptyl]oxy}ethoxy)methyl]phenyl}methanesulfonamide acetate The title compound was prepared by a procedure similar to that described in example 1 xiii). LCMS RT=2.28 min, ES+ve 525 (MH)+

Example 73

N-{3-[(2-{[6-({(2R)-2-Hydroxy-2-[4-hydroxy-3-(hydroxymethyl)phenyl]ethyl}amino)hexyl]oxy}ethoxy)methyl]phenyl}benzenesulfonamide acetate i) N-(3-{[2-({6-[(5R)-5-(2,2-Dimethyl-4H-1,3-benzodioxin-6-yl)-2-oxo-1,3-oxazolidin-3-yl]hexyl}oxy)ethoxy]methyl}phenyl)benzenesulfonamide The title compound was prepared by a procedure similar to that described in example 70 i) using benzenesulfonyl chloride and purified using SPE and eluting with DCM-MeOH (300:1) then at 100:1. LCMS RT=3.51 min ii) N-{3-[(2-{[6-({(2R)-2-Hydroxy-2-[4-hydroxy-3-(hydroxymethyl)phenyl]ethyl}amino)hexyl]oxy}ethoxy)methyl]phenyl}benzenesulfonamide acetate The title compound was prepared by a procedure similar to that described in example 1 xii). The product was purified using SCX-2 cartridge eluting with EtOH then EtOH-2M ammonia in MeOH (9:1). The resulting residue after solvent evaporation was further purified using SPE eluting with DCM then varying ratios of DCM-EtOH-aqueous ammonia S.G.

0.880. The selected fractions were evaporated in vacuo to yield the freebase. This was dissolved in AcOH (4 ml) then azeotroped with MeOH (3×8 ml) to yield the title compound (214 mg). LCMS RT=2.50 min, ES+ve 573 (MH)+

Example 74

4-((1R)-2-{[6-(2-{[3-(Dimethylamino)benzyl]oxy}ethoxy)hexyl]amino}-1-hydroxyethyl)-2-(hydroxymethyl)phenol i) (5R)-3-[6-(2-{[3-(Dimethylamino)benzyl]oxy}ethoxy)hexyl]-5-(2,2-dimethyl-4H-1,3-benzodioxin-6-yl)-1,3-oxazolidin-2-one A solution of 3-dimethylaminobenzyl alcohol (641 mg) in DMF (3 ml) under nitrogen was treated with sodium hydride (220 mg, 60% in oil) and the mixture stirred at 20° for 15 min. A solution of 2-({6-[(5R)-5-(2,2-dimethyl-4H-1,3-benzodioxin-6-yl)-2-oxo-1,3-oxazolidin-3-yl]hexyl}oxy)ethyl methanesulfonate (2.00 g) in DMF (5 ml) was added and the mixture was stirred at 20° for 21 h. Phosphate buffer solution (15 ml, pH6.5) was added, the mixture stirred for 15 min and then extracted with EtOAc. The combined organic layers were washed with water, dried (Na$_2$SO$_4$) and the solvent evaporated in vacuo. The residue was purified by Biotage (40 g). Elution with EtOAc-PE (1:2) gave the title compound (2.125 g). LCMS RT=3.47 min.

ii) (1R)-2-{[6-(2-{[3-(Dimethylamino)benzyl]oxy}ethoxy)hexyl]amino}-1-(2,2-dimethyl-4H-1,3-benzodioxin-6-yl)ethanol The title compound was prepared by a procedure similar to that described in Example 1 xii). LCMS RT=2.38 min.

iii) 4-((1R)-2-{[6-(2-{[3-(dimethylamino)benzyl]oxy}ethoxy)hexyl]amino}-1-hydroxyethyl)-2-(hydroxymethyl)phenol The title compound was prepared by a procedure similar to that described in Example 1 xiii). LCMS RT=2.17 min, ES+ve 461 (MH)+

Example 75

3-[(2-{[6-({(2R)-2-Hydroxy-2-[4-hydroxy-3-(hydroxymethyl)phenyl]ethyl}amino)hexyl]oxy}ethoxy)methyl]-N,N,N-trimethylbenzenaminium acetate compound with acetic acid (1:1)

i) Benzyl 6-(2-{[3-(dimethylamino)benzyl]oxy}ethoxy)hexyl[(2R)-2-(2,2-dimethyl-4H-1,3-benzodioxin-6-yl)-2-hydroxyethyl]carbamate A solution of (1R)-2-{[6-(2-{[3-(dimethylamino)benzyl]oxy}ethoxy)hexyl]amino}-1-(2,2-dimethyl-4H-1,3-benzodioxin-6-yl)ethanol (200 mg) in dichloromethane (10 ml) was treated under nitrogen with diisopropylethylamine (0.09 ml) followed by benzyl chloroformate (0.099 ml) and the mixture was stirred at 20° for 4 h. Saturated sodium bicarbonate solution was added and the mixture extracted with dichloromethane. The extract was dried (Na$_2$SO$_4$) and the solvent evaporated in vacuo. The residue was purified by SPE (silica, 10 g). Elution with dichloromethane-ethanol-0.880 ammonia (250:8:1) gave the title compound (220 mg). LCMS RT=3.87 min.

ii) 3-{12-[(2R)-2-(2,2-Dimethyl-4H-1,3-benzodioxin-6-yl)-2-hydroxyethyl]-13-oxo-15-phenyl-2,5,14-trioxa-12-azapentadec-1-yl}-N,N,N-trimethylbenzenaminium iodide A solution of benzyl 6-(2-{[3-(dimethylamino)benzyl]oxy}ethoxy)hexyl[(2R)-2-(2,2-dimethyl-4H-1,3-benzodioxin-6-yl)-2-hydroxyethyl]carbamate (571 mg) in DMF (9 ml) was treated with iodomethane (0.09 ml) and the mixture was stirred 20° for 16 h. The solvent was evaporated in vacuo and the residue was purified by SPE (silica, 10 g). Elution with methanol-0.880 ammonia (19:1) gave the title compound (346 mg). LCMS RT=2.79 min.

iii) 3-({2-[(6-{[(2R)-2-(2,2-Dimethyl-4H-1,3-benzodioxin-6-yl)-2-hydroxyethyl]amino}hexyl)oxy]ethoxy}methyl)-N,N,N-trimethylbenzenaminium iodide A solution of 3-{12-[(2R)-2-(2,2-dimethyl-4H-1,3-benzodioxin-6-yl)-2-hydroxyethyl]-13-oxo-15-phenyl-2,5,14-trioxa-12-azapentadec-1-yl}-N,N,N-trimethylbenzenaminium iodide (195 mg) in ethanol (15 ml) was hydrogenated over 10% palladium on carbon (194 mg) for 5 h. The mixture was filtered through celite and the solvent evaporated in vacuo. The residue was purified by mass directed autopreparative HPLC to give the title compound (7 mg). LCMS RT=2.13 min.

iv) 3-[(2-{[6-({(2R)-2-Hydroxy-2-[4-hydroxy-3-(hydroxymethyl)phenyl]ethyl}amino)hexyl]oxy}ethoxy)methyl]-N,N,N-trimethylbenzenaminium acetate compound with acetic acid (1:1)

The title compound was prepared by a procedure similar to that described in Example 1 xiii). LCMS RT=1.87 min, ES+ve 475 M+

Example 76

N-{4-[(2-{[6-({(2R)-2-Hydroxy-2-[4-hydroxy-3-(hydroxymethyl)phenyl]ethyl}amino)hexyl]oxy}ethoxy)methyl]phenyl}-N'-phenylurea acetate i) (5R)-3-(6-{2-[(4-Bromobenzyl)oxy]ethoxy}hexyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-{6-[(2-hydroxyethyl)oxy]hexyl}-1,3-oxazolidin-2-one (2.00 g) in DMF (25 ml) under nitrogen was treated with sodium hydride (244 mg, 60% in oil) and the mixture was stirred at 20° for 15 min. 4-Bromobenzyl bromide (1.40 g) was added and the mixture was stirred at 20° for 18 h. Phosphate buffer solution (50 ml, pH6.5) and water (50 ml) were added and the mixture was extracted with EtOAc. The extract was washed with water, dried (Na$_2$SO$_4$) and the solvent evaporated in vacuo to give a residue. The residue was purified by chromatography on flash silica gel (40 mm diameter column). Elution with EtOAc-PE (1:1) gave the title compound (2.125 g). LCMS RT=3.77 min.

ii) (5R)-5-(2,2-Dimethyl-4H-1,3-benzodioxin-6-yl)-3-{6-[2-({4-[(diphenylmethylene)amino]benzyl}oxy)ethoxy]hexyl}-1,3-oxazolidin-2-one A mixture of palladium (II) acetate (40 mg), racemic-2,2'-bis(diphenylphosphino)-1,1'-binaphthyl (166 mg) and cesium carbonate (811 mg) under nitrogen was treated with toluene (15 ml) and benzophenone imine (0.36 ml) followed by a solution of (5R)-3-(6-{2-[(4-bromobenzyl)oxy]ethoxy}hexyl)-5-(2,2-dimethyl-4H-1,3-benzodioxin-6-yl)-1,3-oxazolidin-2-one (1.00 g) in toluene (10 ml). The stirred mixture was heated to 100° for 18 h. The mixture was cooled to 20°, dichloromethane (25 ml) was added and the mixture was filtered. The filtrate was evaporated in vacuo and the residue purified by chromatography on flash silica gel (30 mm diameter column). Elution with EtOAc-PE (3:2) gave the title compound (890 mg). LCMS RT=4.07 min.

iii) (5R)-3-(6-{2-[(4-Aminobenzyl)oxy]ethoxy}hexyl)-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-{6-[2-({4-[(diphenylmethylene)amino]benzyl}oxy)ethoxy]hexyl}-1,3-oxazolidin-2-one (860 mg) in MeOH (13 ml) was treated with sodium acetate (255 mg) followed by hydroxylamine hydrochloride (162 mg) and the mixture was stirred at 20° for 0.5 h. Phosphate buffer solution (30 ml, pH6.5) was added and the mixture was extracted with EtOAc. The combined extracts were dried (Na$_2$SO$_4$) and the solvent evaporated in vacuo. The residue was purified by SPE (silica, 10 g). Elution with EtOAc-cyclohexane (1:1) then (4:1) gave the title compound (321 mg). LCMS RT=3.18 min.

iv) N-(4-{[2-({6-[(5R)-5-(2,2-Dimethyl-4H-1,3-benzodioxin-6-yl)-2-oxo-1,3-oxazolidin-3-yl]hexyl}oxy)ethoxy]methyl}phenyl)-N'-phenylurea A solution of (5R)-3-(6-{2-[(4-aminobenzyl)oxy]ethoxy}hexyl)-5-(2,2-dimethyl-4H-1,3-benzodioxin-6-yl)-1,3-oxazolidin-2-one (150 mg) in dichloromethane (5 ml) under nitrogen was treated with phenyl isocyanate (0.07 ml) and the mixture stirred at 20° for 5 h. Isopropyl alcohol (5 ml) was added and the solution was stirred for a further 18 h. The solvent was evaporated in vacuo and the residue purified by SPE (silica, 10 g). Elution with EtOAc-cyclohexane (3:7) then EtOAc gave the title compound (159 mg). LCMS RT=3.68 min.

v) N-[4-({2-[(6-{[(2R)-2-(2,2-Dimethyl-4H-1,3-benzodioxin-6-yl)-2-hydroxyethyl]amino}hexyl)oxy]ethoxy}methyl)phenyl]-N'-phenylurea The title compound was prepared by a procedure similar to that described in Example 1 xii). LCMS RT=3.68 min.

vi) N-{4-[(2-{[6-({(2R)-2-Hydroxy-2-[4-hydroxy-3-(hydroxymethyl)phenyl]ethyl}amino)hexyl]oxy}ethoxy)methyl]phenyl}-N'-phenylurea acetate The title compound was prepared by a procedure similar to that described in Example 1 xiii). LCMS RT=2.54 min, ES+ve 552 (MH)$^+$ Example 77

4-((R)-2-{6-[2-(2,6-Dichlorobenzyloxy)-ethoxy]-hexylamino}-1-hydroxyethyl)-2-hydroxymethyl-phenol i) 2-(2,6-Dichlorobenzyloxy)ethanol Sodium methoxide (104.4 g, 1.93 mol) was added portionwise to ethylene glycol (3.74 L) under N$_2$, keeping the temperature below 35° C. After 1-2 h, 2,6-dichlorobenzylbromide (400 g, 1.67 mol) was added and the mixture heated to 55-60° C. for 1 h. On cooling to 20° C. water (2.14 L) was added and the mixture extracted with ethyl acetate (2.14 L). The aqueous layer was separated and extracted twice with ethyl acetate (2.14 L, 1.28 L). The combined organic extracts were washed with water (2.14 L) then evaporated to dryness to afford a colourless oil (371.8 g)—LC RT=4 min. This may be chromatographed on silica (Biotage) eluting with 10% ethyl acetate in 60/80 petrol to afford the title compound.
$^1$H NMR (500 MHz, CDCl$_3$) δ 7.33 (d, 2H, J=8.2 Hz), 7.20 (t, 1H, J=8.2 Hz), 4.83 (s, 2H), 3.75 (m, 2H), 3.68 (m, 2H), 2.18 (t, 1H, J=6.3 Hz)

ii) 2-[2-(6-Bromo-hexyloxy)-ethoxymethyl]-1,3-dichloro-benzene

50% aq NaOH (1.89 L), 2-(2,6-dichlorobenzyloxy)ethanol (473.2 g), 1,6-dibromohexane (2.44 kg, 5eq) and tetrabutylammonium bromide (34.1 g, 5 mol %) in toluene (1.89 L) was heated to 55-60° C. for 8-20 h. On cooling water (558 mL) and toluene (558 mL) were added. The aqueous phase was separated and diluted with water (1 L) then back extracted with toluene (1.1 L). The combined toluene extracts were washed twice with water (2.2 L), then evaporated to dryness on a rotary evaporator. The excess 1,6-dibromohexane was removed using a wiped film evaporator, and the resulting crude product chromatographed on silica (5 kg Biotage), eluting with 5% ethyl acetate in petrol 60/80, to give the title compound (503.2 g)—LC RT=7.0 min.

iii) (R)-3-{6-[2-(2,6-Dichlorobenzyloxy)-ethoxy]-hexyl}-5-(2,2-dimethyl-4H-benzo[1,3]dioxin-6-yl)-oxazolidin-2-one Potassium tert-butoxide (4.38 g, 39 mmol) was added to a solution of (5R)-5-(2,2-dimethyl-4H-1,3-benzodioxin-6-yl)-1,3-oxazolidin-2-one (9.3 g, 39 mmol) in anhydrous DMF (100 mL) under N$_2$ and the reaction stirred for 1 h at ambient temperature. A solution of 2-[2-(6-bromo-hexyloxy)-ethoxymethyl]-1,3-dichloro-benzene (15 g, 39 mmol) in anhydrous DMF (25 mL) was added and the reaction allowed to stir at ambient temperature for 20 h. The reaction mixture was poured into ice/water (350 mL) and extracted with ethyl acetate (300 mL). The organic layer was separated then washed successively with water/saturated brine (250 mL/25 mL), water/brine (25 mL/10 mL) and finally brine (150 mL), before drying over sodium sulfate. The solution was concentrated to dryness under vacuum to afford the title compound as an oil (21.6 g)—LC RT=6.8 min.

iv) (R)-2-{6-[2-(2,6-Dichlorobenzyloxy)-ethoxy]-hexylamino}-1-(2,2-dimethyl-4H-benzo[1,3]dioxin-6-yl)-ethanol The title compound was prepared by a procedure similar to that described in Example 4 (ii).

(v) 4-((R)-2-{6-[2-(2,6-Dichlorobenzyloxy)-ethoxy]-hexylamino}-1-hydroxyethyl)-2-hydroxymethyl-phenol 1N HCl (295 mL) was added to a solution of (R)-2-{6-[2-(2,6-dichlorobenzyloxy)-ethoxy]-hexylamino}-1-(2,2-dimethyl-4H-benzo[1,3]dioxin-6-yl)-ethanol (52 g, 0.099 mol) in ethanol (312 mL), and the reaction stirred at ambient temperature for 1.5 h. Saturated sodium bicarbonate solution (500 mL) was added followed by dichloromethane (500 mL). The aqueous layer was separated and extracted with further dichloromethane (500 mL). The combined organic solutions were washed with water/brine mixture (500 mL/100 mL), then evaporated. The residue (50 g) was chromatographed on silica (800 g, Biotage) eluting with a dichloromethane/ethanol/ammonia mixture (50/8/1), to afford the title compound as an oil (35.2 g)—LC RT=4.1 min.

$^1$H NMR (300 MHz, MeOH-$d_4$) δ 7.47 (m, 2H), 7.38 (m, 2H), 7.19 (dd, 1H, J=8.3, 2.3 Hz), 6.84 (d, 1H, J=8.3 Hz), 4.90 (s, 2H), 4.78 (dd, 1H, J=8.7, 4.5 Hz), 4.74 (s, 2H), 3.78 (m, 2H), 3.68 (m, 2H), 3.55 (t, 2H, J=6.4 Hz), 2.87 (dd, 1H, J=12.1, 8.7 Hz), 2.79 (dd, 1H, J=12.1, 4.5 Hz), 2.69 (m, 2H), 1.63 (m, 4H), 1.44 (m, 4H)

Example 78

Salts of 4-((R)-2-{6-[2-(2,6-Dichlorobenzyloxy)-ethoxy]-hexylamino}-1-hydroxyethyl)-2-hydroxymethyl-phenol i) Triphenylacetate Salt

Triphenylacetic acid (1.81 g, 1eq) was added to a solution of 4-((R)-2-{6-[2-(2,6-dichlorobenzyloxy)-ethoxy]-hexylamino}-1-hydroxyethyl)-2-hydroxymethyl-phenol (3.28 g) in ethanol (20 mL) and the mixture heated to 80° C. to obtain a solution. The mixture was allowed to cool to ambient temperature, and the resulting product filtered, washed with a little ethanol, then dried in vacuo at 50° C. to afford the title compound as a white crystalline solid (4.3 g). m.pt. (DSC) 131.9-134.2° C.

The XRPD pattern of this product is shown in FIG. 1.

ii) α-Phenylcinnamate Salt

α-Phenylcinnamic acid (0.249 g) was added to a solution of 4-((R)-2-{6-[2-(2,6-dichlorobenzyloxy)-ethoxy]-hexylamino}-1-hydroxyethyl)-2-hydroxymethyl-phenol (0.54 g) in isopropanol (5 mL). The solution was seeded with product and allowed to stir at ambient temperature for 20 h. The product was filtered, washed with a little isopropanol, then dried in vacuo at 50° C. to afford the title compound as a crystalline white solid (0.56 g). m.pt. (DSC) 116.1-117.9° C.

Figure 2:
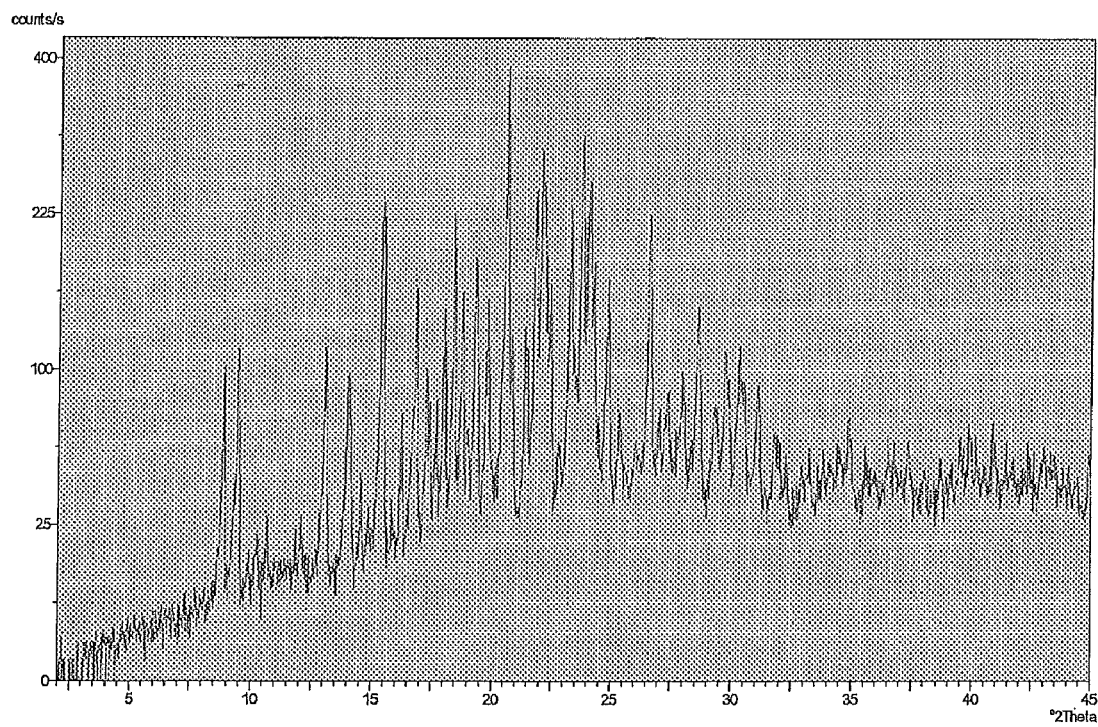
FIG. 2 illustrates an XRPD pattern of a α-phenycinnamate salt referred to in Example 78.

The XRPD pattern of this product is shown in FIG. 2.

iii) 1-Naphthoate Salt

1-Naphthoic acid (0.16 g, 0.97 mmol) was added to a solution of 4-((R)-2-{6-[2-(2,6-dichlorobenzyloxy)-ethoxy]-hexylamino}-1-hydroxyethyl)-2-hydroxymethyl-phenol (0.46 g) in MIBK (5 mL) and the resulting suspension warmed to 80° C. The resulting solution was allowed to cool slowly to ambient temperature and left to stir for 20 h. The product was filtered, washed with MIBK, then dried in vacuo at 50° C. to afford the title compound as a solid (0.49 g). m.pt. (DSC) 91.4-95.2° C.

Figure 3:
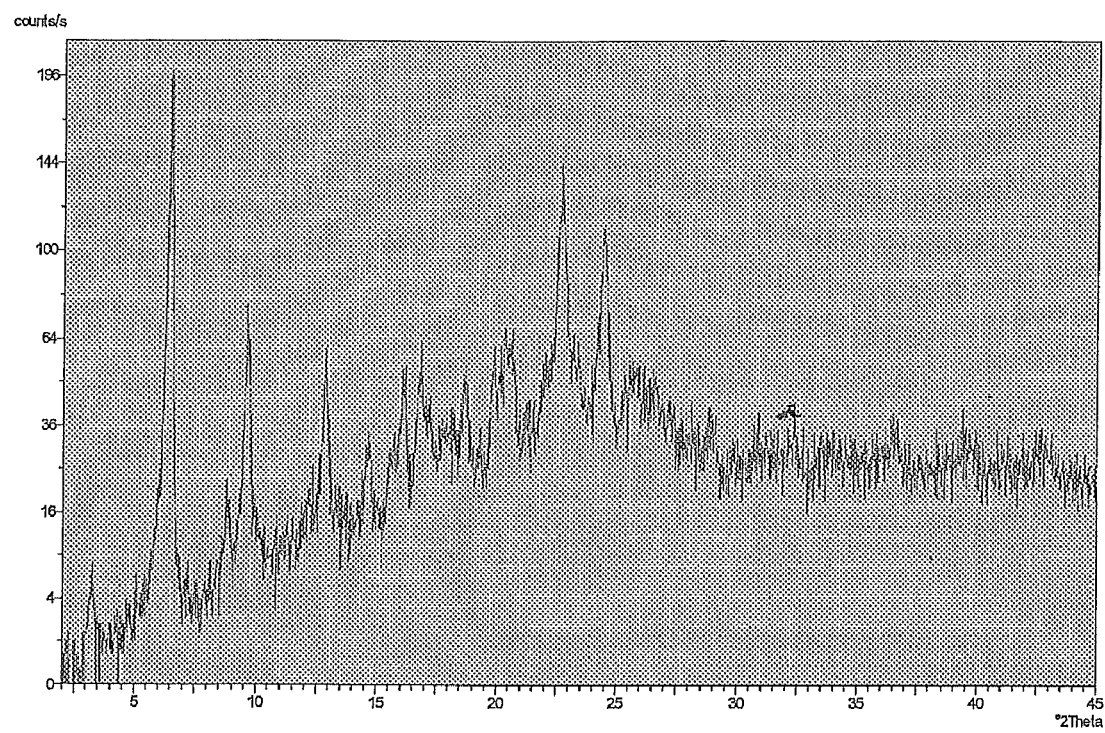
FIG. 3 illustrates an XRPD pattern of a 1-naphthoate salt referred to in Example 78.

The XRPD pattern of this product is shown in FIG. 3.

iv) (R)-Mandelate Salt (R)-Mandelic acid (0.15 g) was added to a solution of 4-((R)-2-{6-[2-(2,6-dichlorobenzyloxy)-ethoxy]-hexylamino}-1-hydroxyethyl)-2-hydroxymethyl-phenol (0.48 g) in MIBK (5 mL) and the resulting suspension warmed to 80° C. The resulting solution was allowed to cool slowly to ambient temperature and left to stir for 20 h. The product was filtered, washed with MIBK, then dried in vacuo at 50° C. to afford the title compound as a solid (0.44 g).

Figure 4:
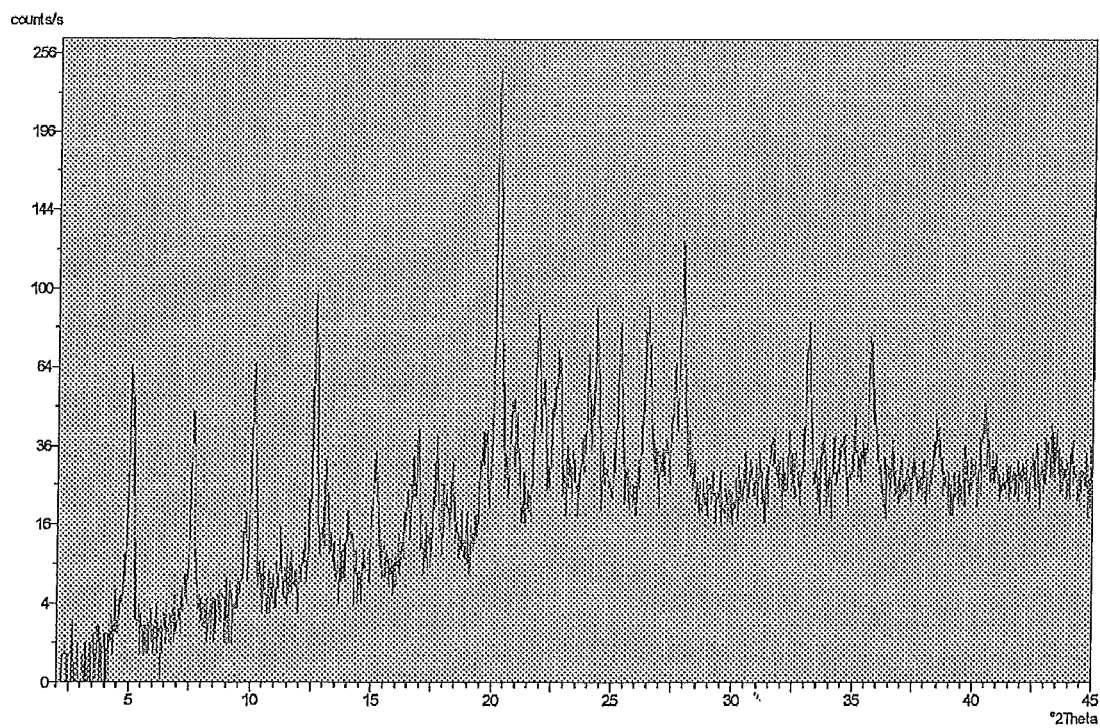
FIG. 4 illustrates an XRPD pattern of a (R)-mandelate salt referred to in Example 78.

The XRPD pattern of this product is shown in FIG. 4.

Example 79

4-{(1R)-2-[(5-{2-[(2,6-Dichlorobenzyl)oxy]ethoxy}pentyl)amino]-1-hydroxyethyl}-2-(hydroxymethyl)phenol acetate i) 2-({2-[(5-Bromopentyl)oxy]ethoxy}methyl)-1,3-dichlorobenzene

Prepared from 2-[(2,6-dichlorobenzyl)oxy]ethanol using method described in Example 77 ii)
LCMS RT=3.91 min ii) (5R)-3-(5-{2-[(2,6-Dichlorobenzyl)oxy]ethoxy}pentyl)-5-(2,2-dimethyl-4H-1,3-benzodioxin-6-yl)-1,3-oxazolidin-2-one Prepared using method described in Example 21 iii)
LCMS RT=3.75 min iii) (1R)-2-[(5-{2-[(2,6-Dichlorobenzyl)oxy]ethoxy}pentyl)amino]-1-(2,2-dimethyl-4H-1,3-benzodioxin-6-yl)ethanol Prepared using method described in Example 1 xii)
LCMS RT=2.71 min iv) 4-{(1R)-2-[(5-{2-[(2,6-Dichlorobenzyl)oxy]ethoxy}pentyl)amino]-1-hydroxyethyl}-2-(hydroxymethyl)phenol acetate Prepared using method described in Example 1 xiii)
LCMS RT=2.38 min ES+ve 472, 474 and 476 (MH)$^+$

Example 80

4-((1R)-2-{[6-(2-{[3-(Cyclopentylsulfonyl)benzyl]oxy}ethoxy)hexyl]amino}-1-hydroxyethyl)-2-(hydroxymethyl)phenol acetate i) Tert-butyl{[3-(cyclopentylthio)benzyl]oxy}dimethylsilane

Tert-butyl[(3-iodobenzyl)oxy]dimethylsilane (WO9513095) (1.44 g) in dry 1-methyl-2-pyrrolidone (15 ml) and triethylamine (4 ml) was stirred at room temperature under nitrogen. 1-1'Bis(diphenylphosphino)ferrocene (110 mg) and tris(dibenzylideneacetone)dipalladium(0) (258 mg) were added and the mixture was stirred for 15 min. Cyclopentyl mercaptan (0.42 g) was then added, and the reaction mixture stirred at 60° C. for 2 h. The reaction mixture was cooled to room temperature, poured onto water and extracted with diethyl ether. The combined organic extracts were dried (MgSO$_4$) and the solvent evaporated in vacuo. The residue was purified on a 50 g SPE, eluting with a stepped gradient of 10 to 100% dichloromethane-cyclohexane to give the title compound (1.09 g) LCMS RT=4.67 min ii) [3-(Cyclopentylthio)phenyl]methanol

A solution of tetrabutylammonium fluoride in THF (1 M, 6 ml) was added to a solution of tert-butyl{[3-(cyclopentylthio)benzyl]oxy}dimethylsilane (1.09 g) in dry THF (10 ml). The solution was stirred for 18 h under nitrogen and the solvent was evaporated in vacuo. The residue was partitioned between dichloromethane and water. The organic phase was separated and washed with water. The organic phase was separated and the solvent evaporated in vacuo. The residue was purified on a 10 g silica SPE cartridge, eluting with a stepped gradient of 10% to 100% dichloromethane-cyclohexane to give the title compound (0.65 g). LCMS RT=3.3 min iii) (5R)-3-[6-(2-{[3-(Cyclopentylthio)benzyl]oxy}ethoxy)hexyl]-5-(2,2-dimethyl-4H-1,3-benzodioxin-6-yl)-1,3-oxazolidin-2-one A solution of [3-(cyclopentylthio)phenyl]methanol (270 mg) in dry DMF (10 ml) under nitrogen was treated with sodium hydride (60% dispersion on mineral oil, 57 mg) and the mixture stirred for 1 h. 2-({6-[(5R)-5-(2,2-Dimethyl-4H-1,3-benzodioxin-6-yl)-2-oxo-1,3-oxazolidin-3-yl]hexyl}oxy)ethyl methanesulfonate (0.4 g) in dry DMF (2 ml) was then added and the mixture stirred for 18 h. Phosphate buffer solution (pH6.5) was added and the mixture extracted with ethyl acetate. The combined extracts were washed with water and dried (MgSO$_4$), filtered, and evaporated in vacuo. The residue was purified on a 10 g silica SPE cartridge, eluting with 10% to 20% ethyl acetate-cyclohexane to give the title compound (0.23 g). LCMS RT=4.08 min.

iv) (5R)-3-[6-(2-{[3-(Cyclopentylsulfinyl)benzyl]oxy}ethoxy)hexyl]-5-(2,2-dimethyl-4H-1,3-benzodioxin-6-yl)-1,3-oxazolidin-2-one Sodium periodate (333 mg) was added to a solution of (5R)-3-[6-(2-{[3-(cyclopentylthio)benzyl]oxy}ethoxy)hexyl]-5-(2,2-dimethyl-4H-1,3-benzodioxin-6-yl)-1,3-oxazolidin-2-one (230 mg) in ethanol (12 ml) and water (4 ml). The mixture was stirred at room temperature under nitrogen for 3 h. and the ethanol evaporated in vacuo. The aqueous phase was diluted with water and extracted with ethyl acetate. The combined ethyl acetate extracts were dried (MgSO4) filtered, and evaporated in vacuo. The residue was purified on a 10 g silica SPE cartridge, eluting with a stepped gradient of 10% to 100% ethyl acetate-cyclohexane, to give the title compound (201 mg). LCMS RT=3.54 min.

v) (5R)-3-[6-(2-{[3-(Cyclopentylsulfonyl)benzyl]oxy}ethoxy)hexyl]-5-(2,2-dimethyl-4H-1,3-benzodioxin-6-yl)-1,3-oxazolidin-2-one 3-Chloroperbenzoic acid (60 mg;57% purity) was added to a solution of (1 R)-2-{[6-(2-{[3(5R)-3-[6-(2-{[3-(cyclopentylsulfinyl)benzyl]oxy}ethoxy)hexyl]-5-(2,2-dimethyl-4H-1,3-benzodioxin-6-yl)-1,3-oxazolidin-2-one (106 mg) in dry DCM (5 ml) stirring under nitrogen at 0° C. The solution was allowed to warm up to room temperature and stirred for 2.5 h. The reaction mixture was quenched with aqueous sodium sulphite solution. The organic layer was separated and washed twice with aqueous sodium sulphite, dried (MgSO$_4$) filtered and evaporated in vacuo. The residue was purified on a 5 g silica SPE cartridge, eluting with a stepped gradient of 20% to 100% ethyl acetate-cyclohexane to give the title compound (96 mg). LCMS RT=3.68 min.

vi) (1R)-2-{[6-(2-{[3-(Cyclopentylsulfonyl)benzyl]oxy}ethoxy)hexyl]amino}-1-(2,2-dimethyl-4H-1,3-benzodioxin-6-yl)ethanol The title compound was prepared from (5R)-3-[6-(2-{[3-(cyclopentylsulfonyl)benzyl]oxy}ethoxy)hexyl]-5-(2,2-dimethyl-4H-1,3-benzodioxin-6-yl)-1,3-oxazolidin-2-one by a procedure similar to that described in example 4 ii. The residue was purified on a SPE cartridge, eluting with methanol-dichloromethane-ammonia (10:90:1), to give the title compound. LCMS RT=2.80 min.

vii) 4-((1R)-2-{[6-(2-{[3-(Cyclopentylsulfonyl)benzyl]oxy}ethoxy)hexyl]amino}-1-hydroxyethyl)-2-(hydroxymethyl)phenol acetate The title compound was prepared from (1R)-2-{[6-(2-{[3-(cyclopentylsulfonyl)benzyl]oxy}ethoxy)hexyl]amino}-1-(2,2-dimethyl-4H-1,3-benzodioxin-6-yl)ethanol, by a procedure similar to that described in example 4 iii. LCMS RT=2.41 min. ES+ve 548 (M+H)$^+$ Example 81

4-((1R)-2-{[6-(2-{[3-(Cyclopentylsulfinyl)benzyl]oxy}ethoxy)hexyl]amino}-1-hydroxyethyl)-2-(hydroxymethyl)phenol acetate i) (1R)-2-{[6-(2-{[3-(Cyclopentylsulfinyl)benzyl]oxy}ethoxy)hexyl]amino}-1-(2,2-dimethyl-4H-1,3-benzodioxin-6-yl)ethanol The title compound was prepared from (5R)-3-[6-(2-{[3-(cyclopentylsulfinyl)benzyl]oxy}ethoxy)hexyl]-5-(2,2-dimethyl-4H-1,3-benzodioxin-6-yl)-1,3-oxazolidin-2-one (example 80 iv) by a procedure similar to that described in example 4 ii) LCMS RT=2.69 min.

ii) 4-((1R)-2-{[6-(2-{[3-(Cyclopentylsulfinyl)benzyl]oxy}ethoxy)hexyl]amino}-1-hydroxyethyl)-2-(hydroxymethyl)phenol acetate The title compound was prepared from (1R)-2-{[6-(2-{[3-(cyclopentylsulfinyl)benzyl]oxy}ethoxy)hexyl]amino}-1-(2,2-dimethyl-4H-1,3-benzodioxin-6-yl)ethanol by a procedure similar to that described in example 4 iii).
LCMS RT=2.43 min ES+ve 534 (M+H)$^+$ Example 82

4-((1R)-2-{[6-(2-{[3-(Cyclopentylthio)benzyl]oxy}ethoxy)hexyl]amino}-1-hydroxyethyl)-2-(hydroxymethyl)phenol acetate i) (1R)-2-{[6-(2-{[3-(Cyclopentylthio)benzyl]oxy}ethoxy)hexyl]amino}-1-(2,2-dimethyl-4H-1,3-benzodioxin-6-yl)ethanol The title compound was prepared from (5R)-3-[6-(2-{[3-(cyclopentylthio)benzyl]oxy}ethoxy)hexyl]-5-(2,2-dimethyl-4H-1,3-benzodioxin-6-yl)-1,3-oxazolidin-2-one by a procedure similar to that described in example 4 ii). LCMS RT=3.18 min ii) 4-((1R)-2-{[6-(2-{[3-(Cyclopentylthio)benzyl]oxy}ethoxy)hexyl]amino}-1-hydroxyethyl)-2-(hydroxymethyl)phenol acetate The title compound was prepared from (1R)-2-{[6-(2-{[3-(cyclopentylthio)benzyl]oxy}ethoxy)hexyl]amino}-1-(2,2-dimethyl-4H-1,3-benzodioxin-6-yl)ethanol by a procedure similar to that described in example 4 iii). LCMS RT=2.82 min ES+ve m/z=518 (M+H)$^+$ Biological Activity The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1 and 4 to 82 had $IC_{50}$ values below 1 μM.

Potency at human beta1 and beta3 adrenoceptors was determined in functional studies using Chinese hamster ovary cells transfected with either the human beta1 adrenoceptor or the human beta3 adrenoceptor. Agonist activity was assessed by measuring changes in intracellular cyclic AMP. For particularly preferred compounds of the invention, selectivity for beta2 adrenoceptors over beta1 adrenoceptors was typically 10 fold or greater. Selectivity for beta2 adrenoceptors over beta3 adrenoceptors was typically 5 fold or greater.

The onset of action and duration of action in vitro was assessed on isolated superfused airway preparations (human or guinea pig). Tissues were contracted either electrically or by spasmogen. Agonist was perfused over the tissue until maximum relaxation was achieved, and onset of action determined. Perfusion of the agonist was then ceased and duration determined by the time taken for the contractile response to re-establish. For particularly preferred compounds of the invention, onset was typically less than 30 min. Duration was typically >3 h.

Particularly preferred compounds of the invention are potent and long-acting inhibitors of histamine-induced bronchospasm in conscious guinea pigs. They also demonstrate an improved therapeutic index in conscious guinea pigs (bronchoprotective effects vs blood pressure lowering effects) relative to established long-acting beta2 agonist bronchodilators.

The particularly preferred compounds of the invention show low oral bioavailability in rat and dog. In human hepatocyte cultures they are metabolised to products that are significantly less potent at the beta2 adrenoceptor than the parent compound.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound which is (1R)-2-[(6-{2-[(2,6-dichlorobenzyl)oxy]ethoxy}hexyl)amino]-1-(2,2-dimethyl-4H-1,3-benzodioxin-6-yl)ethanol.

2. (5R)-3-(6-{2-[(2,6-dichlorobenzyl)oxy]ethoxy}hexyl)-5-(2,2-dimethyl-4H-1,3-benzodioxin-6-yl)-1,3-oxazolidin-2-one.

* * * * *

UNITED STATES PATENT AND TRADEMARK OFFICE
Certificate

Patent No. 8,198,483 B2　　　　　　　　　　　　　　　　　　Patented: June 12, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Philip Charles Box, Stevenage (GB); Diane Mary Coe, Stevenage (GB); Brian Edgar Looker, Stevenage (GB); and Panayiotis Alexandrou Procopiou, Stevenage (GB).

Signed and Sealed this Twelfth Day of August 2014.

*FEREYDOUN SAJJADI*
*Supervisory Patent Examiner*
*Art Unit 1671*
*Technology Center 1600*